(12) United States Patent
Kalthoff et al.

(10) Patent No.: US 8,815,802 B2
(45) Date of Patent: *Aug. 26, 2014

(54) GLP-1 ANALOGUES AND DERIVATIVES

(75) Inventors: Christoph Kalthoff, Frederikssund (DK); Jesper Lau, Farum (DK); Jane Spetzler, Broenshoej (DK); Patrick William Garibay, Holte (DK); Jacob Kofoed, Vaerloese (DK); Lars Linderoth, Alleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/516,312

(22) PCT Filed: Dec. 16, 2010

(86) PCT No.: PCT/EP2010/069931
§ 371 (c)(1),
(2), (4) Date: Nov. 16, 2012

(87) PCT Pub. No.: WO2011/080102
PCT Pub. Date: Jul. 7, 2011

(65) Prior Publication Data
US 2013/0053311 A1    Feb. 28, 2013

Related U.S. Application Data

(60) Provisional application No. 61/288,601, filed on Dec. 21, 2009.

(30) Foreign Application Priority Data

Dec. 16, 2009 (EP) .................................. 09179390

(51) Int. Cl.
*A61K 38/26* (2006.01)
*A61P 3/10* (2006.01)
*C07K 14/605* (2006.01)
*A61K 38/00* (2006.01)
*C07K 14/65* (2006.01)

(52) U.S. Cl.
CPC ................. *C07K 14/65* (2013.01); *A61K 38/00* (2013.01); *A61K 38/26* (2013.01); *G01N 2333/605* (2013.01)
USPC ............................ 514/11.7; 514/7.2; 530/308

(58) Field of Classification Search
CPC ........ A61K 38/26; A61K 38/00; A61K 38/02; A61K 38/16; A61K 47/48215; C07K 14/605; C07K 14/62; C12N 2501/335; C12N 5/0676; G01N 2333/605; A61L 27/54
See application file for complete search history.

(56) References Cited

U.S. PATENT DOCUMENTS

| | | | |
|---|---|---|---|
| 5,545,618 | A | 8/1996 | Buckley et al. |
| 2001/0011071 | A1 | 8/2001 | Knudsen et al. |
| 2006/0286129 | A1 | 12/2006 | Sarubbi |
| 2008/0076705 | A1 | 3/2008 | Kodra et al. |

FOREIGN PATENT DOCUMENTS

| | | |
|---|---|---|
| CN | 101463081 A | 6/2009 |
| JP | 2010-530962 A | 9/2010 |
| WO | 9808871 A1 | 3/1998 |
| WO | 99/43705 A1 | 9/1999 |
| WO | 99/43706 A1 | 9/1999 |
| WO | 99/43707 A1 | 9/1999 |
| WO | 00/07617 A1 | 2/2000 |
| WO | 00/16797 A2 | 3/2000 |
| WO | 03/072195 A2 | 9/2003 |
| WO | 2004/067548 A2 | 8/2004 |
| WO | 2005/027978 A2 | 3/2005 |
| WO | 2005/058958 A2 | 6/2005 |
| WO | 2005/121090 A1 | 12/2005 |
| WO | 2006/005667 A2 | 1/2006 |
| WO | 2006/082204 A1 | 8/2006 |
| WO | 2006/097537 A2 | 9/2006 |
| WO | 2006/097538 A1 | 9/2006 |
| WO | 2006096515 A2 | 9/2006 |
| WO | 2006/127948 A2 | 11/2006 |
| WO | 2007/128817 A2 | 11/2007 |
| WO | 2009/030738 A1 | 3/2009 |
| WO | 2009/030771 A1 | 3/2009 |
| WO | 2009/083549 A1 | 7/2009 |

OTHER PUBLICATIONS

Dolensky et al., "New Building Blocks for Fluorinated Imidazole," Jorunal of Organic Chemistry, vol. 66(13), pp. 4687-4691 (2001).

(Continued)

*Primary Examiner* — Christina Bradley
*Assistant Examiner* — Randall L Beane
(74) *Attorney, Agent, or Firm* — Richard W. Bork

(57) ABSTRACT

The invention relates to a GLP-1 analog which comprises a histidine (H) residue at a position corresponding to position 31 of GLP-1(7-37) (SEQ ID NO: 1), a glutamine (Q) residue at a position corresponding to position 34 of GLP-1 (7-37) (SEQ ID NO: 1), and a maximum of ten amino acid modifications as compared to GLP-1 (7-37) (SEQ ID NO: 1); wherein the H residue is designated $H^{31}$, and the Q residue is designated $Q^{34}$; or a pharmaceutically acceptable salt, amide, or ester thereof. The invention also relates to derivatives thereof, as well as the pharmaceutical use of these analogs and derivatives, for example in the treatment and/or prevention of all forms of diabetes and related diseases. The invention furthermore relates to corresponding novel side chain intermediates. The derivatives are suitable for oral administration.

12 Claims, No Drawings

(56) References Cited

OTHER PUBLICATIONS

Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.

Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.

Travis B R et al. Organic Letters. "Facile Oxidation of Aldehydes to Acids and Esters With Oxone." 2003. vol. 5(7). pp. 1031-1034.

Murage E N et al. Bioorganic & Medicinal Chemistry. "Search for -Helical Propensity in the Receptor-Bound Conformation of Glucagon-Like Peptide-1." 2008. vol. 16. pp. 10106-10112.

Dumelin et al.., "A Portable Albumin Binder From a DNA-Encoded Chemical Library", Angewandte Chemie (International Edition in English), vol. 47(17), pp. 3196-3201 (Apr. 14, 2008).

Chae et al., "The Fatty Acid Conjugated Exendin-4 Analogs for Type 2 Antidiabetic Therapeutics", Journal of the Controlled Release, vol. 144, pp. 10-16 (Jan. 14, 2010).

SEQUENCE LISTING

```
<160> NUMBER OF SEQ ID NOS: 27

<210> SEQ ID NO 1
<211> LENGTH: 31
<212> TYPE: PRT
<213> ORGANISM: Homo Sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
```

```
<222> LOCATION: (24)..(24)
<223> OTHER INFORMATION: X = E
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (30)..(30)
<223> OTHER INFORMATION: X = K
<220> FEATURE:
<221> NAME/KEY: MISC_FEATURE
<222> LOCATION: (32)..(32)
<223> OTHER INFORMATION: X = E

<400> SEQUENCE: 2

His Xaa Glu Gly Thr Phe Thr Ser Asp Val Ser Ser Tyr Leu Glu Gly
1               5                   10                  15

Gln Ala Ala Lys Glu Phe Ile Xaa Xaa Leu Val Xaa Gly Xaa Gly Xaa
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = imidazopropionic acid
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (31)..(31)
<223> OTHER INFORMATION: X = K

<400> SEQUENCE: 3

Xaa Ala Glu Gly Thr Phe Thr Ser Asp Val Ser Ser Tyr Leu Glu Xaa
1               5                   10                  15

Gln Ala Ala Xaa Glu Phe Ile Ala Xaa Leu Val Xaa Gly Arg Xaa
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
```

```
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 4

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (6)..(6)
<223> OTHER INFORMATION: X = K
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 5

His Xaa Glu Gly Thr Xaa Thr Ser Asp Val Ser Ser Tyr Leu Glu Xaa
1               5                   10                  15

Gln Ala Ala Xaa Glu Phe Ile Ala Xaa Leu Val Xaa Gly Arg Gly
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (32)..(32)
<223> OTHER INFORMATION: X = K
```

<400> SEQUENCE: 6

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly Xaa
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (6)..(6)
<223> OTHER INFORMATION: X = K
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 7

His Xaa Glu Gly Thr Xaa Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Sythetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (31)..(31)
<223> OTHER INFORMATION: X = K

<400> SEQUENCE: 8

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly Xaa
            20                  25                  30

<210> SEQ ID NO 9
<211> LENGTH: 31
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (12)..(12)
<223> OTHER INFORMATION: X = K
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 10

His Xaa Glu Gly Thr Phe Thr Ser Asp Val Ser Xaa Tyr Leu Glu Xaa
1               5                   10                  15

Gln Ala Ala Xaa Glu Phe Ile Ala Xaa Leu Val Xaa Gly Arg Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X = K
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
```

```
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 11

His Ala Glu Gly Thr Xaa Thr Ser Asp Val Ser Ser Tyr Leu Glu Xaa
1               5                   10                  15

Gln Ala Ala Xaa Glu Phe Ile Ala Xaa Leu Val Xaa Gly Arg Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = G
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 12

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (12)..(12)
<223> OTHER INFORMATION: X = K
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = H
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 13

His Xaa Glu Gly Thr Phe Thr Ser Asp Val Ser Xaa Tyr Leu Glu Xaa
1               5                   10                  15
```

```
Gln Ala Ala Xaa Glu Phe Ile Ala Xaa Leu Val Xaa Gly Arg Gly
            20                  25                  30
```

<210> SEQ ID NO 14
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = A
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 14

```
His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30
```

<210> SEQ ID NO 15
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = des
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 15

```
Xaa Ala Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30
```

<210> SEQ ID NO 16
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = S
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 16

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (21)..(21)
<223> OTHER INFORMATION: X = K
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 17

His Xaa Glu Gly Thr Phe Thr Ser Asp Val Ser Ser Tyr Leu Glu Gly
1               5                   10                  15

Gln Ala Ala Xaa Xaa Phe Ile Ala Xaa Leu Val Xaa Gly Arg Gly
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (21)..(21)
<223> OTHER INFORMATION: X = K
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 18

```
His Xaa Glu Gly Thr Phe Thr Ser Asp Val Ser Ser Tyr Leu Glu Xaa
1               5                   10                  15

Gln Ala Ala Xaa Xaa Phe Ile Ala Xaa Leu Val Xaa Gly Arg Gly
            20              25              30
```

<210> SEQ ID NO 19
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (21)..(21)
<223> OTHER INFORMATION: X = K
<220> FEATURE:
<221> NAME/KEY: MISC_FEATURE
<222> LOCATION: (24)..(24)
<223> OTHER INFORMATION: X = E
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (31)..(31)
<223> OTHER INFORMATION: X = P

<400> SEQUENCE: 19

```
His Xaa Glu Gly Thr Phe Thr Ser Asp Val Ser Ser Tyr Leu Glu Xaa
1               5                   10                  15

Gln Ala Ala Xaa Xaa Phe Ile Xaa Xaa Leu Val Xaa Gly Arg Xaa
            20              25              30
```

<210> SEQ ID NO 20
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q
<220> FEATURE:
<221> NAME/KEY: MISC_FEATURE
<222> LOCATION: (31)..(31)
<223> OTHER INFORMATION: X = K

<400> SEQUENCE: 20

```
His Ala Glu Gly Thr Phe Thr Ser Asp Val Ser Ser Tyr Leu Glu Gly
1               5                   10                  15
```

-continued

Gln Ala Ala Lys Glu Phe Ile Ala Xaa Leu Val Xaa Gly Arg Xaa
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X = K
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 21

His Ala Glu Gly Thr Phe Thr Ser Asp Val Ser Ser Tyr Leu Glu Xaa
1               5                   10                  15

Gln Ala Ala Xaa Glu Phe Ile Ala Xaa Leu Val Xaa Gly Arg Gly
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (18)..(18)
<223> OTHER INFORMATION: X = K
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 22

His Xaa Glu Gly Thr Phe Thr Ser Asp Val Ser Ser Tyr Leu Glu Xaa
1               5                   10                  15

Gln Xaa Ala Xaa Glu Phe Ile Ala Xaa Leu Val Xaa Gly Arg Gly
            20                  25                  30

<210> SEQ ID NO 23
<211> LENGTH: 31
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (19)..(19)
<223> OTHER INFORMATION: X = I
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (21)..(21)
<223> OTHER INFORMATION: X = K
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 23

His Xaa Glu Gly Thr Phe Thr Ser Asp Val Ser Ser Tyr Leu Glu Gly
 1               5                  10                  15

Gln Ala Xaa Xaa Xaa Phe Ile Ala Xaa Leu Val Xaa Gly Arg Gly
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = Aib
<220> FEATURE:
<221> NAME/KEY: MISC_FEATURE
<222> LOCATION: (10)..(10)
<223> OTHER INFORMATION: X = K
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 24

His Xaa Glu Gly Thr Phe Thr Ser Asp Xaa Ser Ser Tyr Leu Glu Xaa
 1               5                  10                  15

Gln Ala Ala Xaa Glu Phe Ile Ala Xaa Leu Val Xaa Gly Arg Gly
            20                  25                  30

<210> SEQ ID NO 25
<211> LENGTH: 31
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X = E
<220> FEATURE:
<221> NAME/KEY: MISC_FEATURE
<222> LOCATION: (18)..(18)
<223> OTHER INFORMATION: X = K
<220> FEATURE:
<221> NAME/KEY: MISC_FEATURE
<222> LOCATION: (20)..(20)
<223> OTHER INFORMATION: X = R
<220> FEATURE:
<221> NAME/KEY: MISC_FEATURE
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 25

His Ala Glu Gly Thr Phe Thr Ser Asp Val Ser Ser Tyr Leu Glu Xaa
1               5                   10                  15

Gln Xaa Ala Xaa Glu Phe Ile Ala Xaa Leu Val Xaa Gly Arg Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: x = des
<220> FEATURE:
<221> NAME/KEY: MISC_FEATURE
<222> LOCATION: (25)..(25)
<223> OTHER INFORMATION: x = H
<220> FEATURE:
<221> NAME/KEY: MISC_FEATURE
<222> LOCATION: (28)..(28)
<223> OTHER INFORMATION: X = Q

<400> SEQUENCE: 26

Xaa Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = N-methyl-A
<220> FEATURE:
<221> NAME/KEY: MISC_FEATURE
```

```
<222> LOCATION: (25)..(25)
<223> OTHER INFORMATION: X = H
<220> FEATURE:
<221> NAME/KEY: MISC_FEATURE
<222> LOCATION: (28)..(28)
<223> OTHER INFORMATION: X = Q

<400> SEQUENCE: 27

His Xaa Glu Gly Thr Phe Thr Ser Asp Val Ser Ser Tyr Leu Glu Gly
1               5                   10                  15

Gln Ala Ala Lys Glu Phe Ile Ala Xaa Leu Val Xaa Gly Arg Gly
            20                  25                  30
```

GLP-1 ANALOGUES AND DERIVATIVES

CROSS-REFERENCE TO RELATED APPLICATIONS

This application is a 35 U.S.C. §371 national stage application of International Patent Application PCT/EP2010/069931 (published as WO 2011/080102), filed Dec. 16, 2010, which claimed priority of European Patent Application 09179390.1, filed Dec. 16, 2009; this application further claims priority under 35 U.S.C. §119 of U.S. Provisional Application 61/288,601, filed Dec. 21, 2009.

FIELD OF THE INVENTION

The present invention relates to analogues and derivatives of Glucagon-Like Peptide-1 (GLP-1) comprising a histidine at position 31 and a glutamine at position 34, and their pharmaceutical use.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 14, 2012. The Sequence Listing is made up of 1 kilobyte, and the information contained in the attached "SEQUENCE LISTING" is identical to the information in the specification as originally filed. No new matter is added.

BACKGROUND OF THE INVENTION

WO 00/16797 relates to the use of GLP-1 or analogues in treatment of stroke and includes a number of proposals for the design of GLP-1 analogues and derivatives of improved insulin stimulating properties, or of enhanced degradation resistance in plasma.

WO 2006/096515 relates to transferrin fusion proteins of GLP-1 peptides, such as GLP-1(7-37), which has been modified by mutating K34 to Q, A, or N (claim 16 therein).

WO 2009/030771 relates to peptides such as GLP-1 derivatised with A-B-C-D-, including some in which K34 has been mutated to Q (Examples 68, 69, 71).

U.S. Pat. No. 5,545,618 relates to GLP-1 analogues useful for diabetes treatment and includes a number of proposals for the design of GLP-1 analogues and derivatives of improved insulin stimulating properties, or of enhanced degradation resistance in plasma.

Liraglutide, a GLP-1 derivative for once daily administration which is marketed by Novo Nordisk NS, is disclosed in Example 37 of WO 98/08871.

Semaglutide, a GLP-1 derivative for once weekly administration which is under development by Novo Nordisk A/S, is disclosed in Example 4 of WO 06/097537.

SUMMARY OF THE INVENTION

The invention relates to analogues of GLP-1, and derivatives thereof.

In the GLP-1 analogue of the invention, the native amino acid residues at position 31 as well as 34, i.e. W and K, respectively, have been substituted to H and Q, respectively.

A maximum of ten amino acids of the analogue may have been modified in total, as compared to native GLP-1(7-37) (SEQ ID NO: 1), including the substitutions at position 31 and 34.

More in particular, the invention relates to a GLP-1 analogue which comprises a histidine residue at a position corresponding to position 31 of GLP-1(7-37) (SEQ ID NO: 1), and a glutamine residue at a position corresponding to position 34 of GLP-1(7-37).

Thus, the analogue may be said to comprise, or have, $H^{31}$ and $Q^{34}$. The analogue furthermore preferably has a maximum of ten amino acid modifications as compared to GLP-1 (7-37) (SEQ ID NO: 1).

The invention also relates to a derivative of this analogue, as well as a pharmaceutically acceptable salt, amide, or ester of the analogue, and a pharmaceutically acceptable salt, amide, or ester of the derivative.

The invention furthermore relates to the pharmaceutical use of these compounds, preferably for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The invention furthermore relates to intermediate products in the form of side chains, which are relevant for the preparation of certain GLP-1 derivatives of the invention.

The peptides and derivatives of the invention are biologically active. Also, or alternatively, they have a protracted pharmacokinetic profile. Also, or alternatively, they are stable against degradation by gastro intestinal enzymes. Also, or alternatively, they have a high oral bioavailability. These properties are of importance in the development of next generation GLP-1 compounds for subcutaneous, intravenous, and/or in particular oral administration.

DESCRIPTION OF THE INVENTION

The invention relates to a GLP-1 analogue which comprises a histidine residue at a position corresponding to position 31 of GLP-1(7-37) (SEQ ID NO: 1), a glutamine residue at a position corresponding to position 34 of GLP-1(7-37), and a maximum of ten amino acid modifications as compared to GLP-1(7-37) (SEQ ID NO: 1); wherein the H residue is designated $H^{31}$, and the Q residue is designated $Q^{34}$; or a pharmaceutically acceptable salt, amide, or ester thereof.

The invention also relates to a derivative of this analogue, and a pharmaceutically acceptable salt, amide, or ester thereof; as well as to the pharmaceutical use of the derivative and the analogue.

The invention furthermore relates to two intermediate products (Chem. 67, and Chem. 68), wherein PG represents a protection group.

In what follows, Greek letters may be represented by their symbol or the corresponding written name, for example: α=alpha; β=beta; ε=epsilon; γ=gamma; ω=omega; etc. Also, the Greek letter of μ my be represented by "u", e.g. in μl=ul, or in μM=uM.

An asterisk (*) in a chemical formula designates i) a point of attachment, ii) a radical, and/or iii) an unshared electron.

GLP-1 Analogues

The term "GLP-1 analogue" or "analogue of GLP-1" as used herein refers to a peptide, or a compound, which is a variant of the human Glucagon-Like Peptide-1 (GLP-1(7-37)), the sequence of which is included in the sequence listing as SEQ ID NO: 1. The peptide having the sequence of SEQ ID NO: 1 may also be designated "native" GLP-1.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

In a particular embodiment, the GLP-1 analogue of the invention refers to a modified GLP-1(7-37) peptide in which a number of amino acid residues have been changed as compared to native GLP-1(7-37) (SEQ ID NO: 1). These changes, or modifications, may represent, independently, one or more amino acid substitutions, additions, and/or deletions.

The GLP-1 analogues of the invention may be described by reference to i) the number of the amino acid residue in native GLP-1(7-37) which corresponds to the amino acid residue which is modified (i.e., the corresponding position in native GLP-1), and to ii) the actual modification. The following are non-limiting, illustrative examples of suitable analogue nomenclature, as used herein.

The compound of the invention is a GLP-1 analogue GLP-1(7-37) which comprises a histidine residue at a position corresponding to position 31 of GLP-1(7-37), a glutamine residue at a position corresponding to position 34 of GLP-1(7-37), and a maximum of ten amino acid modifications as compared to GLP-1(7-37), where GLP-1(7-37) refers to native GLP-1(7-37) having SEQ ID NO: 1.

If for example the analogue of the invention would have only two amino acid modifications in total, namely the two modifications specifically referred to, this means that the amino acid sequence of the analogue is otherwise identical to that of native GLP-1, and such analogue may then, e.g., be designated $(H^{31},Q^{34})$-GLP-1(7-37)(SEQ ID NO: 9). This represents the amino acid sequence of native GLP-1 (SEQ ID NO: 1), where W at position 31 has been substituted with H, and K at position 34 has been substituted with Q. This analogue may also be designated $[His^{31},Gln^{34}]$GLP-1(7-37)-peptide)(SEQ ID NO: 9), $[His^{31},Gln^{34}]$GLP-1(7-37))(SEQ ID NO: 9), or simply (31H, 34Q), where the reference to GLP-1(7-37) is implied.

Another example of an analogue of the invention is $[Aib^8, His^{31}, Gln^{34}]$GLP-1-(7-37) (SEQ ID NO: 4) which has a total of 3 amino acid modifications, in which the alanine at position 8 has been substituted with alpha-aminoisobutyric acid (Aib), in addition to the two substitutions at positions 31 and 34, discussed above. This analogue may simply be designated (8Aib, 31H, 34Q), where the reference to GLP-1(7-37) is implied.

As a still further example, $[Aib^8,Glu^{30},His^{31},Gln^{34},Lys^{36}]$ GLP-1(7-37)yl-Glu (SEQ ID NO: 2) designates another GLP-1(7-37) analogue of the invention, with a total of 6 amino acid modifications, in which the alanine at position 8 has been substituted with aminoisobutyric acid (Aib), the alanine at position 30 has been substituted with glutamic acid, the tryptophan at position 31 has been substituted with histidine, the lysine at position 34 has been substituted with glutamine, the arginine at position 36 has been substituted with lysine, and a glutamic acid has been added to the C-terminus, at position no. 38. This analogue may simply be designated (8Aib, 30E, 31H, 34Q, 36K, 38E), where the reference to GLP-1(7-37) is implied.

As a still further example, des7 (or $Des^7$) in relation to an analogue of GLP-1(7-37) refers to an analogue, in which the amino acid corresponding to the N-terminal amino acid of GLP-1(7-37), histidine, has been deleted. This analogue may also be designated GLP-1(8-37).

Similarly, (des7+des8); (des7, des8); (des7-8); or ($Des^7$, $Des^8$) in relation to an analogue of GLP-1(7-37) refers to an analogue in which the two N-terminal amino acids, histidine and alanine, have been deleted. This analogue may also be designated GLP-1(9-37).

As a still further example, an analogue "comprising $Des^7$ or $Imp^7$", refers to a GLP-1(7-37) analogue, which, when compared to native GLP-1, comprises a deletion of histidine at position 7, or a substitution of histidine at position 7 with imidazopropionic acid (Imp), respectively.

Analogues "comprising" certain specified modifications may comprise further modifications, when compared to SEQ ID NO: 1. For example, non-limiting examples of analogues of the invention comprising $Des^7$ or $Imp^7$ are the peptide parts of Chem. 31, Chem. 37, Chem. 40, and Chem. 41, of which all except Chem. 40 are derivatives of the invention (Chem. 40 is an analogue of the invention).

Non-limiting examples of an analogue comprising Des7, His31, and Gln34 are the following: $[Des^7,His^{31},Gln^{34}]$GLP-1(7-37) peptide (SEQ ID NO: 15), and $N^8$ 3H-Imidazol-4-yl-acetyl][$His^{31}$,Gln]GLP-1(8-37)-peptide (SEQ ID NO: 9). In the latter compound a monopeptide mimetic of His is attached to the new N-terminus, Ala 8, via an amide bond.

Suitable His- or His-Ala mimetics that may be used as a kind of a substitute for the deleted N-terminal amino acids, if any, comprise a heterocyclic, nitrogen-containing, aromatic ring structure, e.g. pyridine or imidazole. Preferred His- or His-Ala mimetics are derivatives of an imidazole or a pyridine, other than His and His-Ala, in one embodiment having a substituent with a free carboylic acid group, which can form an amide bond with an amino group of the N-terminal amino acid of the peptide. The term imidazole refers to imidazoles as a class of heterocycles with similar ring structure but varying substituents, and vice-versa for pyridine.

As is apparent from the above examples, amino acid residues may be identified by their full name, their one-letter code, and/or their three-letter code. These three ways are fully equivalent.

The expressions "a position equivalent to" or "corresponding position" may be used to characterise the site of modification in a modified GLP-1(7-37) sequence by reference to native GLP-1(7-37) (SEQ ID NO: 1). Equivalent or corresponding positions, as well as the number of modifications, are easily deduced, e.g. by simple handwriting and eye-balling; and/or a standard protein or peptide alignment program may be used, such as "align" which is a Needleman-Wunsch alignment. The algorithm is described in Needleman, S.B. and Wunsch, C.D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12, or preferably at −10, and the penalties for additional residues in a gap at −2, or preferably at −0.5.

An example of such alignment is inserted hereinbelow, in which sequence no. 1 is SEQ ID NO: 1, and SEQ ID NO: 2 is the analogue (8Aib, 30E, 31H, 34Q, 36K, 38E) thereof:
1: GLP-1(7-37):
2: GLP-1(7-37)_Analogue:
Matrix: EBLOSUM62
Gap_penalty: 10.0
Extend_penalty: 0.5
Length: 32
Identity: 26/32 (81.2%)
Similarity: 28/32 (87.5%)

Gaps: 1/32 (3.1%)
Score: 132.0

```
1:  1  HAEGTFTSDVSSYLEGQAAKEFIAWLVKGRG-  31
       |.||||||||||||||||||||||..||:|:|
2:  1  HXEGTFTSDVSSYLEGQAAKEFIEHLVQGKGE  32
```

In case of non-natural amino acids such as Imp, N-methyl-Ala, and/or Aib being included in the sequence, or in case of His-Ala mimetics, these may, for alignment purposes, be replaced with X. If desired, X can later be manually corrected.

The term "peptide", as e.g. used in the context of the analogues of the invention, refers to a compound which comprises a series of amino acids intereconnected by amide (or peptide) bonds.

In a particular embodiment the peptide is to a large extent, or predominantly, composed of amino acids interconnected by amide bonds (e.g., at least 50%, 60%, 70%, 80%, or at least 90%, by molar mass). In another particular embodiment the peptide consists of amino acids interconnected by peptide bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide is a) composed of, or b) consists of, i) 29, ii) 30, iii) 31, or iv) 32 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine (in what follows sometimes abbreviated "a" as f.ex. in "a8", which accordingly refers to D-Ala$^8$) and D-leucine, Aib (α-aminoisobutyric acid), β-alanine, N-methyl-alanine, and des-amino-histidine (desH, alternative name imidazopropionic acid, abbreviated Imp).

In what follows, all amino acids for which the optical isomer is not stated is to be understood to mean the L-isomer (unless otherwise specified).

The GLP-1 analogues and derivatives of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assay described in Example 48 herein.

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

Non-limiting examples of GLP-1 derivatives include heterologous fusion proteins or conjugates of GLP-1 analogues, with e.g. the Fc portion of an immunoglobulin such as IgG, with human albumin, with antibodies such as a glucagon binding antibody heavy chain variable region, or with fragments or analogues of any of these (see, e.g., US 2007/0161087, WO 2005/058958, and WO 2007/124463 A2). Additional examples include PEGylated GLP-1 peptides (see, e.g., WO 2005/058954, WO 2004/093823, and WO 2006/124529), as well as acylated GLP-1 peptides (see, e.g., WO 98/08871, WO2005/027978, WO 2006/097537, and WO 2009/030771).

In a preferred embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, a preferred substituent, or side chain, as a whole may be referred to as an albumin binding moiety.

In another particular embodiment, the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion in-between the protracting moiety and the point of attachment to the peptide, which portion may be referred to as a linker, linker moiety, spacer, or the like. The presence of a linker is optional; hence if no linker is present the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by conjugation chemistry such as by alkylation, acylation, ester formation, or amide formation; or to a cysteine residue, such as by maleimide or haloacetamide (such as bromo-/fluoro-/iodo-) coupling.

In a preferred embodiment, an active ester of the albumin binding moiety and/or the protracting moiety, optionally with a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

In one embodiment, the invention relates to a derivative which comprises, preferably has, an albumin binding moiety attached to i) $K^{12}$, ii) $K^{16}$, iii) $K^{18}$, iv) $K^{22}$, v) $K^{24}$, vi) $K^{26}$, vii) $K^{27}$, iiX) $K^{36}$, and/or ix) $K^{37}$. As explained above, each residue number in superscript refers to the corresponding position in GLP-1(7-37) (SEQ ID NO: 1). Furthermore, as also explained above, ordinary script may be used instead of superscript to designate the position number. E.g., "$K^{12}$" is fully equivalent to "12K".

Corresponding position numbers are preferably identified by handwriting and eyeballing, or by using a suitable alignment program, as explained above.

For the present purposes, the terms "albumin binding moiety", "protracting moiety", and "linker" include the un-reacted as well as the reacted forms of these molecules. Whether or not one or the other form is meant is clear from the context in which the term is used.

In one aspect the albumin binding moiety comprises, or consists of, a protracting moiety selected from Chem. 1, Chem. 2, Chem. 3, and Chem. 4:

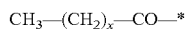     Chem. 1:

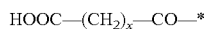     Chem. 2:

     Chem. 3:

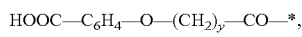     Chem. 4:

in which x is an integer in the range of 6-18, and y is an integer in the range of 3-17.

In one embodiment, *—(CH$_2$)$_x$—* refers to straight or branched, preferably straight, alkylene in which x is an integer in the range of 6-18.

In another embodiment, *—(CH$_2$)$_y$—* refers to straight or branched, preferably straight, alkylene in which y is an integer in the range of 3-17.

In another aspect the albumin binding moiety comprises, or consists of, a protracting moiety selected from fatty diacids, and fatty acids with a distal (terminal) phenyl or phenoxy group, optionally substituted. Optional substituents to the phenyl and phenoxy group have a molar mass not higher than 150 Da, preferably not higher than 125 Da, more preferably not higher than 100 Da, even more preferably not higher than 75 Da, or most preferably not higher than 50 Da. Examples of substituents include, without limitation, lower linear or branched C1-C5 alkyl.

The molar mass (M) of a chemical substance is the mass of one mole of the substance. The molar mass is quoted in dalton, symbol Da, with the definition 1 Da=1 g/mol.

Molar mass may be calculated from standard atomic weights, and is often listed in chemical catalogues. The molar mass of a compound is given by the sum of the standard atomic weights of the atoms which form the compound multiplied by the molar mass constant, $M_u$ which equals 1 g/mol. As an example, the molecular mass of tert. butyl (C$_4$H$_9$) is M(C$_4$H$_9$)=([4×12.01]+[9×1.008])×1 g/mol=57 Da.

Standard atomic weights are published by the International Union of Pure and Applied Chemistry (IUPAC), and also reprinted in a wide variety of textbooks, commercial catalogues, wallcharts etc.

For the attachment to the GLP-1 peptide, the acid group of the fatty acid, or one of the acid groups of the fatty diacid, forms an amide bond with the epsilon amino group of a lysine residue in the GLP-1 peptide, optionally via one or more linkers.

The term "fatty acid" refers to aliphatic monocarboxylic acids having from 4 to 28 carbon atoms, it is preferably unbranched, and/or even numbered, and it may be saturated or unsaturated.

The term "fatty diacid" refers to fatty acids as defined above but with an additional carboxylic acid group in the omega position. Thus, fatty diacids are dicarboxylic acids.

The nomenclature is as is usual in the art, for example *—COOH, as well as HOOC—*, refers to carboxy; *—C$_6$H$_4$—* to phenylene; *—CO—*, as well as *—OC—*, to carbonyl (O=C<**); C$_6$H$_5$—O—* to phenoxy; and HN$_4$C—* to any tetrazolyl radical. In particular embodiments, the aromatics, such as the phenoxy and the phenylene radicals, may be, independently, ortho, meta, or para. In another particular embodiment, the tetrazolyl radical is 1H-tetrazol-5yl.

In a preferred embodiment the linker moiety, if present, has from 5 to 30 C-atoms, preferably from 5 to 25 C-atoms, more preferably from 5 to 20 C-atoms, or most preferably from 5 to 17 C-atoms. In additional preferred embodiments, the linker moiety, if present, has from 4 to 20 hetero atoms, preferably from 4 to 18 hetero atoms, more preferably from 4 to 14 hetero atoms, or most preferably from 4 to 12 hetero atoms. Particularly preferred examples of hetero atoms are N-, and O-atoms. H-atoms are not hetero atoms.

In another embodiment, the linker comprises at least one OEG molecule, and/or at least one glutamic acid residue, or rather the corresponding radicals (OEG designates a di-radical of 8-amino-3,6-dioxaoctanic acid, i.e. this radical: *—NH—(CH$_2$)$_2$—O—(CH$_2$)$_2$—O—CH$_2$—CO—*).

The amino acid glutamic acid comprises two carboxylic acid groups. Its gamma-carboxy group is preferably used for forming an amide bond with the epsilon-amino group of lysine, or with an amino group of an OEG molecule, if present, or with the amino group of another Glu residue, if present. The amino group of Glu in turn forms an amide bond with the carboxy group of the protracting moiety, or with the carboxy group of an OEG molecule, if present, or with the gamma-carboxy group of another Glu, if present. This way of inclusion of Glu is occasionally briefly referred to as "gamma-Glu".

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 analogues and derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI assay. This assay is described in Example 51, Example 53, and Example 55 herein.

Pharmaceutically Acceptable Salt, Amide, or Ester

The analogues, derivatives, and intermediate products of the invention may be in the form of a pharmaceutically acceptable salt, amide, or ester.

Salts are e.g. formed by a chemical reaction between a base and an acid, e.g.: NH$_3$+H$_2$SO$_4$→(NH$_4$)$_2$SO$_4$.

The salt may be a basic salt, an acid salt, or it may be neither nor (i.e. a neutral salt). Basic salts produce hydroxide ions and acid salts hydronium ions in water.

The salts of the analogues and derivatives of the invention may be formed with added cations or anions that react with anionic or cationic groups, respectively. These groups may be situated in the peptide moiety, and/or in the side chain of the compounds of the invention.

Non-limiting examples of anionic groups of the compounds of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the peptides and derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the peptides and derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the peptide or derivative is in the form of a pharmaceutically acceptable amide, preferably with an amide group at the C-terminus of the peptide. In a still further particular embodiment, the peptide or derivative is in the form a pharmaceutically acceptable ester.

Intermediate Products

The invention furthermore relates to two intermediate products (Chem. 67, and Chem. 68), wherein PG represents a protection group. Non-limiting examples of PG groups are —OH, or groups functionalised as an activated ester, for example, without limitation, OPfp, OPnp, and OSuc.

Other suitable activated esters may be selected, e.g., according to the teaching of M. Bodanszky, "Principles of Peptide Synthesis", 2nd ed., Springer Verlag, 1993.

Functional Properties

In a first aspect, the analogues and/or derivatives of the invention have a good potency. Also, or alternatively, in a second aspect, they have a protracted pharmacokinetic profile. Also, or alternatively, in a third aspect, they are stable against degradation by gastro intestinal enzymes. Also, or alternatively, in a fourth aspect they have a relatively low albumin binding affinity. Also, or alternatively, in a fifth aspect, they have a high oral bioavailability.

Biological Activity (Potency)

According to the first aspect, the analogues and derivatives are biologically active, or potent.

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 48.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% TWEEN™ polysorbate surfactant; 0.1% BSA; 0.5 mM IBMX; 1 mM ATP; 1 uM GTP; pH 7.4.

An alternative medium is: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% TWEEN™ polysorbate-20, pH 7.4.

In a further particular embodiment, the analogues and/or derivatives of the invention have an $EC_{50}$ at or below 4500 pM, preferably below 4500 pM, more preferably below 4000 pM, even more preferably below 3500 pM, or most preferably below 3000 pM.

In another particular embodiment the analogues and/or derivatives of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Example 54 herein, or as described in Example 43 of WO09/030738.

Also, or alternatively, the effect on glucose mediated insulin secretion in vivo may be determined in pharmacodynamic studies in minipigs (IVGTT), e.g. as described in Example 55.

Also, or alternatively, the effect on feed intake in vivo may be determined in pharmacodynamic studies in pigs, e.g. as described in Example 56.

Protraction—Receptor Binding/Low and High Albumin

According to the second aspect, the analogues and/or derivatives of the invention are protracted.

The ability of the analogues and/or derivatives of the invention to bind to the GLP-1 receptor in the presence of a low and a high concentration of albumin, respectively, may be determined as described in Example 49 herein.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low). On the other hand, albumin binding may not always be desirable, or the binding to albumin may become too strong. Therefore, the desirable ranges for $IC_{50}$ (low albumin), $IC_{50}$ (high albumin)/, and the ratio high/low may vary from compound to compound, depending on the intended use and the circumstances surrounding such use, and on other compound properties of potential interest.

In a particular embodiment, the GLP-1 receptor binding affinity ($IC_{50}$) in the presence of 0.005% HSA (low albumin) is below 1000.00 nM, preferably below 600.00 nM, more preferably below 100.00 nM, or most preferably below 50.00 nM.

A suitable assay for determining receptor binding at high and low albumin concentration is disclosed in Example 49 herein.

Protraction—Half Life In Vivo in Rats

According to the second aspect, the derivatives of the invention are protracted. In a particular embodiment, protraction may be determined as half-life ($T_{1/2}$) in vivo in rats after i.v. administration. In additional embodiments, the half-life is at least 4 hours, preferably at least 5 hours, even more preferably at least 6 hours, or most preferably at least 7 hours.

A suitable assay for determining half-life in vivo in rats after i.v. administration is disclosed in Example 51 herein.

Protraction—Half Life In Vivo in Minipigs

According to the second aspect, the derivatives of the invention are protracted. In a particular embodiment protraction may be determined as half-life ($T_{1/2}$) in vivo in minipigs after i.v. administration. In additional embodiments, the half-life is at least 8 hours, preferably at least 12 hours, more preferably at least 16 hours, still more preferably at last 24 hours, even more preferably at least 36 hours, or most preferably at least 48 hours.

A suitable assay for determining half-life in vivo in minipigs after i.v. administration is disclosed in Example 52 herein.

Degradation by Gastro Intestinal Enzymes

According to the third aspect, the analogues and/or derivatives of the invention are stable, or stabilised, against degradation by one or more gastro intestinal enzymes.

Gastro intestinal enzymes include, without limitation, exo and endo peptidases, such as pepsin, trypsin, chymotrypsin, elastases, and carboxypeptidases. The stability may be tested against these gastro intestinal enzymes in the form of purified enzymes, or in the form of extracts from the gastrointestinal system.

In particular embodiments, the analogue or derivative of the invention has an in vitro half-life ($T_{1/2}$), in an extract of rat small intestines, divided by the corresponding half-life ($T_{1/2}$) of GLP-1(7-37), of at least 1, preferably above 1.0, more preferably at least 1.2, still more preferably at least 2.0, even more preferably at least 3.0, or most preferably at least 4.0. In other words, a ratio (SI) may be defined for each derivative, viz. as the in vitro half-life ($T_{1/2}$) of the derivative in question, in an extract of rat small intestines, divided by the corresponding half-life ($T_{1/2}$) of GLP-1(7-37).

A suitable assay for determining in vitro half-life in an extract of rat small intestines is disclosed in Example 50 herein.

In additional particular embodiments, the enzymatic stability of the derivatives of the invention, determined using a suitable method such as the one of Example 50, is improved as compared to a) the compound of Example 68 of WO 2009/030771; b) the compound of Example 69 of WO 2009/030771; and/or c) the compound of Example 71 of WO 2009/030771.

Albumin Binding Affinity

According to the fourth aspect, the derivatives of the invention have a relatively low binding affinity to human serum albumin, HSA.

While a certain level of albumin binding is generally desirable from a protraction point of view, the binding to albumin should not be too tight, as this could potentially negatively influence the binding of the derivative to the GLP-1 receptor, which is important for the biological activity.

Binding affinity to HSA may be determined using any suitable method, such as the one of Example 57 herein.

Binding affinity to HSA may be expressed as $K_d$, or $K_d$ apparent, wherein $K_d$ is a dissociation constant that refers to the chemical equilibrium equation leading to the HSA-bound derivative.

The smaller the dissociation constant ($K_d$), the higher the binding affinity between the GLP-1 derivative and HSA.

Thus, according to this fourth aspect, the $K_d$, or the apparent $K_d$, of the derivatives of the invention may be relatively high, corresponding to a relatively low binding to HSA.

In a particular embodiment, surprisingly, these derivatives with a relatively low binding to HSA, are nevertheless of an increased enzymatic stability, in particular against degradation by gastro intestinal enzymes, wherein the enzymatic stability may be determined as described in Example 50 herein. Reference is also specifically had to the section headed "Degradation by gastro intestinal enzymes", above.

The combination of increased enzymatic stability with low albumin binding affinity gives the possibility to increase the free fraction of the analogue or derivative in plasma and thereby increase in vivo potency. It also gives a larger design range with respect to plasma half-life, as compared to known GLP-1 derivatives that generally have a high albumin binding affinity, as focus has hitherto mainly been on prolonging half-life.

Oral Bioavailability

According to the fifth aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as their potency is generally satisfactory, and/or as long as their half-life is also generally satisfactory.

The present inventors identified a novel class of GLP-1 derivatives, which have a surprisingly high oral bioavailability, and at the same time a satisfactory potency, and/or half-life.

In a particular embodiment, surprisingly, these derivatives having a high oral bioavailability also have a high binding affinity (i.e. a low $IC_{50}$ value) to the GLP-1 receptor at a low concentration of albumin. These features are of importance with a view to obtaining a low daily oral dose of the active pharmaceutical ingredient, which is desirable for various reasons, including, e.g., economy of production, likelihood of potential safety issues, as well as administration comfort issues, and environmental concerns.

In another particular embodiment, surprisingly, these derivatives having a high oral bioavailability also exhibit a relatively low binding to human serum albumin (HSA), wherein the binding to HSA may, e.g., be determined as described in Example 57 herein. Reference is also specifically had to the section headed "Albumin binding affinity", above.

The combination of high oral bioavailability with low albumin binding affinity gives the possibility to lower the dose of the active pharmaceutical ingredient, which is desirable for various reasons, including, e.g., economy of production, likelihood of potential safety issues, as well as administration comfort issues, and environmental concerns. It also gives a larger design range with respect to plasma half-life, as compared to known GLP-1 derivatives that generally have a high albumin binding affinity.

Generally, the term bioavailability of an analogue, or derivative, of the invention refers to the fraction of an administered dose of the active pharmaceutical ingredient (API), such as an analogue or a derivative of the invention that reaches the systemic circulation unchanged. By definition, when an API is administered intravenously, its bioavailability is 100%. However, when an API is administered via other routes (such as orally), its bioavailability decreases (due to incomplete absorption and first-pass metabolism). Knowledge about bioavailability is essential when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing the corresponding dose administered.

A plasma API concentration vs time plot is made after both oral and intravenous administration. The absolute bioavailability (F) is the dose-corrected AUC-oral divided by AUC-intravenous.

The derivatives of the invention have an absolute oral bioavailability which is higher than that of a) liraglutide, and/or b) semaglutide; preferably at least 10% higher, more preferably at least 20% higher, even more preferably at least 30% higher, or most preferably at least 40% higher. Before testing oral bioavailability the analogues and/or derivatives of the invention may suitably be formulated as is known in the art of oral formulations of insulinotropic compounds, e.g. using any one or more of the formulations described in WO 2008/145728.

A test has been developed, described in Example 53, which was found to be a very good prediction of oral bioavailability. According to this test, after direct injection of the GLP-1 derivative into the intestinal lumen of rats, the concentration (exposure) thereof in plasma is determined, and the ratio of plasma concentration (pmol/l) divided by the concentration of the dosing solution (umol/l) is calculated for t=30 min. This ratio is a measure of intestinal bioavailability, and it has shown to correlate nicely with actual oral bioavailability data.

Additional particular embodiments of the derivatives of the invention are described in the section headed "particular embodiments" before the experimental section.

Production Processes

The production of peptides like GLP-1(7-37) and analogues thereof is well known in the art.

The analogues of the invention, or fragments thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza DOrwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the fragment and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those analogues of the invention which include non-natural amino acids and/or a covalently attached N-terminal mono- or dipeptide mimetic may e.g. be produced as described in the experimental part. Or see e.g. Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of analogues and derivatives of the invention are included in the experimental part.

Pharmaceutical Compositions

Pharmaceutical compositions comprising an analogue or a derivative of the invention, or a pharmaceutically acceptable salt, amide, alkyl, or ester thereof, and a pharmaceutically acceptable excipient may be prepared as is known in the art.

The term "excipient" broadly refers to any component other than the active therapeutic ingredient(s). The excipient may be an inert substance. In another embodiment it is an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. comprising water. A liquid formulation may be a solution, or a suspension. An aqueous formulation typically comprises at least 50% w/w water, or at least 60%, 70%, 80%, or even at least 90% w/w of water.

Alternatively, the pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the analogue or derivative, or from 0.01-50 mg, or from 0.01-20 mg, or from 0.01-10 mg.

The derivative of the invention may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. In a particular embodiment the composition is an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the $\beta$-cells; Cholestyramine, colestipol, clofibrate, gemfibrozil, lovastatin, pravastatin, simvastatin, probucol, dextrothyroxine, neteglinide, repaglinide; $\beta$-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and $\alpha$-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, $\beta$3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR $\beta$ agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to an analogue of the invention, and a derivative of the invention, for use as a medicament.

In particular embodiments, the analogue or derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving $\beta$-cell function, such as decreasing $\beta$-cell apoptosis, increasing $\beta$-cell function and/or $\beta$-cell mass, and/or for restoring glucose sensitivity to $\beta$-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia *nervosa*, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

PARTICULAR EMBODIMENTS

The following are particular embodiments of the invention:
1. A GLP-1 analogue which comprises a histidine (H) residue at a position corresponding to position 31 of GLP-1(7-37) (SEQ ID NO: 1), a glutamine (Q) residue at a position corresponding to position 34 of GLP-1(7-37) (SEQ ID NO: 1), and a maximum of ten amino acid modifications as compared to GLP-1(7-37) (SEQ ID NO: 1); wherein the H residue is designated $H^{31}$, and the Q residue is designated $Q^{34}$; or a pharmaceutically acceptable salt, amide, or ester thereof.
2. The analogue of embodiment 1, which has a maximum of nine amino acid modifications.
3. The analogue of embodiment 1 which has a maximum of eight amino acid modifications.
4. The analogue of embodiment 1 which has a maximum of seven amino acid modifications.
5. The analogue of embodiment 1 which has a maximum of six amino acid modifications.
6. The analogue of embodiment 1 which has a maximum of five amino acid modifications.
7. The analogue of embodiment 1 which has a maximum of four amino acid modifications.
8. The analogue of embodiment 1 which has a maximum of three amino acid modifications.
9. The analogue of embodiment 1 which has a maximum of two amino acid modifications.
10. The analogue of any one of embodiments 1-9 which has a minimum of two amino acid modifications.
11. The analogue of any one of embodiments 1-8 which has a minimum of three amino acid modifications.
12. The analogue of anyone of embodiments 1-7 which has a minimum of four amino acid modifications.
13. The analogue of anyone of embodiments 1-6 which has a minimum of five amino acid modifications.
14. The analogue of anyone of embodiments 1-5 which has a minimum of six amino acid modifications.
15. The analogue of anyone of embodiments 1-4 which has a minimum of seven amino acid modifications.
16. The analogue of anyone of embodiments 1-3 which has a minimum of eight amino acid modifications.
17. The analogue of anyone of embodiments 1-2 which has a minimum of nine amino acid modifications.
18. The analogue of embodiment 1 which has a minimum of ten amino acid modifications.
19. The analogue of embodiment 1 which has two amino acid modifications.
20. The analogue of embodiment 1 which has three amino acid modifications.
21. The analogue of embodiment 1 which has four amino acid modifications.
22. The analogue of embodiment 1 which has five amino acid modifications.
23. The analogue of embodiment 1 which has six amino acid modifications.
24. The analogue of embodiment 1 which has seven amino acid modifications.
25. The analogue of embodiment 1 which has eight amino acid modifications.
26. The analogue of embodiment 1 which has nine amino acid modifications.
27. The analogue of embodiment 1 which has ten amino acid modifications.
28. The analogue of any one of embodiments 1-27, wherein the amino acid modifications are, independently, substitutions, additions, and/or deletions.
29. The analogue of any one of embodiments 1-28, wherein the amino acid modifications are substitutions.
30. The analogue of any one of embodiments 1-28, wherein the amino acid modifications are deletions.
31. The analogue of any one of embodiments 1-28, wherein the amino acid modifications are additions.
32. The analogue of any one of embodiments 1-31, which has a C-terminal amide.
33. The analogue of any one of embodiments 1-31, which has a C-terminal *—COOH group.
34. The analogue of any one of embodiments 1-33, wherein the amino acid modifications are at one or more positions corresponding to the following positions in GLP-1(7-37) (SEQ ID NO: 1): 7, 8, 12, 16, 18, 22, 24, 25, 26, 27, 30, 31, 34, 36, 37, and/or 38.
35. The analogue of any one of embodiments 1-34, wherein the amino acid modifications other than $H^{31}$ and $Q^{34}$ are selected from the following: ($Des^7$ or $Imp^7$), ($Des^8$, $Aib^8$, N-methyl-$Ala^8$, D-$Ala^8$, $G^8$ or $S^8$), $K^{12}$, $K^{16}$, $K^{18}$, ($E^{22}$ or $K^{22}$), $K^{24}$, $I^{25}$, ($R^{26}$ or $H^{26}$), $K^{27}$, $E^{30}$, $H^{31}$, $Q^{34}$, $K^{36}$, ($K^{37}$ or $P^{37}$), and/or ($E^{38}$ or $K^{38}$).
36. The analogue of any one of embodiments 1-35 which comprises i) $Des^7$, or ii) $Imp^7$; preferably ii) $Imp^7$.
37. The analogue of any one of embodiments 1-36 which comprises i) $Des^8$, ii) $Aib^8$, iii) D-$Ala^8$, iv) N-methyl-$Ala^8$, v) $G^8$, or vi) $S^8$; preferably iii) D-$Ala^8$, iv) N-methyl-$Ala^8$, v) $G^8$, or vi) S⁸; more preferably v) G⁸, or vi) S⁸; even more preferably iii) D-Ala⁸, or iv) N-methyl-Ala⁸; or most preferably ii) Aib⁸.

38. The analogue of any one of embodiments 1-37 which comprises $K^{12}$.

39. The analogue of any one of embodiments 1-38 which comprises $K^{16}$.

40. The analogue of any one of embodiments 1-39 which comprises $K^{18}$.

41. The analogue of any one of embodiments 1-40 which comprises i) $E^{22}$, or ii) $K^{22}$, preferably i) $E^{22}$.

42. The analogue of any one of embodiments 1-41 which comprises $K^{24}$.

43. The analogue of any one of embodiments 1-42 which comprises $I^{25}$.

44. The analogue of any one of embodiments 1-43 which comprises i) $R^{26}$, or ii) $H^{26}$; preferably i) $R^{26}$.

45. The analogue of any one of embodiments 1-44 which comprises $K^{27}$.

46. The analogue of any one of embodiments 1-45 which comprises $E^{30}$.

47. The analogue of any one of embodiments 1-46 which comprises $K^{36}$.

48. The analogue of any one of embodiments 1-47 which comprises i) $K^{37}$, or ii) $P^{37}$; preferably i) $K^{37}$.

49. The analogue of any one of embodiments 1-48 which comprises i) $E^{38}$, or ii) $K^{38}$; preferably i) $E^{38}$.

50. The analogue of any one of embodiments 1-49, which comprises, preferably has, the following amino acid modifications: (i) (31H, 34Q) SEQ ID NO: 9; (ii) (31H, 34Q, 37K) SEQ ID NO: 20; (iii) (8G, 31H, 34Q) SEQ ID NO: 12; (iv) (8Aib, 31H, 34Q) SEQ ID NO: 4; (v) (8a, 31H, 34Q) SEQ ID NO: 14; (vi) (des7, 31H, 34Q) SEQ ID NO: 15; (vii) (8S, 31H, 34Q) SEQ ID NO: 16; (iix) (8-N-methyl-A, 31H, 34Q) SEQ ID NO: 27; (ix) (des7-8, 31H, 34Q) SEQ ID NO: 26; (x) (8Aib, 31H, 34Q, 38K) SEQ ID NO: 6; (xi) (8Aib, 12K, 31H, 34Q) SEQ ID NO: 7; (xii) (8Aib, 31H, 34Q, 37K) SEQ ID NO: 8; (xiii) (22K, 26R, 31H, 34Q) SEQ ID NO: 21; (xiv) (22E, 24K, 26R, 31H, 34Q) SEQ ID NO: 25; (xv) (12K, 22E, 26R, 31H, 34Q) SEQ ID NO: 11; (xvi) (8Aib, 26R, 27K, 31H, 34Q) SEQ ID NO: 17; (xvii) (7Imp, 22E, 26R, 31H, 34Q, 37K) SEQ ID NO: 3; (iixx) (8Aib, 30E, 31H, 34Q, 36K, 38E) SEQ ID NO: 2; (ixx) (8Aib, 12K, 22E, 26R, 31H, 34Q) SEQ ID NO: 5; (xx) (8Aib, 18K, 22E, 26R, 31H, 34Q) SEQ ID NO: 10; (xxi) (8Aib, 18K, 22E, 26H, 31H, 34Q) SEQ ID NO: 13; (xxii) (8Aib, 22E, 26R, 27K, 31H, 34Q) SEQ ID NO: 18; (xxiii) (8Aib, 22E, 24K, 26R, 31H, 34Q) SEQ ID NO: 22; (xiv) (8Aib, 25I, 26R, 27K, 31H, 34Q) SEQ ID NO: 23; (xv) (8Aib, 16K, 22E, 26R, 31H, 34Q) SEQ ID NO: 24; or (xvi) (8Aib, 22E, 26R, 27K, 30E, 31H, 34Q, 37P) SEQ ID NO: 19; preferably Chem. 20, Chem. 22, Chem. 41, Chem. 44, or Chem. 45.

51. The analogue of any one of embodiments 1-50, in which at least one amino acid residue has been deleted, as compared to GLP-1(7-37) (SEQ ID NO: 1).

52. The analogue of any one of embodiments 1-51, comprises des⁷ and/or des⁸, preferably both.

53. The analogue of any one of embodiments 1-52, wherein one amino acid has been deleted at a position corresponding to position 7 of GLP-1(7-37) (SEQ ID NO: 1).

54. The analogue of any one of embodiments 1-53, wherein one amino acid has been deleted at a position corresponding to position 8 of GLP-1(7-37) (SEQ ID NO: 1).

55. The analogue of any one of embodiments 1-54, wherein two amino acids have been deleted at positions corresponding to position 7 and 8 of GLP-1(7-37) (SEQ ID NO: 1).

56. The analogue of any one of embodiments 1-55, which is an analogue of GLP-1(8-37) (amino acids 2-31 of SEQ ID NO: 1), having up to ten, nine, eight, or six amino acid modifications as compared to GLP-1(7-37) (SEQ ID NO: 1).

57. The analogue of any one of embodiments 1-56, which is an analogue of GLP-1(9-37) (amino acids 3-31 respectively, of SEQ ID NO: 1), having up to ten, nine, eight, or six amino acid modifications as compared to GLP-1(7-37) (SEQ ID NO: 1).

58. The analogue of any one of embodiments 1-57, wherein a His-mimetic other than His is at a position corresponding to position 2 of GLP-1(7-37) (SEQ ID NO: 1).

59. The analogue of any one of embodiments 1-58, wherein a His-Ala-mimetic other than His-Ala is at the positions corresponding to position 7 and 8 of GLP-1(7-37) (SEQ ID NO: 1).

60. The analogue of any one of embodiments 58-59, wherein the His-mimetic, or the His-Ala mimetic, comprises a) imidazole; or b) pyridine.

61. The analogue of embodiment 60, wherein the imidazole is a derivative of an imidazole which comprises a *—CO end, for covalent coupling to *—NH of the N-terminal amino acid of the analogue, via formation of an amide bond.

62. The analogue of embodiment 60, wherein the pyridine is a derivative of pyridine which comprises a *—CO end, for covalent coupling to *—NH of the N-terminal amino acid of the analogue, via formation of an amide bond.

63. The analogue of embodiment 61, wherein the imidazole derivative is mono-substituted.

64. The analogue of embodiment 62, wherein the pyridine derivative is mono-substituted.

65. The analogue of any one of embodiments 61 and 63, wherein the imidazole derivative is substituted with a group comprising a carboxylic acid radical of a lower alkyl having from one to six carbon atoms.

66. The analogue of any one of embodiments 62 and 64, wherein the pyridine derivative is substituted with a group comprising a carboxylic acid radical of a lower alkyl having from one to six carbon atoms.

67. The analogue of any one of embodiments 65-66, wherein the carboxylic acid radical is selected from acetyl; and straight or branched propionyl, butyryl, pentanoyl; preferably acetyl.

68. The analogue of any one of embodiments 1-67, wherein the amino acid residue at the position corresponding to position 8 of GLP-1(7-37) (SEQ ID NO: 1) has 3H-Imidazol-4-yl-acetyl attached to its N-atom.

69. The analogue of any one of embodiments 1-68, wherein the amino acid residue at the position corresponding to position 8 of SEQ ID NO: 1 is alanine.

70. The analogue of any one of embodiments 60-69, wherein the imidazole is substituted with (methylcarbamoyl)-2-methyl-propionyl, (ethylcarbamoyl)-2-methyl-propionyl, (propylcarbamoyl)-2-methyl-propionyl, or (butylcarbamoyl)-2-methyl-propionyl; preferably with (ethylcarbamoyl)-2-methyl-propionyl.

71. The analogue of any one of embodiments 1-70, wherein the amino acid residue at the position corresponding to position 9 of GLP-1(7-37) (SEQ ID NO: 1) has {2-[2-(1H-Imidazol-4-yl)-ethylcarbamoyl]-2-methyl-propionyl} attached to its N-atom.

72. The analogue of any one of embodiments 60-71, wherein the pyridine is substituted with (methylcarbamoyl)-2-methyl-propionyl, (ethylcarbamoyl)-2-methyl-propionyl, (propylcarbamoyl)-2-methyl-propionyl, or (butylcarbamoyl)-2-methyl-propionyl; preferably with (methylcarbamoyl)-2-methyl-propionyl.

73. The derivative of any one of embodiments 1-72, wherein the amino acid residue at the position corresponding to position 9 of GLP-1(7-37) (SEQ ID NO: 1) has [2,2-dimethyl-3-oxo-3-(pyridin-2-ylmethylamino)propanoyl] attached to its N-atom.
74. The analogue of any one of embodiments 1-73, wherein the amino acid residue at the position corresponding to position 9 of the GLP-1 analogue is glutamic acid.
75. The analogue of any one of embodiments 1-74 which has a maximum of two K residues.
76. The analogue of any one of embodiments 1-75, which has a maximum of one K residue.
77. The analogue of any one of embodiments 1-76, wherein
   a) the position corresponding to any of the indicated positions of GLP-1(7-37) (SEQ ID NO: 1), and/or
   b) the number of amino acid modifications as compared to GLP-1(7-37) (SEQ ID NO: 1)
is/are identified by handwriting and eyeballing.
78. The analogue of any one of embodiments 1-77, wherein
   a) the position corresponding to any of the indicated positions of GLP-1(7-37) (SEQ ID NO: 1), and/or
   b) the number of amino acid modifications as compared to GLP-1(7-37) (SEQ ID NO: 1)
is/are identified by use of a standard protein or peptide alignment program.
79. The analogue of embodiment 78, wherein the alignment program is a Needleman-Wunsch alignment.
80. The analogue of any one of embodiments 78-79, wherein the default scoring matrix and the default identity matrix is used.
81. The analogue of any one of embodiments 78-80, wherein the scoring matrix is BLOSUM62.
82. The analogue of any one of embodiments 78-81, wherein the penalty for the first residue in a gap is −10 (minus ten).
83. The analogue of any one of embodiments 78-82, wherein the penalties for additional residues in a gap is −0.5 (minus point five).
84. The analogue of any one of embodiments 1-83, wherein, in analogy with the definition of $H^{31}$ and $Q^{34}$ in embodiment 1, a residue number, preferably any residue number, be it in superscript after an amino acid residue, or in ordinary script before or after the amino acid residue in question, refers to the corresponding position in GLP-1(7-37) (SEQ ID NO: 1).
85. A derivative of an analogue of any one of embodiments 1-84, or a pharmaceutically acceptable salt, amide, or ester thereof.
86. The derivative of embodiment 85 which has an albumin binding moiety attached to a lysine residue of the analogue, more preferably to the epsilon-amino group thereof, via an amide bond.
87. The derivative of embodiment 86, which has an albumin binding moiety attached to i) $K^{12}$, ii) $K^{16}$, iii) $K^{18}$, iv) $K^{22}$, v) $K^{24}$, vi) $K^{26}$, vii) $K^{27}$, iix) $K^{36}$, and/or ix) $K^{37}$, wherein each residue number in superscript refers to the corresponding position in GLP-1(7-37) (SEQ ID NO: 1).
88. The derivative of embodiment 87, which has an albumin binding moiety attached to i) $K^{12}$, iii) $K^{18}$, vi) $K^{26}$, and/or vii) $K^{27}$; preferably vi) $K^{26}$.
89. The derivative of embodiment 87, which has an albumin binding moiety attached to i) $K^{12}$, iii) $K^{18}$, v) $K^{24}$, vi) $K^{26}$, and/or vii) $K^{27}$.
90. The derivative of any one of embodiments 87-88, which has an albumin binding moiety attached to i) $K^{12}$, vi) $K^{26}$, and/or vii) $K^{27}$.
91. The derivative of embodiment 87, which has two albumin binding moieties attached, preferably to $K^{26}$ and $K^{37}$.
92. The derivative of any one of embodiments 85-91, in which the albumin binding moiety comprises a protracting moiety.
93. The derivative of embodiment 92, wherein the protracting moiety is selected from Chem. 1, Chem. 2, Chem. 3, and Chem. 4:

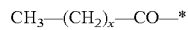   Chem. 1:

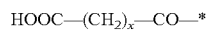   Chem. 2:

   Chem. 3:

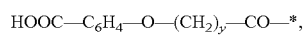   Chem. 4:

in which x is an integer in the range of 6-18, preferably 6-16, and y is an integer in the range of 3-17.
94. The derivative of embodiment 93, wherein the protracting moiety is Chem. 1, or Chem. 2, and x is preferably an even number.
95. The derivative of any one of embodiments 93-94, wherein x is i) 10, ii) 12, iii) 14, iv) 16, or v) 18; preferably iii) 14, or iv) 16; more preferably i) 10, ii) 12; or v) 18; or most preferably iv) 16.
96. The derivative of any one of embodiments 93-95, wherein the protracting moiety is Chem. 1.
97. The derivative of any one of embodiments 93-96, wherein Chem. 1 is represented by Chem. 1a:

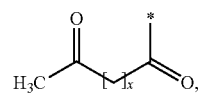

Chem. 1a where x is as defined in any one of embodiments 93-95.
98. The derivative of any one embodiments 93-95, wherein the protracting moiety is Chem. 2.
99. The derivative of any one of embodiments 93-95, and 98, wherein Chem. 2 is represented by Chem. 2a:

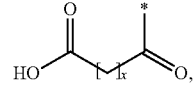

Chem. 2a where x is as defined in any one of embodiments 84-86.
100. The derivative of embodiment 93, wherein the protracting moiety is Chem. 3, and x is preferably an odd number.
101. The derivative of any one of embodiments 93 and 100, wherein x is i) 11, ii) 13, iii) 15, iv) 17, or v) 19; preferably iii) 15.
102. The derivative of any one of embodiments 93, and 100-101, wherein Chem. 3 is represented by Chem. 3a:

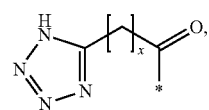

Chem. 3a where x is as defined in any one of embodiments 93, and 100-101.
103. The derivative of embodiment 93, wherein the protracting moiety is Chem. 4, and y is preferably an odd number.

104. The derivative of any one of embodiments 93 and 103, wherein y is i) 5, ii) 7, iii) 9, iv) 11, or v) 13; preferably iii) 9.

105. The derivative of any one of embodiments 93, and 103-104, wherein Chem. 4 is represented by Chem. 4a, or Chem. 4b:

Chem. 4a

Chem. 4b preferably by Chem. 4a;
wherein y is as defined in any one of embodiments 93, and 103-104.

106. The derivative of any one of embodiments 86-105, wherein the albumin binding moiety comprises one protracting moiety.

107. The derivative of any one of embodiments 86-105, wherein the albumin binding moiety comprises two protracting moieties.

108. The derivative of embodiment 107, wherein the protracting moieties are attached to one and the same lysine residue, preferably via a linker.

109. The derivative of embodiment 107, wherein the protracting moieties are attached to two different lysine residues, preferably via a linker.

110. The derivative of any one of embodiments 87-109, which comprises a linker.

111. The derivative of any one of embodiments 87-110, wherein the albumin binding moiety comprises a linker.

112. The derivative of any one of embodiments 92-111, wherein the albumin binding moiety further comprises a linker.

113. The derivative of any one of embodiments 110-112, wherein the linker is a di-radical which comprises an N radical and a CO radical, wherein i) the N-radical is represented by a first *—NR$^1$R$^2$ group, where R$^1$ and R$^2$ may, independently, designate hydrogen, carbon, or sulphur, optionally substituted; and ii) the CO radical is represented by a first *—CO group, and wherein, preferably, the first *—NR'R$^2$ group is capable of forming an amide bond with a second *—CO group, and the first *—CO group is capable of forming an amide bond with a second *—NR$^1$R$^2$ group, wherein the second *—NR$^1$R$^2$ group and the second *—CO group are defined as the first *—NR$^1$R$^2$ group and the first *—CO group, respectively, and form part, independently, of the structure of i) the analogue, ii) the protracting moiety, and/or iii) another linker.

114. The derivative of any one of embodiments 86-113, which comprises at least one linker selected from the group consisting of Chem. 5, Chem. 6, Chem. 7, Chem. 8, Chem. 9, and Chem. 10:

*—NH—CH$_2$—CH$_2$—(O—CH$_2$—CH$_2$)$_k$—O—(CH$_2$)$_n$—CO—*  Chem. 5:

*—NH—C(COOH)—(CH$_2$)$_2$—CO—*  Chem. 6:

*—N—C((CH$_2$)$_2$COOH)—CO—*  Chem. 7:

*—NH—C$_6$H$_8$—CO—*  Chem. 8:

*—NC$_5$H$_8$—CO—*  Chem. 9:

*—NH—SO$_2$—(CH$_2$)$_3$—CO—*  Chem. 10:

wherein k is an integer in the range of 1-5, and n is an integer in the range of 1-5; and wherein Chem. 6 and Chem. 7 are di-radicals of Glu.

115. The derivative of any one of embodiments 110-114, wherein the linker comprises Chem. 5, and wherein preferably Chem. 5 is a first linker element.

116. The derivative of any one of embodiments 114-115, wherein k is 1.

117. The derivative of any one of embodiments 114-116, wherein n is 1.

118. The derivative of any one of embodiments 114-117, wherein Chem. 5 is included m times, wherein m is an integer in the range of 1-10.

119. The derivative of embodiment 118, wherein m is an integer in the range of 1-6; preferably in the range of 1-4; more preferably m is 1 or 2; even more preferably m is 1; or most preferably m is 2.

120. The derivative of any one of embodiments 118-119, wherein, when m is different from 1, the Chem. 5 elements are interconnected via amide bond(s).

121. The derivative of any one of embodiments 114-120, wherein the linker consists of one or more Chem. 5 elements.

122. The derivative of any one of embodiments 114-121, wherein Chem. 5 is represented by Chem. 5a:

Chem. 5a wherein k and n are as defined in any one of embodiments 114-117.

123. The derivative of any one of embodiments 114-122, wherein the linker comprises a Glu di-radical, such as Chem. 6, and Chem. 7.

124. The derivative of any one of embodiments 114-123, wherein Chem. 6 and Chem. 7, independently, may be represented by Chem. 6a and Chem. 7a, respectively:

Chem. 6a

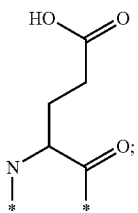

Chem. 7a most preferably by Chem. 6a.

125. The derivative of any one of embodiments 114-124, wherein the Glu di-radical, such as Chem. 6, and/or Chem. 7, independently, is included p times, wherein p is an integer in the range of 1-3.

126. The derivative of embodiment 125, wherein p is 1, 2, or 3; preferably 1 or 2, or most preferably 1.

127. The derivative of any one of embodiments 114-126, wherein the Glu di-radical is a radical of L-Glu or D-Glu, preferably of L-Glu.

128. The derivative of any one of embodiments 114-127, wherein the linker consists of a Glu di-radical, preferably Chem. 6, more preferably Chem. 6a.

129. The derivative of any one of embodiments 114-128, wherein the linker comprises Chem. 8.

130. The derivative of embodiment 129, where Chem. 8 is represented by Chem. 8a:

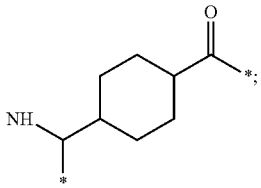

Chem. 8a preferably by Chem. 8b:

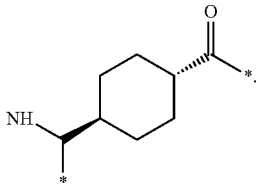

Chem. 8b

131. The derivative of any one of embodiments 114-130, which comprises Chem. 9.

132. The derivative of embodiment 131, wherein Chem. 9 is represented by Chem. 9a:

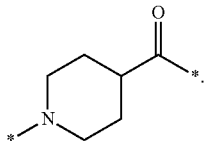

Chem. 9a

133. The derivative of any one of embodiments 114-132, which comprises Chem. 10.

134. The derivative of embodiment 133, wherein Chem. 10 is represented by Chem. 10a:

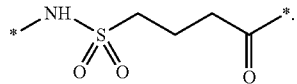

Chem. 10a

135. The derivative of any one of embodiments 114-134, wherein the linker consists of
two times Chem. 5, interconnected via an amide bond, and being connected at its *—NH end to the *—CO end of the protracting moiety, and at its *—CO end to the epsilon amino group of a lysine residue of the GLP-1 analogue.

136. The derivative of any one of embodiments 114-134, wherein the linker consists of Chem. 5, being connected at its *—NH end to the *—CO end of the protracting moiety, and at its *—CO end to the epsilon amino group of a lysine residue of the GLP-1 analogue.

137. The derivative of any one of embodiments 114-134, wherein the linker consists of Chem. 6, being connected at its *—NH end to the *—CO end of the protracting moiety, and at its *—CO end to the epsilon amino group of a lysine residue of the GLP-1 analogue.

138. The derivative of any one of embodiments 114-134, wherein the linker consists of two times Chem. 5 and one time Chem. 6, interconnected via amide bonds and in the sequence indicated, the linker being connected at its *—NH end to the *—CO end of the protracting moiety, and at its *—CO end to the epsilon amino group of a lysine residue of the GLP-1 analogue.

139. The derivative of any one of embodiments 114-134, wherein the linker consists of one time Chem. 6 and two times Chem. 5, interconnected via amide bonds and in the sequence indicated, the linker being connected at its *—NH end to the *—CO end of the protracting moiety, and at its *—CO end to the epsilon amino group of a lysine residue of the GLP-1 analogue.

140. The derivative of any one of embodiments 114-134, wherein the linker consists of one time Chem. 5, one time Chem. 6, and one time Chem. 5, interconnected via amide bonds and in the sequence indicated, the linker being connected at its *—NH end to the *—CO end of the protracting moiety, and at its *—CO end to the epsilon amino group of a lysine residue of the GLP-1 analogue.

141. The derivative of any one of embodiments 114-134, wherein the linker consists of one time Chem. 6 and one time Chem. 5, interconnected via amide bonds and in the sequence indicated, the linker being connected at its *—NH end to the *—CO end of the protracting moiety, and at its *—CO end to the epsilon amino group of a lysine residue of the GLP-1 analogue.

142. The derivative of any one of embodiments 114-134, wherein the linker consists of one time Chem. 8, one time Chem. 6, preferably in the D-form, and two times Chem. 5, interconnected via amide bonds and in the sequence indicated, the linker being connected at its *—NH end to the *—CO end of the protracting moiety, and at its *—CO end to the epsilon amino group of a lysine residue of the GLP-1 analogue.

143. The derivative of any one of embodiments 114-134, wherein the linker consists of one time Chem. 9, one time Chem. 6, and two times Chem. 5, interconnected via amide bonds and in the sequence indicated, the linker being connected at its *—NH end to the *—CO end of the protracting moiety, and at its *—CO end to the epsilon amino group of a lysine residue of the GLP-1 analogue.

144. The derivative of any one of embodiments 114-134, wherein the linker consists of one time Chem. 10, connected at its *—NH end to the *—CO end of the protracting moiety, and at its *—CO end to the epsilon amino group of a lysine residue of the GLP-1 analogue.

145. The derivative of any one of embodiments 110-144, wherein the one or more linker(s) are interconnected via amide bond(s).

146. A compound selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, and Chem. 66; or a pharmaceutically acceptable salt, amide, or ester thereof.

147. A compound characterised by its name, and selected from a listing of each of the names of the compounds of Examples 1-47 herein; or a pharmaceutically acceptable salt, amide, or ester thereof.

148. The compound of embodiment 147, which is a compound of embodiment 146.

149. The compound of any one of embodiments 146-148, which is an analogue of any one of embodiments 1-84.

150. The compound of any one of embodiments 146-148, which is a derivative of any one of embodiments 85-145.

151. The derivative of any one of embodiments 85-150, which is selected from the following:

$N^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib$^8$,His$^{31}$,Gln$^{34}$]GLP-1 (7-37)-peptide (SEQ ID NO: 4);

Chem. 21

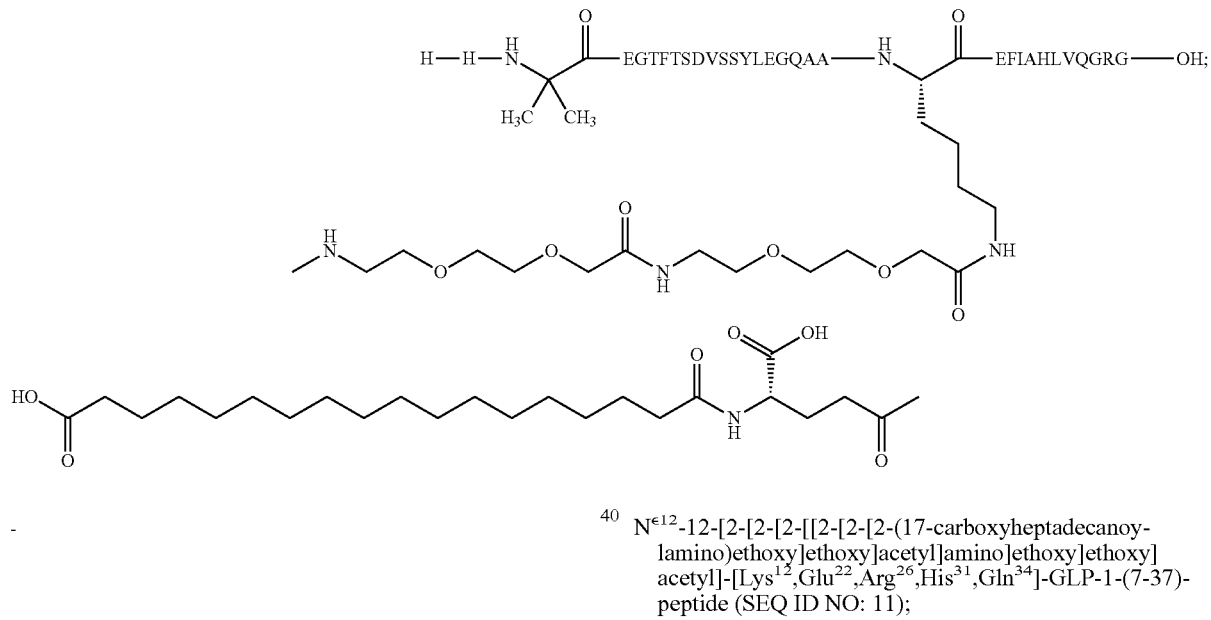

$N^{\epsilon 12}$-12-[2-[2-[2-[[2-[2-[2-(17-carboxyheptadecanoylamino)ethoxy]ethoxy]acetyl]amino]ethoxy]ethoxy]acetyl]-[Lys$^{12}$,Glu$^{22}$,Arg$^{26}$,His$^{31}$,Gln$^{34}$]-GLP-1-(7-37)-peptide (SEQ ID NO: 11);

Chem. 46

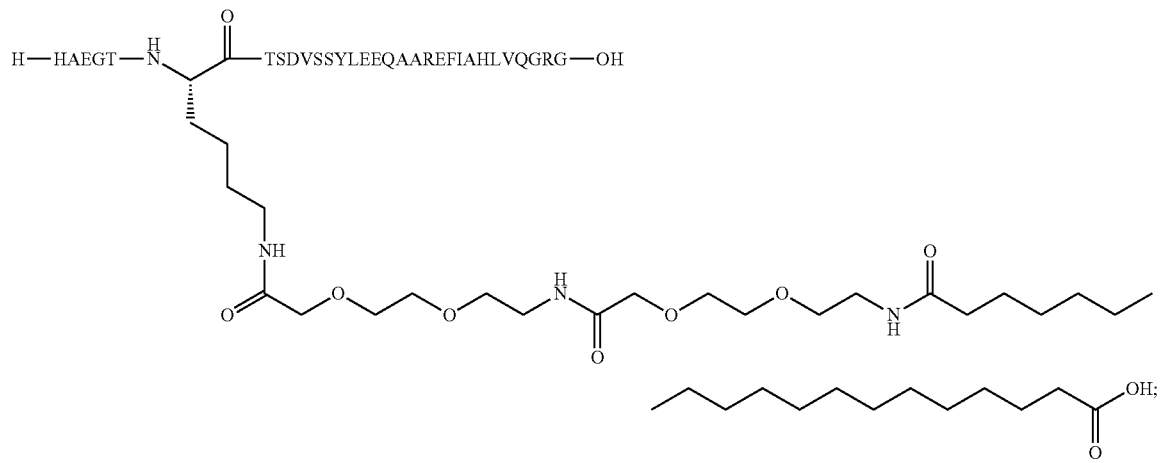

$N^{\epsilon 26}$-[2-(2-[2-(2-[2-(2-[4-(10-(4-Carboxyphenoxy)de- canoylamino)-4(S)-carboxybutyrylamino]ethoxy)ethoxy] acetylamino)ethoxy]ethoxy)acetyl]-$N^{\epsilon 37}$-[2-(2-[2-(2-[2-(2- [4-(10-(4-Carboxyphenoxy)decanoylamino)-4(S)- carboxybutyrylamino]ethoxy)ethoxy]acetylamino) ethoxy] ethoxy)acetyl][Aib$^8$,His$^{31}$,Gln$^{34}$,Lys$^{37}$]GLP-1(7-37)- peptide (SEQ ID NO: 8);

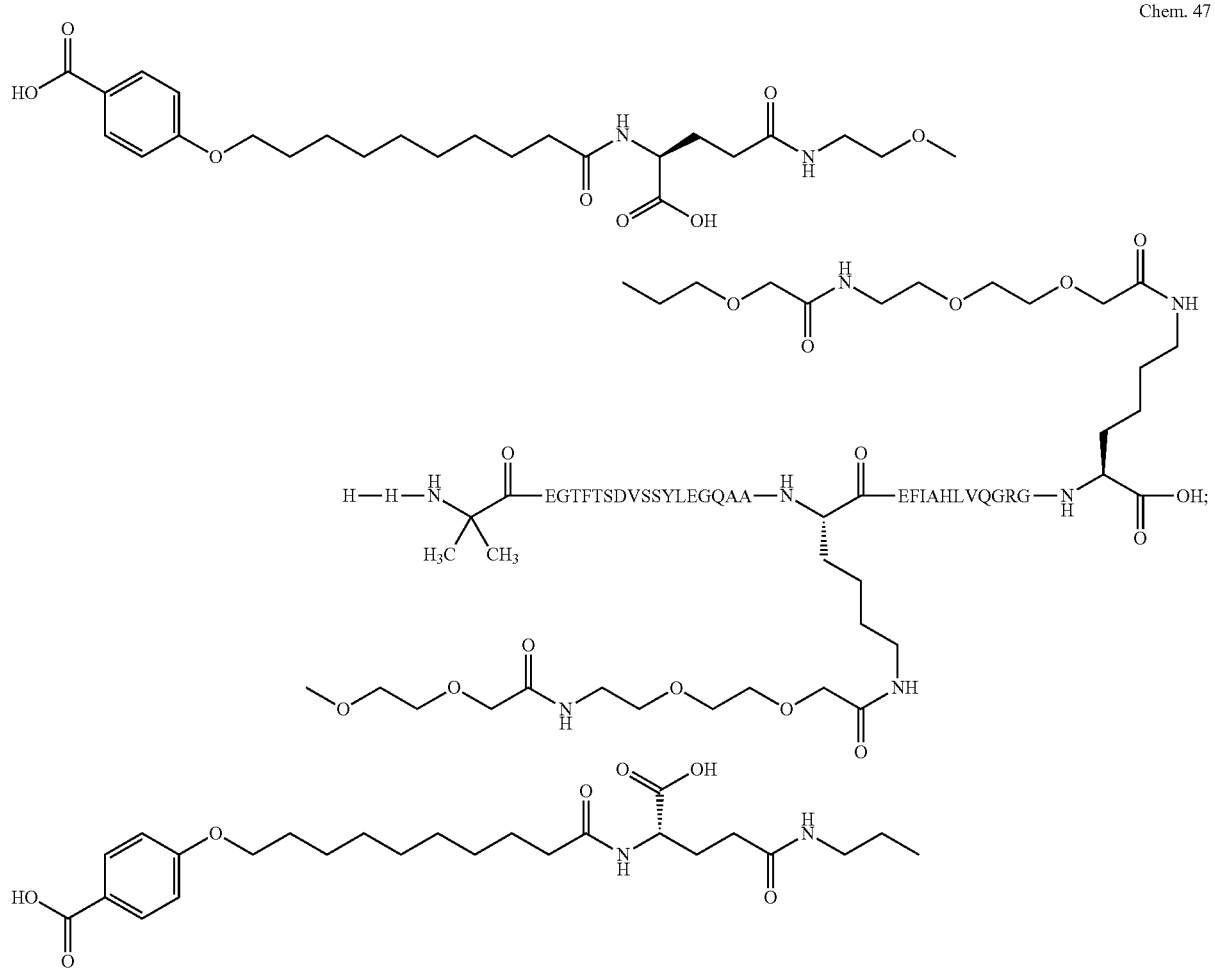

Chem. 47

$N^{\epsilon 26}$[2-(2-{2-[2-(2-{2-[(S) 4-Carboxy-4-(17-carboxyhepta- decanoylamino)butyrylamino]ethoxy}ethoxy)acety- lamino]ethoxy}ethoxy)acetyl][Ser$^8$,His$^{31}$,Gln$^{34}$] GLP-1 (7-37)-peptide (SEQ ID NO: 16);

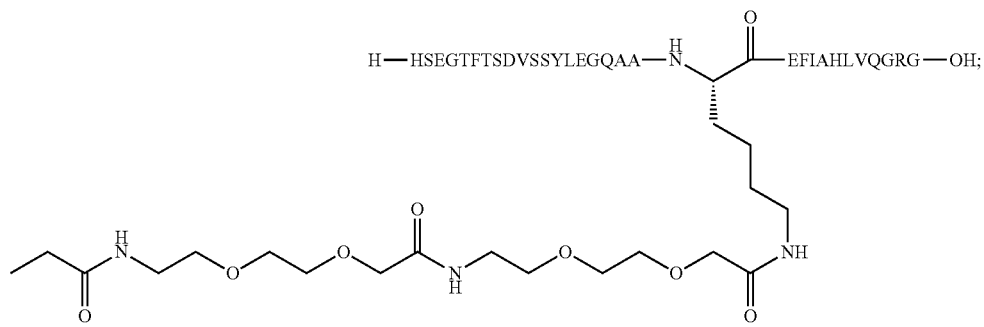

Chem. 32

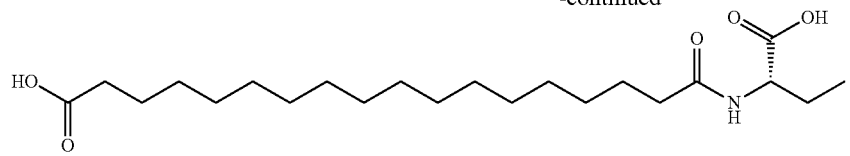
$N^{\epsilon 26}$ [2-(2-(2-{2-[(S)-4-Carboxy-4-(15-carboxypentadecanoylamino)butyrylamino]ethoxy}ethoxy)acetyl][Aib$^8$, His$^{31}$,Gln$^{34}$]GLP-1(7-37)-peptide (SEQ ID NO: 4):
Chem. 35
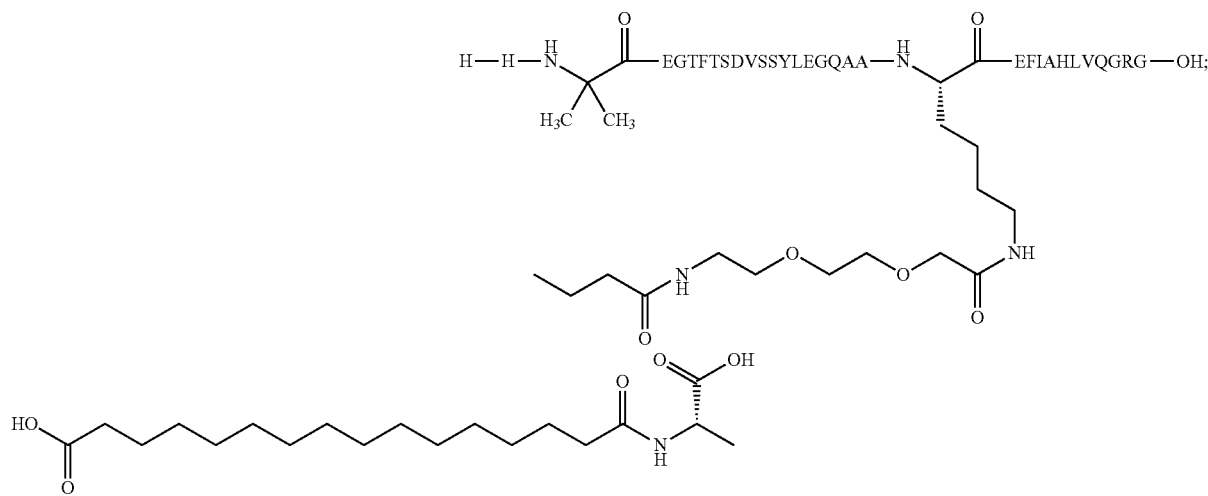
$N^{\epsilon 26}$[2-(2-{2-[(S)-4-Carboxy-4-(2-{2-[2-(17-carboxy-heptadecanoylamino)ethoxy]ethoxy}acetylamino)butyrylamino]ethoxy}ethoxy)acetyl] [Aib$^8$,His$^{31}$,Gln$^{34}$]GLP-1(7-37)-peptide (SEQ ID NO: 4);
Chem. 38
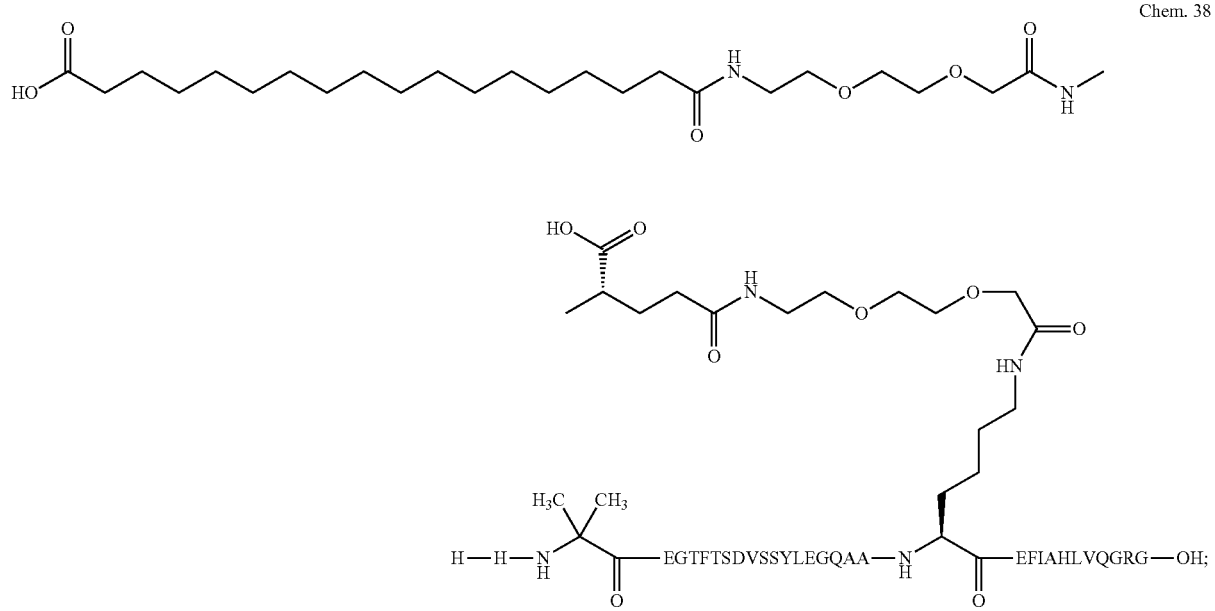

$N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 37}$-[(4S)-4-carboxy-4-    [[2-[2-[2-[[2-[2-[2-[10-(4-carboxyphenoxy) decanoylamino]ethoxy]ethoxy]acetyl]amino]ethoxy]ethoxy]acetyl]amino]butanoyl][His$^{31}$,Gln$^{34}$,Lys$^{37}$]-GLP-1-(7-37)-peptide (SEQ ID NO: 20);

Chem. 56

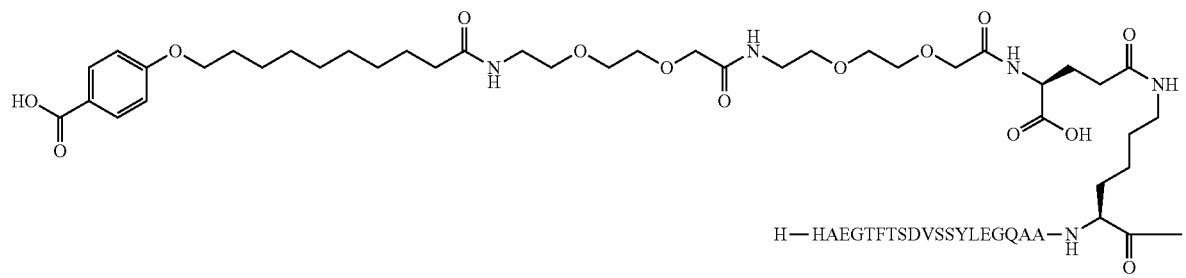

$N^{\epsilon 24}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$,Glu$^{22}$,Lys$^{24}$, Arg$^{26}$,His$^{31}$,Gln$^{34}$]-GLP-1-(7-37)-peptide (SEQ ID NO: 22);

Chem. 60

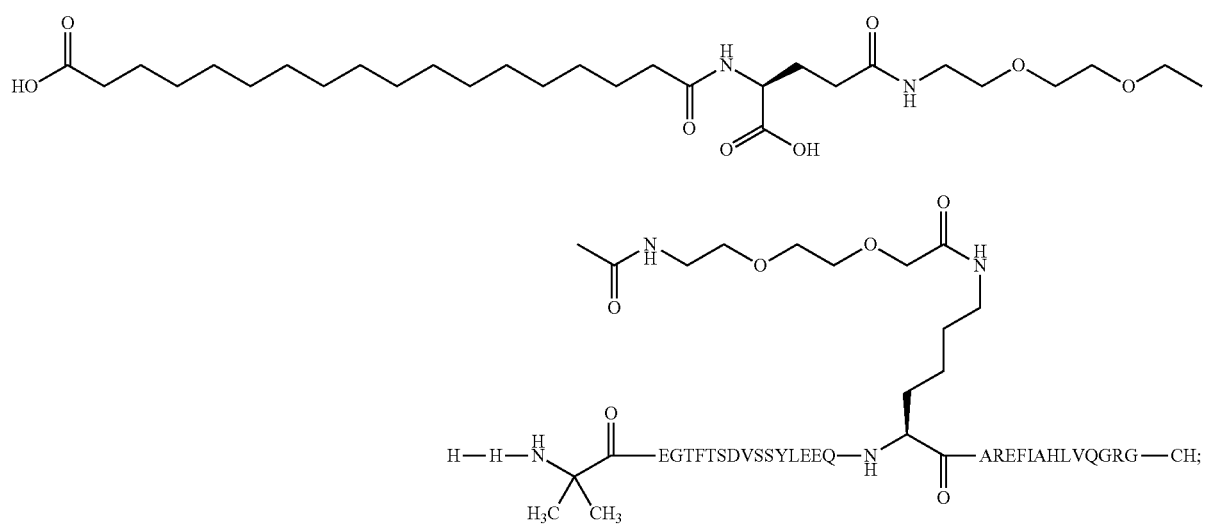

$N^{\epsilon 16}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$,Lys$^{16}$,Glu$^{22}$, Arg$^{26}$,His$^{31}$,Gln$^{34}$]-GLP-1-(7-37)-peptide (SEQ ID NO: 24);

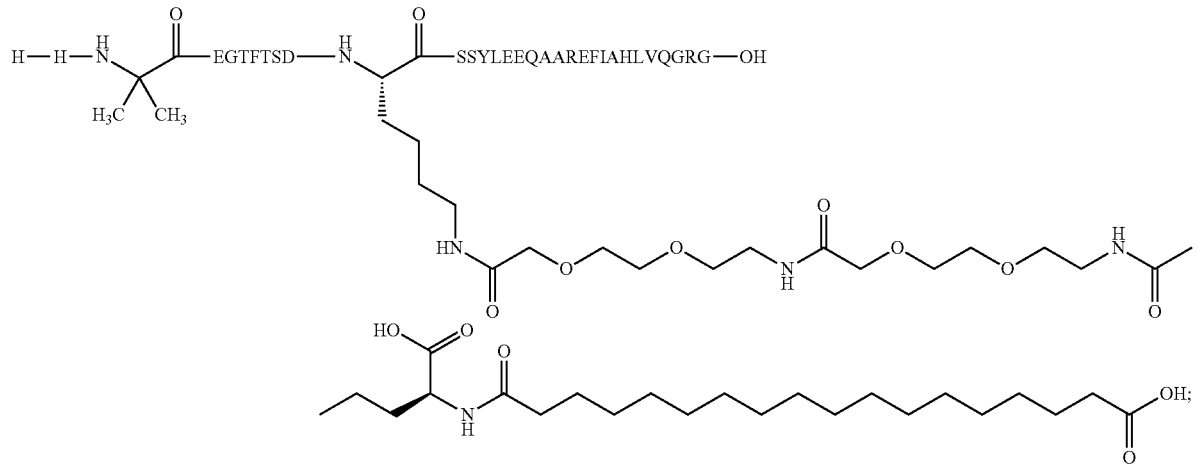

Chem. 62

$N^{\epsilon12}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Lys$^{12}$,Glu$^{22}$,Arg$^{26}$, His$^{31}$,Gln$^{34}$]-GLP-1-(7-37)-peptide (SEQ ID NO: 11); and

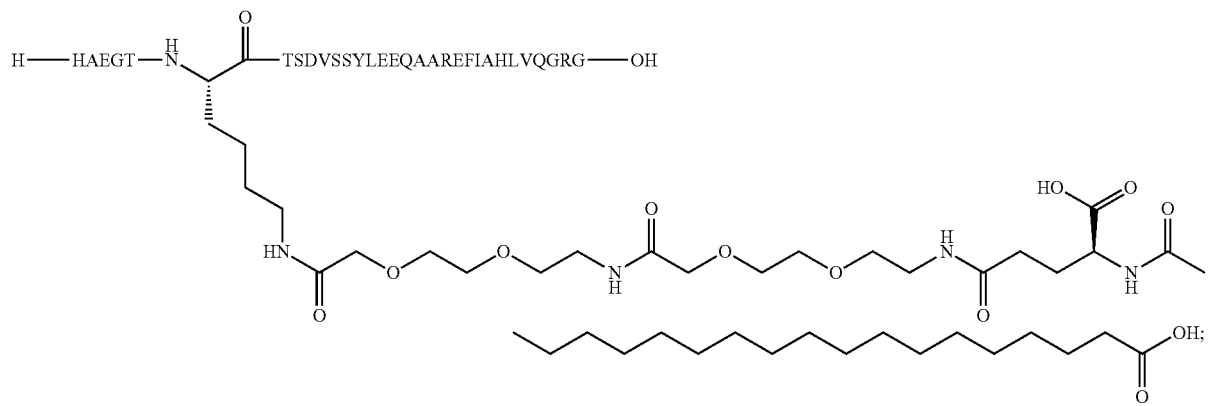

Chem. 65

152. The derivative of any one of embodiments 85-150, which is selected from the following:
$N^{\epsilon26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib$^8$,His$^{31}$,Gln$^{34}$]GLP-1 (7-37)-peptide (SEQ ID NO: 4);

Chem. 21

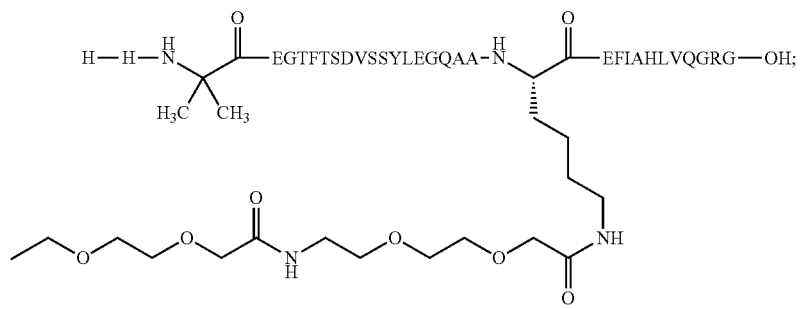

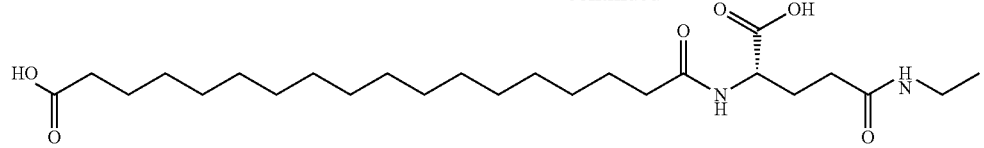

N$^{\epsilon 12}$-12-[2-[2-[2-[[2-[2-[2-(17-carboxyheptadecanoyl-
amino)ethoxy]ethoxy]acetyl]amino]ethoxy]ethoxy]
acetyl]-[Lys$^{12}$,Glu$^{22}$,Arg$^{26}$,His$^{31}$,Gln$^{34}$]-GLP-1-(7-37)-
peptide (SEQ ID NO: 11);

Chem. 46

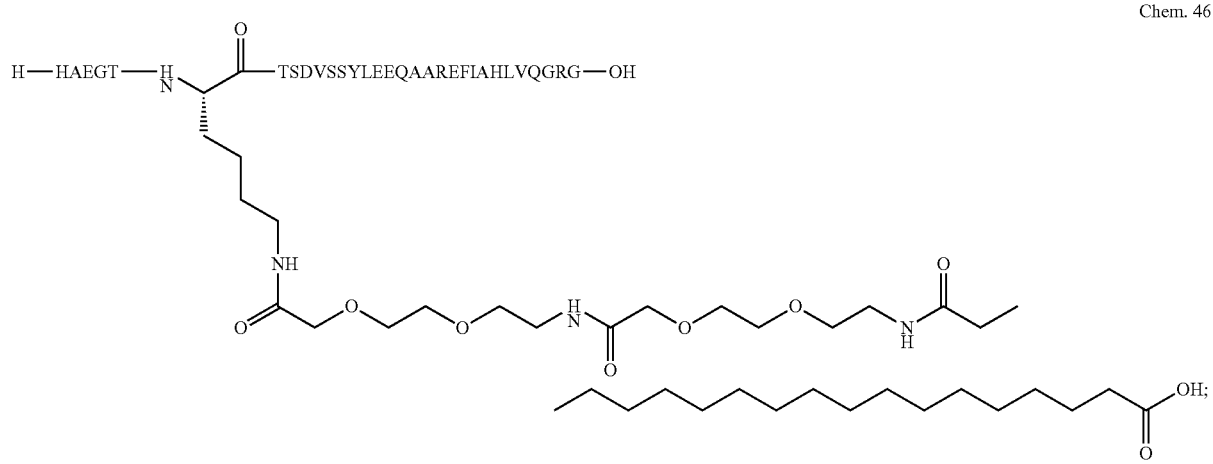

N$^{\epsilon 26}$[2-(2-{2-[(S)-4-Carboxy-4-(2-{2-[2-(17-carboxy-hep-
tadecanoylamino)ethoxy]ethoxy}acetylamino)butyryl
amino]ethoxy}ethoxy)acetyl] [Aib$^{8}$,His$^{31}$,Gln$^{34}$]GLP-1
(7-37)-peptide (SEQ ID NO: 4);

Chem. 38

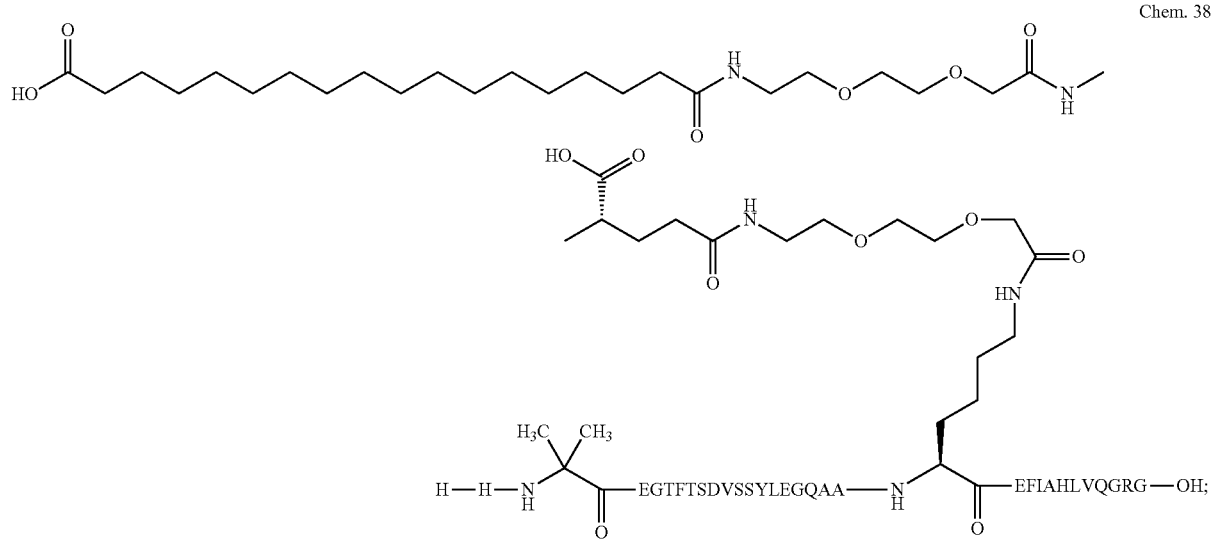

N$^{\epsilon 24}$-[2-[2-[2-[[2-[2-[2-[[(4S)-4-carboxy-4-(17-carboxy-
heptadecanoylamino)butanoyl]amino]ethoxy]ethoxy]
acetyl]amino]ethoxy]ethoxy]acetyl]-[Aib$^{8}$,Glu$^{22}$,Lys$^{24}$,
Arg$^{26}$,His$^{31}$,Gln$^{34}$]-GLP-1-(7-37)-peptide (SEQ ID NO:
22);

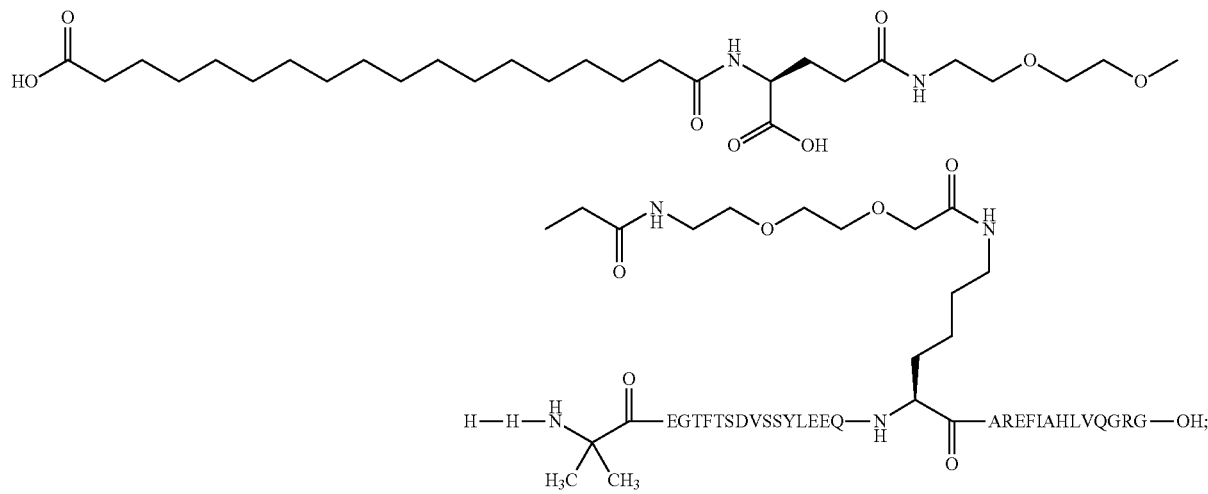

N$^{\epsilon16}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Aib$^8$,Lys$^{16}$,Glu$^{22}$, Arg$^{26}$,His$^{31}$,Gln$^{34}$]-GLP-1-(7-37)-peptide (SEQ ID NO: 24);

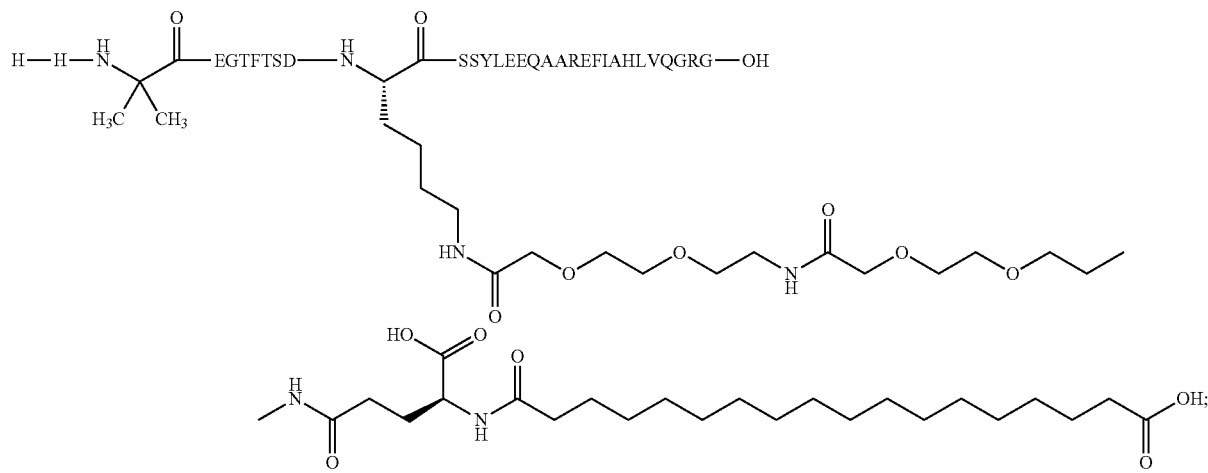

N$^{\epsilon12}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Lys$^{12}$,Glu$^{22}$,Arg$^{26}$, His$^{31}$,Gln$^{34}$]-GLP-1-(7-37)-peptide (SEQ ID NO: 11); and

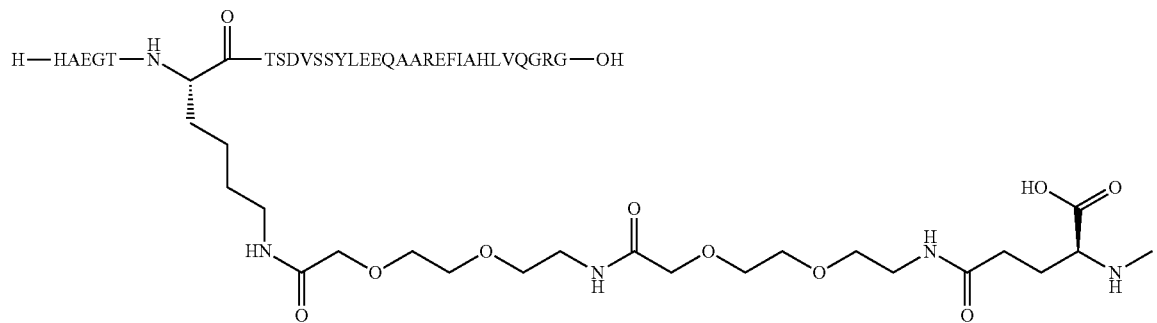

-continued

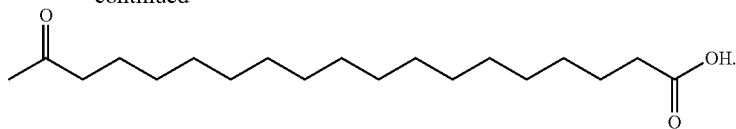

153. The derivative of any one of embodiments 85-150, which is selected from the following:
N$^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib$^8$,His$^{31}$,Gln$^{34}$]GLP-1(7-37)-peptide (SEQ ID NO: 4);

Chem. 21

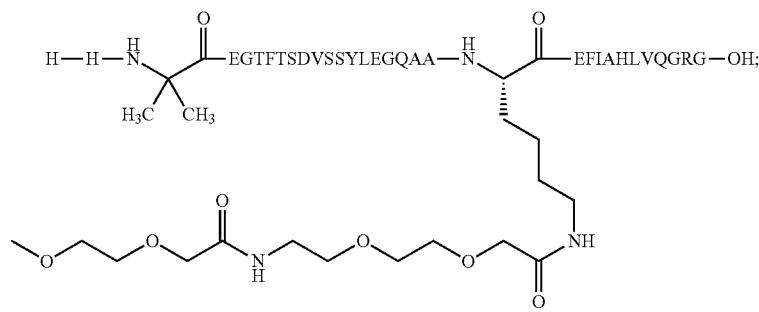

N$^{\epsilon 26}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl]-N$^{\epsilon 37}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl][Aib$^8$,His$^{31}$,Gln$^{34}$,Lys$^3$]GLP-1(7-37)-peptide (SEQ ID NO: 8);

Chem. 47

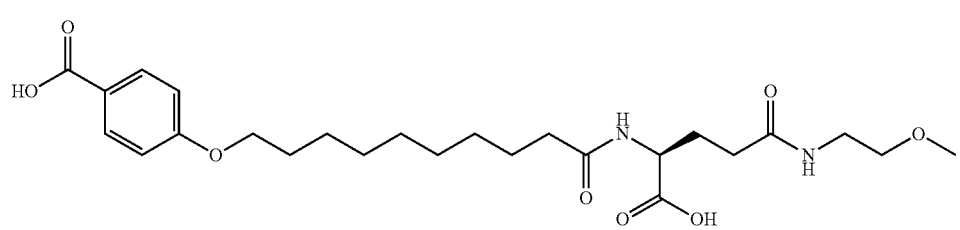

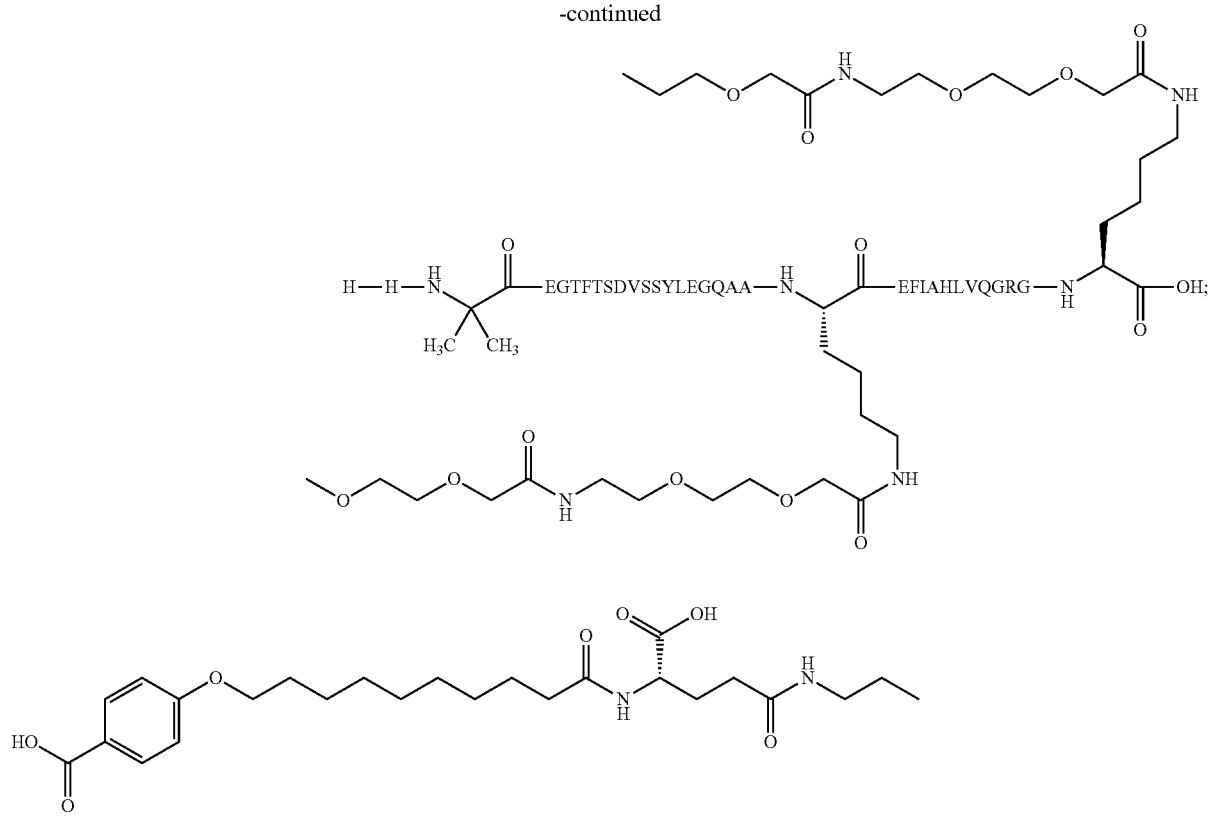
$N^{\epsilon 26}$[2-(2-{2-[2-(2-{2-[(S) 4-Carboxy-4-(17-carboxyhepta-decanoylamino)butyrylamino]ethoxy}ethoxy)acetylamino]ethoxy}ethoxy)acetyl] [Ser⁸,His³¹,Gln³⁴] GLP-1 (7-37)-peptide (SEQ ID NO: 16);
Chem. 32
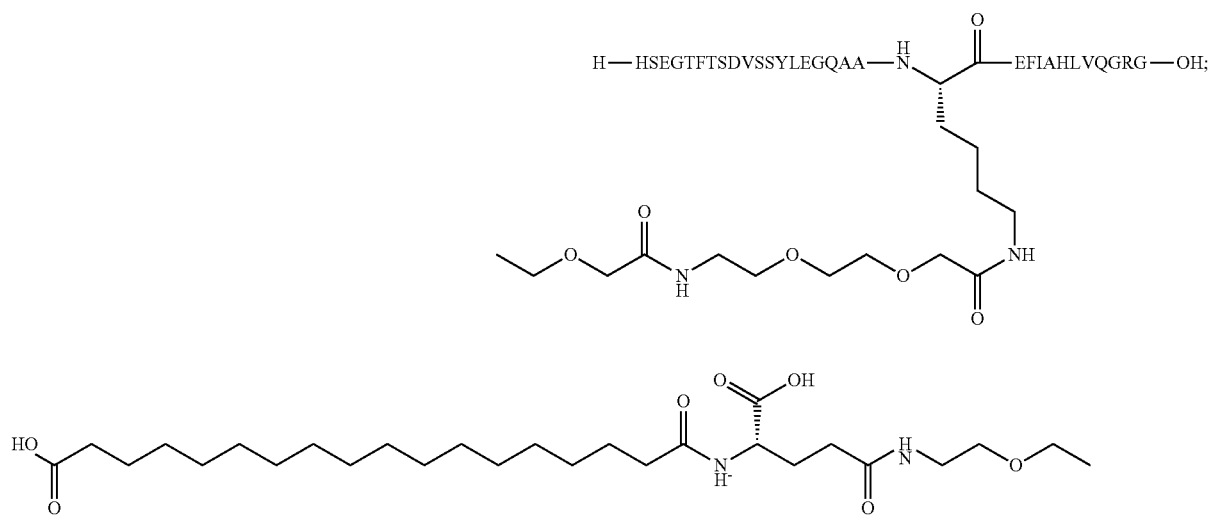
$N^{\epsilon 26}$[2-(2-{2-[(S)-4-Carboxy-4-(2-{2-[2-(17-carboxy-heptadecanoylamino)ethoxy]ethoxy}acetylamino)butyryl amino]ethoxy}ethoxy)acetyl] [Aib⁸,His³¹,Gln³⁴]GLP-1 (7-37)-peptide (SEQ ID NO: 4); and

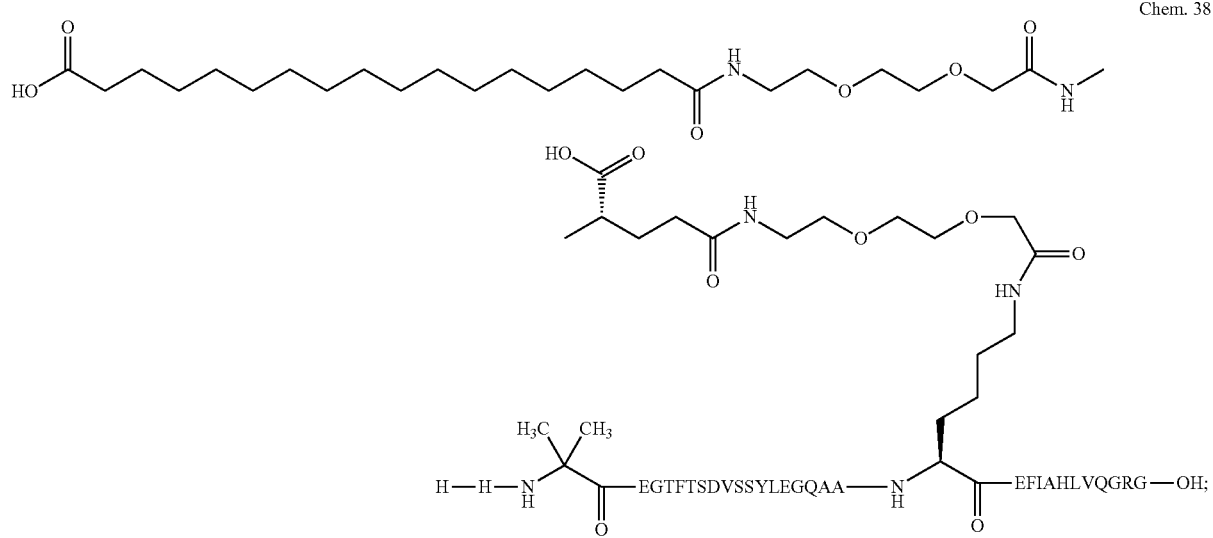
Chem. 38
preferably selected from
N^ε26[2-(2-{2-[2-(2-{2-[(S) 4-Carboxy-4-(17-carboxyhepta-decanoylamino)butyrylamino]ethoxy}ethoxy)acety-lamino]ethoxy}ethoxy)acetyl] [Ser⁸,His³¹,Gln³⁴] GLP-1 (7-37)-peptide (SEQ ID NO: 16);
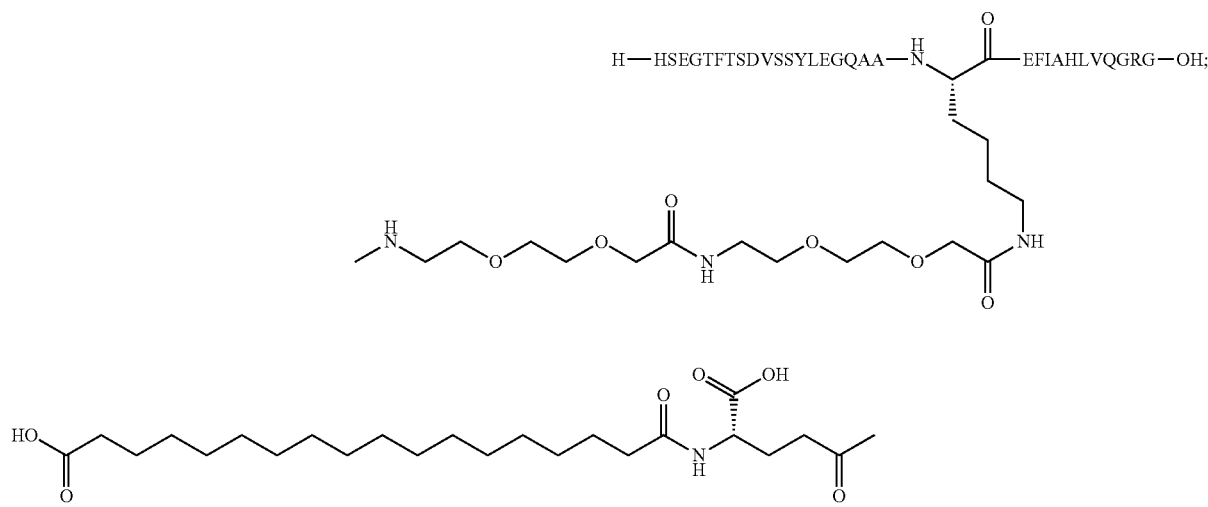
Chem. 32
and
N^ε26-[2-(2-{2-[2-(2-{2-[(S)-4-Carboxy-4-(17-carboxyhep-tadecanoylamino)butyrylamino]ethoxy}ethoxy)acety-lamino]ethoxy}ethoxy)acetyl][Aib⁸,His³¹,Gln³⁴]GLP-1 (7-37)-peptide (SEQ ID NO: 4);
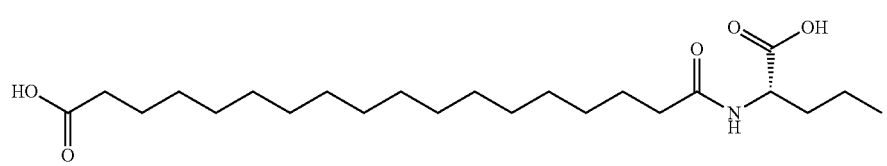
Chem 21

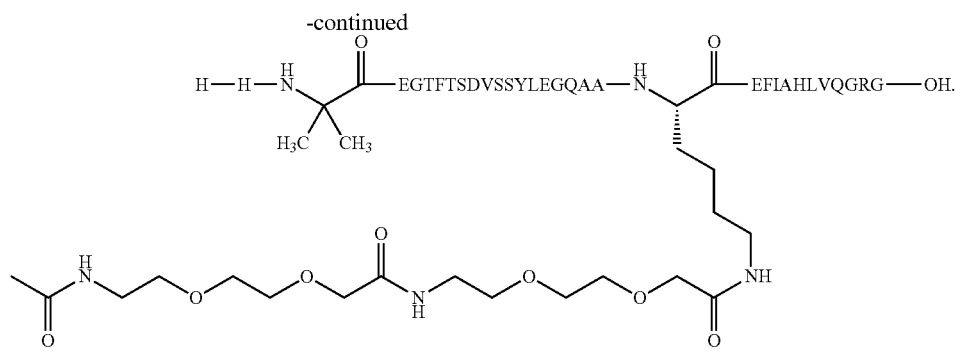

154. The derivative of any one of embodiments 151-153, which is Chem. 21, or a pharmaceutically acceptable salt, amide, or ester thereof.
155. The derivative of any one of embodiments 151-153, which is Chem. 32, or a pharmaceutically acceptable salt, amide, or ester thereof.
156. The derivative of any one of embodiments 151-153, which is Chem. 35, or a pharmaceutically acceptable salt, amide, or ester thereof.
157. The derivative of any one of embodiments 151-153, which is Chem. 38, or a pharmaceutically acceptable salt, amide, or ester thereof.
158. The derivative of any one of embodiments 151-153, which is Chem. 46, or a pharmaceutically acceptable salt, amide, or ester thereof.
159. The derivative of any one of embodiments 151-153, which is Chem. 47, or a pharmaceutically acceptable salt, amide, or ester thereof.
160. The derivative of any one of embodiments 151-153, which is Chem. 56, or a pharmaceutically acceptable salt, amide, or ester thereof.
161. The derivative of any one of embodiments 151-153, which is Chem. 60, or a pharmaceutically acceptable salt, amide, or ester thereof.
162. The derivative of any one of embodiments 151-153, which is Chem. 62, or a pharmaceutically acceptable salt, amide, or ester thereof.
163. The derivative of any one of embodiments 151-153, which is Chem. 65, or a pharmaceutically acceptable salt, amide, or ester thereof.
164. The analogue or derivative of any one of embodiments 1-163, which has GLP-1 activity.
165. The analogue or derivative of embodiment 164, wherein GLP-1 activity refers to the capability of activating the human GLP-1 receptor.
166. The analogue or derivative of embodiment 165, wherein activation of the human GLP-1 receptor is measured in an in vitro assay, as the potency of cAMP production.
167. The analogue or derivative of any one of embodiments 1-166, which has a potency corresponding to an $EC_{50}$ at or below 4500 pM, preferably below 4500 pM, more preferably below 4000 pM, even more preferably below 3500 pM, or most preferably below 3000 pM.
168. The analogue or derivative of any one of embodiments 1-167, which has a potency corresponding to an $EC_{50}$ below 2500 pM, preferably below 2000 pM, more preferably below 1500 pM, even more preferably below 1000 pM, or most preferably below 800 pM.
169. The analogue or derivative of any one of embodiments 1-168 which has a potency corresponding to an $EC_{50}$ below 600 pM, preferably below 500 pM, more preferably below 400 pM, even more preferably below 300 pM, or most preferably below 200 pM.
170. The analogue or derivative of any one of embodiments 1-169 which has a potency corresponding to an $EC_{50}$ below 180 pM, preferably below 160 pM, more preferably below 140 pM, even more preferably below 120 pM, or most preferably below 100 pM.
171. The analogue or derivative of any one of embodiments 1-170 which has a potency corresponding to an $EC_{50}$ below 80 pM, preferably below 60 pM, more preferably below 50 pM, even more preferably below 40 pM, or most preferably below 30 pM.
172. The analogue or derivative of any one of embodiments 1-171, wherein the potency is determined as $EC_{50}$ for the dose-response curve showing dose-dependent formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 48.
173. The analogue or derivative of any one of embodiments 1-172, the $EC_{50}$ of which is less than 10 times the $EC_{50}$ of semaglutide, preferably less than 8 times the $EC_{50}$ of semaglutide, more preferably less than 6 times the $EC_{50}$ of semaglutide, even more preferably less than 4 times the $EC_{50}$ of semaglutide, or most preferably less than 2 times the $EC_{50}$ of semaglutide.
174. The analogue or derivative of any one of embodiments 1-173, the $EC_{50}$ of which is less than the $EC_{50}$ of semaglutide, preferably less than 0.8 times the $EC_{50}$ of semaglutide, more preferably less than 0.6 times the $EC_{50}$ of semaglutide, even more preferably less than 0.4 times the $EC_{50}$ of semaglutide, or most preferably less than 0.2 times the $EC_{50}$ of semaglutide.
175. The analogue or derivative of any one of embodiments 1-174, the $EC_{50}$ of which is less than 10 times the $EC_{50}$ of liraglutide, preferably less than 8 times the $EC_{50}$ of liraglutide, more preferably less than 6 times the $EC_{50}$ of liraglutide, even more preferably less than 4 times the $EC_{50}$ of liraglutide, or most preferably less than 2 times the $EC_{50}$ of liraglutide.
176. The analogue or derivative of any one of embodiments 1-175, the $EC_{50}$ of which is less than the $EC_{50}$ of liraglutide, preferably less than 0.8 times the $EC_{50}$ of liraglutide, more preferably less than 0.6 times the potency of liraglutide, even more preferably less than 0.5 times the $EC_{50}$ of liraglutide, or most preferably less than or at 0.4 times the $EC_{50}$ of liraglutide.

177. The derivative of any one of embodiments 85-176, for which the ratio [GLP-1 receptor binding affinity ($IC_{50}$) in the presence of 2.0% HSA (high albumin), divided by GLP-1 receptor binding affinity ($IC_{50}$) in the presence of 0.005% HSA (low albumin)] is:
a) at least 0.5, preferably at least 1.0, more preferably at least 10, even more preferably at least 20, or most preferably at least 30;
b) at least 40, preferably at least 50, more preferably at least 60, even more preferably at least 70, or most preferably at least 80;
c) at least 90, preferably at least 100, more preferably at least 200, still more preferably at least 300, even more preferably at least 400, or most preferably at least 500;
d) at least 600, preferably at least 700, more preferably at least 800, even more preferably at least 1000, or most preferably at least 1300;
e) at least 20% of the ratio of semaglutide, preferably at least 50% of the ratio of semaglutide, more preferably at least 75% of the ratio of semaglutide, even more preferably at least equal to the ratio of semaglutide, or most preferably at least twice the ratio of semaglutide; or
f) at least equal to the ratio of liraglutide, preferably at least twice the ratio of liraglutide, more preferably at least three times the ratio of liraglutide, even more preferably at least 5 times the ratio of liraglutide, or most preferably at least 10 times the ratio of liraglutide.

178. The analogue or derivative of any one of embodiments 1-177, for which the GLP-1 receptor binding affinity ($IC_{50}$) in the presence of 0.005% HSA (low albumin) is
a) below 600.00 nM, preferably below 500.00 nM, more preferably below 200.00 nM, even more preferably below 100.00 nM, or most preferably below 50.00 nM; or
b) below 20.00 nM, preferably below 10.00 nM, more preferably below 5.00 nM, even more preferably below 2.00 nM, or most preferably below 1.00 nM.

179. The derivative of any one of embodiments 85-178, for which the GLP-1 receptor binding affinity ($IC_{50}$) in the presence of 2.0% HSA (high albumin) is
a) at or below 1000.00 nM, preferably below 900 nM, more preferably below 800 nM, even more preferably below 700 nM, or most preferrably below 600 nM; or
b) below 400.00 nM, preferably below 300.00 nM, more preferably below 200.00 nM, even more preferably below 100.00 nM, or most preferably below 50.00 nM.

180. The analogue or derivative of any one of embodiments 1-179, wherein the binding affinity to the GLP-1 receptor is measured by way of displacement of $^{125}$I-GLP-1 from the receptor, preferably using a SPA binding assay.

181. The analogue or derivative of any one of embodiments 1-180, wherein the GLP-1 receptor is prepared using a stable, transfected cell line, preferably a hamster cell line, more preferably a baby hamster kidney cell line, such as BHK tk-ts13.

182. The analogue or derivative of any one of embodiments 1-181, wherein the $IC_{50}$ value is determined as the concentration which displaces 50% of $^{125}$I-GLP-1 from the receptor.

183. The derivative of any one of embodiments 85-182, which has an oral bioavailability, preferably an absolute oral bioavailability, which is higher than that of liraglutide; and/or higher than that of semaglutide.

184. The derivative of embodiment 183, wherein oral bioavailability is measured in vivo in rats, as exposure in plasma after direct injection into the intestinal lumen.

185. The derivative of any one of embodiments 85-184, for which the plasma concentration (pM) of the derivative, determined 30 minutes after injection of a solution of the derivative in the jejunum of rat, divided by the concentration (pM) of the injected solution (dose-corrected exposure at 30 min) is at least 15, preferably at least 30, more preferably at least 48, still more preferably at least 62, even more preferably at least 80, or most preferably at least 100.

186. The derivative of any one of embodiments 85-185, for which the plasma concentration (pM) of the derivative, determined 30 minutes after injection of a solution of the derivative in the jejunum of rat, divided by the concentration (pM) of the injected solution (dose-corrected exposure at 30 min) is at least 110, preferably at least 120, more preferably at least 130, still more preferably at least 140, even more preferably at least 150, or most preferably at least 160.

187. The derivative of any one of embodiments 85-186, for which the plasma concentration (pM) of the derivative, determined 30 minutes after injection of a solution of the derivative in the jejunum of rat, divided by the concentration (μM) of the injected solution (dose-corrected exposure at 30 min) is at least 180, preferably at least 210, more preferably at least 240, or most preferably at least 280.

188. The derivative of any one of embodiments 85-187, wherein the GLP-1 derivative is tested in a concentration of 1000 uM in admixture with 55 mg/ml sodium caprate.

189. The derivative of any one of embodiments 85-188, wherein male Sprague Dawley rats are used, preferably with a body weight upon arrival of approximately 240 g.

190. The derivative of any one of embodiments 85-189, wherein the rats are fasted for approximately 18 hours before the experiment.

191. The derivative of any one of embodiments 85-190, wherein the rats are taken into general anaesthesia after having fasted and before the injection of the derivative in the jejunum.

192. The derivative of any one of embodiments 85-191, wherein the derivative is administered in the proximal part of the jejunum (10 cm distal for the duodenum) or in the mid-intestine (50 cm proximal for the cecum).

193. The derivative of any one of embodiments 85-192, wherein 100 μl of the derivative is injected into the jejunal lumen through a catheter with a 1 ml syringe, and subsequently 200 μl of air is pushed into the jejunal lumen with another syringe, which is then left connected to the catheter to prevent flow back into the catheter.

194. The derivative of any one of embodiments 85-193, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

195. The derivative of any one of embodiments 85-194, wherein plasma (75 ul) is separated, immediately frozen, and kept at −20° C. until analyzed for plasma concentration of the derivative.

196. The derivative of any one of embodiments 85-195, wherein LOCI (Luminescent Oxygen Channeling Immunoassay) is used for analyzing the plasma concentration of the derivative.

197. The analogue or derivative of any one of embodiments 1-196, which is effective at lowering blood glucose in vivo in db/db mice.

198. The analogue or derivative of any one of embodiments 1-197, which is effective at lowering body weight in vivo in db/db mice.

199. The analogue or derivative of any one of embodiments 1-198, wherein db/db mice are treated, s.c., with a suitable range of doses of the GLP-1 analogue or derivative, and blood glucose and/or bodyweight is/are determined at appropriate intervals.

200. The analogue or derivative of embodiment 199, wherein the dose of the GLP-1 analogue or derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

201. The analogue or derivative of any one of embodiments 197-200, wherein a control group is treated with vehicle, s.c., preferably the medium in which the GLP-1 analogue or derivative is dissolved, e.g. with the following composition: 50 mM sodium phosphate, 145 mM sodium chloride, 0.05% TWEEN™ polysorbate 80, pH 7.4.

202. The analogue or derivative of any one of embodiments 197-201, wherein blood glucose is determined, and/or the mice are weighed, at time–½h (half an hour prior to dosing (t=0)), and at times 1, 2, 4, 8, 24, 48, 72, and 96 h.

203. The analogue or derivative of any one of embodiments 197-202, wherein the glucose concentration is measured using the glucose oxidase method.

204. The analogue or derivative of any one of embodiments 197-203, wherein
(i) $ED_{50}$ (body weight (BW)) is calculated as the dose giving rise to half-maximum effect on delta (e.g., decrease) BW 24 hours following the subcutaneous administration of the analogue or derivative; and/or
(ii) $ED_{50}$ (blood glucose (BG)) is calculated as the dose giving rise to half-maximum effect on AUC (Area Under the Curve) delta (e.g., decrease) BG 8 hours following the subcutaneous administration of the analogue or derivative.

205. The analogue or derivative of any one of embodiments 197-204, wherein a sigmoidal dose-response relationship exists, preferably with a clear definition of the maximum response.

206. The derivative of any one of embodiments 85-205, which has a more protracted profile of action than liraglutide.

207. The derivative of embodiment 206, wherein protraction means half-life in vivo in a relevant animal species, such as db/db mice, rat, pig, and/or, preferably, minipig; wherein the derivative is administered i) s.c., and/or, preferably, ii) s.c.

208. The derivative of any one of embodiments 206-207, wherein the terminal half-life ($T_{1/2}$) after i.v. administration in minipigs is
a) at least 12 hours, preferably at least 24 hours, more preferably at least 36 hours, even more preferably at least 48 hours, or most preferably at least 60 hours; or
b) at least 0.2 times the half-life of semaglutide, preferably at least 0.4 times the half-life of semaglutide, more preferably at least 0.6 times the half-life of semaglutide, even more preferably at least 0.8 times the half-life of semaglutide, or most preferably at least the same as the half-life of semaglutide.

209. The derivative of any one of embodiments 207-208, wherein the minipigs are male Göttingen minipigs.

210. The derivative of any one of embodiments 207-209, wherein the minipigs are 7-14 months of age, and preferably weighing from 16-35 kg.

211. The derivative of any one of embodiments 207-210, wherein the minipigs are housed individually, and fed once or twice daily, preferably with SDS minipig diet.

212. The derivative of any one of embodiments 207-211, wherein the derivative is dosed, i.v., after at least 2 weeks of acclimatisation.

213. The derivative of any one of embodiments 207-212, wherein the animals are fasted for approximately 18 h before dosing and for at least 4 h after dosing, and have ad libitum access to water during the whole period.

214. The derivative of any one of embodiments 207-213, wherein the GLP-1 derivative is dissolved in 50 mM sodium phosphate, 145 mM sodium chloride, 0.05% TWEEN™ polysorbate 80, pH 7.4 to a suitable concentration, preferably from 20-60 nmol/ml.

215. The derivative of any one of embodiments 207-214, wherein intravenous injections of the derivative are given in a volume corresponding to 1-2 nmol/kg.

216. The analogue or derivative of any one of embodiments 1-215, which increases the glucose stimulated insulin secretion in minipigs.

217. The analogue or derivative of embodiment 216, wherein the minipigs are male Göttingen minipigs.

218. The analogue or derivative of any one of embodiments 216-217, wherein the minipigs are 7-14 months of age.

219. The analogue or derivative of any one of embodiments 216-218, wherein the minipigs are housed in single pens, and fed once or twice daily, preferably with SDS minipig fodder.

220. The analogue or derivative of any one of embodiments 216-219, wherein a single dose, optionally after a period with dose escalation, is given i.v., or s.c., in the thin skin behind the ear.

221. The analogue or derivative of any one of embodiments 216-220, wherein the animals are fasted for approximately 18 h before dosing.

222. The analogue or derivative of any one of embodiments 216-221, wherein a baseline group and a number of derivative dose groups corresponding to 2-6 different plasma concentration levels are tested, wherein the baseline group is a) vehicle treated, or b) untreated.

223. The analogue or derivative of any one of embodiments 216-222, wherein the plasma concentration level is 3000-80000 pM.

224. The analogue or derivative of any one of embodiments 216-223, wherein a 1 or 2 hour intravenous glucose tolerance test (IVGTT) is performed.

225. The analogue or derivative of any one of embodiments 216-224, wherein 0.3 g/kg glucose is given i.v. over a period of 30 seconds, and blood samples taken at suitable time points, such as the following time points (t=0 corresponds to the glucose bolus): −10, −5, 0, 2, 5, 10, 15, 20, 25, 30, 40, 50, 60, 70, 80, 90, 100, 110, 120 minutes.

226. The analogue or derivative of embodiment 225, wherein the concentration in plasma of the analogue or derivative, glucose, and insulin is determined.

227. The analogue or derivative of embodiment 226, wherein the analogue or derivative concentration is measured at t=0 min, and, optionally, at the end of the test (t=60 min, or t=120 min).

228. The analogue or derivative of any one of embodiments 216-227, wherein glucose is analysed using the glucose oxidase method.

229. The analogue or derivative of any one of embodiments 216-228, wherein the area under the insulin curve (AUCinsulin) is calculated and used as a measure of insulin secretion.

230. The analogue or derivative of any one of embodiments 216-229, wherein for at least one concentration thereof, the AUCinsulin is higher than the baseline AUCinsulin, preferably at least 110% thereof, more preferably at least 120% thereof, even more preferably at least 130% thereof or most preferably at least 140% thereof.

231. The analogue or derivative of any one of embodiments 1-230, which causes a reduced feed intake in pigs relative to a control (preferably vehicle-treated, or untreated);
optionally the feed intake (0-24 h) may be 90% or lower relative to the vehicle-treated control, preferably 80% or lower, more preferably 70% or lower, even more preferably 60% or lower, or most preferably 50% or lower;
wherein feed intake (0-24 h) refers to the first 24 hours after administration of the derivative or vehicle.
232. The analogue or derivative of embodiment 231, wherein the pigs are female Landrace Yorkshire Duroc (LYD) pigs.
233. The analogue or derivative of embodiment 232, wherein the LYD pigs are 3 months of age, and preferably have a weight of 30-35 kg.
234. The analogue or derivative of any one of embodiments 231-233, where the animals are housed in a group for 1-2 weeks for acclimatisation.
235. The analogue or derivative of any one of embodiments 231-234, wherein during the experimental period the animals are placed in individual pens from Monday morning to Friday afternoon for measurement of individual food intake.
236. The analogue or derivative of any one of embodiments 231-235, wherein the animals are fed ad libitum with pig fodder (such as Svinefoder, Antonio).
237. The analogue or derivative of any one of embodiments 231-236, wherein food intake is monitored on line by logging the weight of fodder every 15 minutes, preferably using the Mpigwin system.
238. The analogue or derivative of any one of embodiments 231-237, which is dosed 0.3, 1.0, 3.0, 10, or 30 nmol/kg, preferably dissolved in a phosphate buffer (50 mM phosphate, 0.05% TWEEN™ polysorbate 80, pH 8), more preferably at concentrations of 12, 40, 120, 400, or 1200 nmol/ml.
239. The analogue or derivative of any one of embodiments 231-238, wherein the phosphate buffer serves as vehicle.
240. The analogue or derivative of any one of embodiments 231-239, wherein the animals are dosed with a single subcutaneous dose of the derivative, or vehicle (preferably with a dose volume of 0.025 ml/kg), on the morning of day 1, and food intake is measured for 4 days after dosing.
241. The analogue or derivative of any one of embodiments 1-240, which has an in vitro half-life ($T_{1/2}$), in an extract of rat small intestines, divided by the corresponding half-life ($T_{1/2}$) of GLP-1(7-37), of at least 1.0, preferably at least 2.0, still more preferably at least 4.0, or most preferably at least 5.0.
242. The analogue or derivative of any one of embodiments 1-241, which has an in vitro half-life ($T_{1/2}$), in an extract of rat small intestines, divided by a corresponding half-life ($T_{1/2}$) of GLP-1(7-37), of at least 9.0, preferably at least 10.0, more preferably at least 12.0, even more preferably at least 14.0, still more preferably at least 16.0, or most preferably at least 18.0; or even at least 20.0.
243. The analogue or derivative of any one of embodiments 241-242, wherein the rat small intestine extract is prepared as described in Example 50, the analogue or derivative is incubated for one hour at 37° C., the concentration of the extract is titrated so that the half-life of GLP-1(7-37) is in the range of 10-20 minutes, e.g. 1.4 ug/ml, the resulting samples are analysed by UPLC and/or MALDI-TOF, and/or the incubation and analysis is performed as described in Example 50.
244. The analogue or derivative of any one of embodiments 241-243, for which a ratio [half-life ($T_{1/2}$) in vitro in rat small intestine extract, divided by a half-life ($T_{1/2}$) in vitro in rat small intestine extract of GLP-1(7-37)] is at least 0.5 times the corresponding ratio of semaglutide, preferably at least 2 times the ratio of semaglutide, more preferably at least 3 times the ratio of semaglutide, even preferably at least 5 times the ratio of semaglutide, or most preferably at least 7 times the ratio of semaglutide.
245. The analogue or derivative of any one of embodiments 241-244, for which a ratio [half-life ($T_{1/2}$) in rat small intestine extract, divided by a half-life ($T_{1/2}$) in rat small intestine extract of GLP-1(7-37)] is at least 0.1 times the corresponding ratio of liraglutide, preferably at least 0.4 times the ratio of liraglutide, more preferably at least 0.8 times the ratio of liraglutide, even more preferably at least 1.2 times the ratio of liraglutide, or most preferably at least 1.5 times the ratio of liraglutide.
246. The derivative of any one of embodiments 85-245, which has a half-life ($T_{1/2}$) in vivo in rats after i.v. administration of at least 4 hours, preferably at least 6 hours, even more preferably at least 8 hours, or most preferably at least 10 hours.
247. The derivative of any one of embodiments 85-246, which has a half-life ($T_{1/2}$) in vivo in rats after i.v. administration of at least 11 hours, preferably at least 12 hours, even more preferably at least 13 hours, or most preferably at least 14 hours.
248. The derivative of any one of embodiments 85-247, in which the rats are male Sprague Dawley rats with a body weight from 300 to 600 g.
249. The derivative of any one of embodiments 85-248, which has a half-life ($T_{1/2}$) in vivo in rats after i.v. administration which is at least the same as the half-life of semaglutide, preferably at least 2 times the half-life of semaglutide, more preferably at least 3 times the half-life of semaglutide, even more preferably at least 4 times the half-life of semaglutide, or most preferably at least 5 times the half-life of semaglutide.
250. The derivative of any one of embodiments 85-249, which has a relatively low binding affinity to HSA, preferably a lower binding affinity, and/or a higher $K_d$ (or $K_d$ apparent), than a) the compound of Example 68 WO 2009/030771; b) the compound of Example 69 of WO 2009/030771; and/or c) the compound of Example 71 of WO 2009/030771; wherein the binding affinity to HSA may be expressed as the dissociation constant ($K_d$, in μM); preferably as the apparent dissociation constant; and wherein, more preferably, the dissociation constant, or the apparent dissociation constant is
  i) at or above 1; preferably at or above 5; even more preferably at or above 10; or most preferably at or above 20;
  ii) at or below 25; preferably below 20; more preferably below 10; even more preferably below 5.0; or most preferably below 1.0; and/or
  iii) within a range defined by the limits of i) and ii), such as, e.g., between 1 and 5; between 1 and 10; between 1 and 20; between 1 and 25; between 5 and 10; between 5 and 20; between 5 and 25; between 10 and 20; or between 20 and 25.
251. The derivative of embodiment 250, wherein the dissociation constant is measured using a competition scintillation proximity assay (SPA), such as the one described in Example 57.
252. The derivative of any one of embodiments 250-251, wherein Streptavidin-SPA beads (such as GE Healthcare RPNQ0009) are incubated with biotinylated HSA for 5 hours
253. The derivative of embodiment 252, wherein the beads are washed, preferably with buffer, to remove unbound HSA; and subsequently mixed with a $^{125}$I-labeled acylated GLP-1 analogue (such as N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino)ethoxy]ethoxy)acetyl][Aib8,$^{125}$I-Tyr19, Glu22,Arg26,Arg34,Lys37] GLP-1(7-37)-NH$_2$) in a buffer containing 100 mM Hepes, 100 mM NaCl, 10 mM MgSO$_4$, 0.025% TWEEN™ polysorbate-20, pH 7.4.
254. The derivative of embodiment 253, wherein the reaction mixture is pipetted off, e.g. into the wells of a Perkin Elmer Optiplate-96 6005290, preferably 100 μl per well; and 100 μl of a dilution series of the GLP-1 derivative to be measured is then added in the same buffer.

255. The derivative of embodiment 254, wherein after 20 hours of gentle rocking at room temperature the plates are centrifuged and counted, e.g. on a TopCounter; following which bound cpm is plotted as a function of GLP-1 derivative concentration; and the $K_d$ and/or the apparent $K_d$ may be calculated as the molar concentration of the GLP-1 derivative in question, multiplied by the molar concentration of HSA, and divided by the molar concentration of GLP-1-HSA complex.
256. The analogue or derivative of any one of embodiments 1-255, which has a molecular mass below 80 kDa; preferably below 60 kDa, such as below 40 kDa; even more preferably below 20 kDa; still more preferably below 10 kDa; or most preferably below 6 kDa.
257. The derivative of any one of embodiments 85-256, which is not a compound of Example 18, preferably not Chem. 37.
258. The derivative of any one of embodiments 85-257, which is not a compound of Examples 28, 29, 34, 35, 36, and 37; preferably not Chem. 47, Chem. 48, Chem. 53, Chem. 54, Chem. 55, and Chem. 56.
259. An intermediate product comprising, preferably consisting of, a compound selected from the following:

Chem. 67

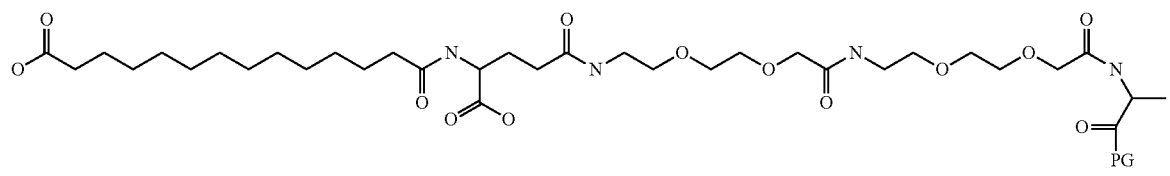

Chem. 68

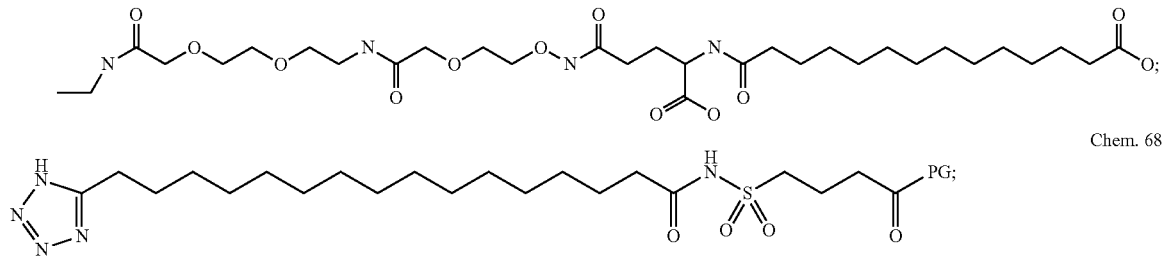

wherein PG represents a protection group, and
wherein, optionally, the distal *—COOH groups of the protracting moieties of Chem. 67 are also protected as is known in the art; preferably under the formation of a non-reactive ester; more preferably i) an ester of an alcohol with a bulky side chain, such as an ester of a phenol, optionally substituted; or ii) an ester of branched alkyl, preferably lower alkyl; most preferably protected as OtBu, OBz, and the like; or a pharmaceutically acceptable salt, amide, or ester thereof.
260. The intermediate product of embodiment 259, wherein PG is a group that reversibly renders the intermediate product unreactive, and that can be removed selectively.
261. The intermediate product of any one of embodiments 259-260, wherein PG is i) —OH, or ii) functionalised as an activated ester.
262. The intermediate product of embodiment 261, wherein the activated ester is an ester of p-nitrophenol; 2,4,5-trichlorophenol; N-hydroxysuccinimide; N-hydroxysulfosuccinimide; 3,4-dihydro-3-hydroxy-1,2,3-benzotriazine-4-one; 5-chloro-8-hydroxyquinoline; N-hydroxy-5-norbornene-2,3-dicarboxylic acid imide; pentafluorophenol; p-sulfotetrafluorophenol; N-hydroxyphthalimide; 1-hydroxybenzotriazole; 1-hydroxy-7-azabenzotriazole; N-hydroxymaleimide; 4-hydroxy-3-nitrobenzene sulfonic acid; or any other activated ester known in the art.
263. An analogue or a derivative according to any one of embodiments 1-258, for use as a medicament.
264. An analogue or a derivative according to any one of embodiments 1-258, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
265. Use of an analogue or a derivative according to any one of embodiments 1-258 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
266. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of an analogue or a derivative according to any one of embodiments 1-258.

EXAMPLES

This experimental part starts with a list of abbreviations, and is followed by a section including general methods for synthesising and characterising peptides and derivatives of the invention. Then follows a number of examples which relate to the preparation of specific GLP-1 peptide derivatives, and at the end a number of examples have been included relating to the activity and properties of these peptides and derivatives (section headed pharmacological methods).

The examples serve to illustrate the invention.

ABBREVIATIONS

The following abbreviations are used in the following, in alphabetical order:
Aib: aminoisobutyric acid (α-aminoisobutyric acid)
API: Active Pharmaceutical Ingredient
AUC: Area Under the Curve
BG: Blood Glucose
BHK Baby Hamster Kidney
Boc: t-butyloxycarbonyl
Bom: benzyloxymethyl
BW: Body Weight
Bzl: Benzyl
Clt: 2-chlorotrityl
collidine: 2,4,6-trimethylpyridine
cpm: counts per minute
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanic acid
OPfp: pentafluorophenoxy
OPnp: para-nitrophenoxy
OSu: 0-succinimidyl esters (hydroxysuccinimide esters)
OSuc: 2,5-dioxo-pyrrolidin-1-yl
OtBu: tert butyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl, or trityl
Trx: tranexamic acid
UPLC: Ultra Performance Liquid Chromatography Methods of Preparation A. General Methods This section relates to methods for synthesising resin bound peptide (SPPS methods, including methods for de-protection of amino acids, methods for cleaving the peptide from the resin, and for its purification), as well as methods for detecting and characterising the resulting peptide (LCMS, MALDI, and UPLC methods). The synthesis of the peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W.R. Sampson (1999), J. Pep. Sci. 5, 403). The protected amino acid derivatives used were standard Fmoc-amino acids (supplied from e.g. Anaspec, IRIS, or Novabiochem). The N-terminal amino acid was Boc protected at the alpha amino group (e.g. Boc-His(Boc)-OH, or Boc-His(Trt)-OH for peptides with His at the N-terminus). The epsilon amino group of lysines in the sequence were either protected with Mtt, Mmt, Dde, ivDde, or Boc, depending on the route for attachment of the albumin binding moiety and spacer. The albumin binding moiety and/or linker can be attached to the peptide either by acylation of the resin bound peptide or acylation in solution of the unprotected peptide. In case of attachment of the albumin binding moiety and/or linker to the protected peptidyl resin, the attachment can be modular using SPPS and suitably protected building blocks such as but not limited to Fmoc-OEG-OH (Fmoc-8-amino-3,6-dioxaoctanoic acid), Fmoc-Trx-OH (Fmoc-tranexamic acid), Fmoc-Glu-OtBu, octadecanedioic acid mono-tert-butyl ester, nonadecanedioic acid mono-tert-butyl ester, or 4-(9-carboxynonyloxy) benzoic acid tert-butyl ester.

1. Synthesis of Resin Bound Peptide
SPPS Method A

SPPS method A refers to the synthesis of a protected peptidyl resin using Fmoc chemistry on an Applied Biosystems 433 peptide synthesiser (also designated AB1433A synthesiser) in 0.25 mmol or 1.0 mmol scale using the manufacturer's FastMoc UV protocols which employ HBTU or HATU mediated couplings in NMP, and UV monitoring of the deprotection of the Fmoc protection group.

The starting resin used for the synthesis of peptide amides was a suitable Rink-Amide resin (for peptide amides), or (for peptides with a carboxy C-terminus) either a suitable Wang resin or a suitable chlorotrityl resin. Suitable resins are commercially available from, e.g., Novabiochem.

SPPS Method B

SPPS method B refers to the synthesis of a protected peptidyl resin using Fmoc chemistry on a microwave-based Liberty peptide synthesiser (CEM Corp., North Carolina). A suitable resin is a pre-loaded, low-load Wang resin available from Novabiochem (e.g. low load Fmoc-Lys(Mtt)-Wang resin, 0.35 mmol/g). Fmoc-deprotection was with 5% piperidine in NMP at up to 70 or 75° C. The coupling chemistry was DIC/HOAt in NMP. Amino acid/HOAt solutions (0.3 M in NMP at a molar excess of 3-10 fold) were added to the resin followed by the same molar equivalent of DIC (0.75M in NMP). For example, the following amounts of 0.3M amino acid/HOAt solution were used per coupling for the following scale reactions: Scale/ml, 0.10 mmol/2.5 ml, 0.25 mmol/5 ml, 1 mmol/15 ml. Coupling times and temperatures were generally 5 minutes at up to 70 or 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 min then heated to 70 or 75° C. for 5 min. Some amino acids were "double coupled", meaning that after the first coupling (e.g. 5 min at 75° C.), the resin is drained and more reagents are added (amino acid, HOAt and DIC), and the mixture in heated again (e.g. 5 min at 75° C.). When a chemical modification of a lysine side chain was desired, the lysine was incorporated as Lys(Mtt). The Mtt group was removed by washing the resin with DCM and suspending the resin in neat (undiluted) hexafluoroisopropanol for 20 minutes followed by washing with DCM and NMP. The chemical modification of the lysine was performed either by manual synthesis (see SPPS method D) or by one or more automated steps on the Liberty peptide synthesiser as described above, using suitably protected building blocks (see General methods), optionally including a manual coupling.

SPPS Method D

SPPS method D refers to synthesis of the protected peptidyl resin using manual Fmoc chemistry. This was typically used for the attachment of the linkers and side chains to the peptide backbone. The coupling chemistry was DIC/HOAt/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 mL). Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with neat hexafluroisopropanol (5×20 ml, each 10 min) followed by washings as above. The albumin binding moiety and/or linker can be attached to the peptide either by acylation of the resin bound peptide or acylation in solution of the unprotected peptide (see the routes described below). In case of attachment of the albumin binding moiety and/or linker to the protected peptidyl resin the attachment can be modular using SPPS and suitably protected building blocks (see General methods).

Attachment to Resin Bound Peptide—Route I:

Activated (active ester or symmetric anhydride) albumin binding moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, DCM, 2-propanol, methanol and diethyl ether.

Attachment to Resin Bound Peptide—Route II:

The albumin binding moiety was dissolved in NMP/DCM (1:1, 10 ml). The activating reagent such as HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Attachment to peptide in solution—Route III:

Activated (active ester or symmetric anhydride) albumin binding moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After for 30 min the mixture was evaporated in vacuo and the crude peptide purified by preparative HPLC as described later.

SPPS Method E

SPPS method E refers to peptide synthesis by Fmoc chemistry on a Prelude Solid Phase Peptide Synthesiser from Protein Technologies (Tucson, Ariz. 85714 U.S.A.). A suitable resin is a pre-loaded, low-load Wang resin available from Novabiochem (e.g. low load fmoc-Lys(Mtt)-Wang resin, 0.35 mmol/g). Fmoc-deprotection was with 25% piperidine in NMP for 2×10 min. The coupling chemistry was DIC/HOAt/collidine in NMP. Amino acid/HOAt solutions (0.3 M in NMP at a molar excess of 3-10 fold) were added to the resin followed by the same molar equivalent of DIC (3 M in NMP) and collidine (3 M in NMP). For example, the following amounts of 0.3M amino acid/HOAt solution were used per coupling for the following scale reactions: Scale/ml, 0.10 mmol/2.5 ml, 0.25 mmol/5 ml. Coupling times were generally 60 minutes. Some amino acids including, but not limited to arginine and histidine were "double coupled", meaning that after the first coupling (e.g. 60 min), the resin is drained and more reagents are added (amino acid, HOAt, DIC, and collidine), and the mixture allowed to react gain (e.g. 60 min). When a chemical modification of a lysine side chain was desired, the lysine was incorporated as Lys(Mtt). The Mtt group was removed by washing the resin with DCM and suspending the resin in hexafluoroisopropanol/DCM (75:25) for 3×10 minutes followed by washings with DCM, 20% piperidine and NMP. The chemical modification of the lysine was performed either by manual synthesis (see SPPS method D) or by one or more automated steps on the Prelude peptide synthesiser as described above using suitably protected building blocks (see General methods).

2. Cleavage of Peptide from the Resin and Purification

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilised.

3. Methods for Detection and Characterisation

LCMS Methods

LCMS Method 1 (LCMS1)

An Agilent Technologies LC/MSD TOF (G1969A) mass spectrometer was used to identify the mass of the sample after elution from an Agilent 1200 series HPLC system. The deconvolution of the protein spectra was calculated with Agilent's protein confirmation software.

Eluents:
A: 0.1% Trifluoro acetic acid in water
B: 0.1% Trifluoro acetic acid in acetonitrile
Column: Zorbax 5 u, 300SB-C3, 4.8×50 mm
Gradient: 25%-95% acetonitrile over 15 min LCMS Method 2 (LCMS2)

A Perkin Elmer Sciex API 3000 mass spectrometer was used to identify the mass of the sample after elution from a Perkin Elmer Series 200HPLC system.

Eluents:
A: 0.05% Trifluoro acetic acid in water
B: 0.05% Trifluoro acetic acid in acetonitrile
Column: Waters Xterra MS C-18×3 mm id 5 µm
Gradient: 5%-90% acetonitrile over 7.5 min at 1.5 ml/min LCMS Method 3 (LCMS3)

A Waters Micromass ZQ mass spectrometer was used to identify the mass of the sample after elution from a Waters Alliance HT HPLC system.

Eluents:
A: 0.1% Trifluoro acetic acid in water
B: 0.1% Trifluoro acetic acid in acetonitrile
Column: Phenomenex, Jupiter C4 50×4.60 mm id 5 µm
Gradient: 10%-90% B over 7.5 min at 1.0 ml/min LCMS Method 4 (LCMS4)

LCMS4 was performed on a setup consisting of Waters Acquity UPLC system and LCT Premier XE mass spectrometer from Micromass. The UPLC pump was connected to two eluent reservoirs containing:
A: 0.1% Formic acid in water
B: 0.1% Formic acid in acetonitrile
The analysis was performed at RT by injecting an appropriate volume of the sample (preferably 2-10 µl) onto the column which was eluted with a gradient of A and B.

The UPLC conditions, detector settings and mass spectrometer settings were:
Column: Waters Acquity UPLC BEH, C-18, 1.7 µm, 2.1 mm×50 mm
Gradient: Linear 5%-95% acetonitrile during 4.0 min (alternatively 8.0 min) at 0.4 ml/min
Detection: 214 nm (analogue output from TUV (Tunable UV detector))
MS ionisation mode: API-ES
Scan: 100-2000 amu (alternatively 500-2000 amu), step 0.1 amu UPLC and HPLC Methods Method 05_B5_1

UPLC (method 05_B5_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 60% A, 40% B to 30% A, 70% B over 8 minutes at a flow-rate of 0.40 ml/min.

Method 05_B7_1

UPLC (method 05_B7_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 80% A, 20% B to 40% A, 60% B over 8 minutes at a flow-rate of 0.40 ml/min.

Method 04_A2_1

UPLC (method 04_A2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 90% A, 10% B to 60% A, 40% B over 16 minutes at a flow-rate of 0.40 ml/min.

Method 04_A3_1

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 75% A, 25% B to 45% A, 55% B over 16 minutes at a flow-rate of 0.40 ml/min.

Method 04_A4_1

UPLC (method 04_A4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 65% A, 35% B to 25% A, 65% B over 16 minutes at a flow-rate of 0.40 ml/min.

Method 08_B2_1

UPLC (method 08_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA
The following linear gradient was used: 95% A, 5% B to 40% A, 60% B over 16 minutes at a flow-rate of 0.40 ml/min.

Method 08_B4_1

UPLC (method 08_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA The following linear gradient was used: 95% A, 5% B to 95% A, 5% B over 16 minutes at a flow-rate of 0.40 ml/min.

Method 05_B10_1

UPLC (Method 05_B10_1): The RP-analyses was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$ The following linear gradient was used: 40% A, 60% B to 20% A, 80% B over 8 minutes at a flow-rate of 0.40 ml/min.

Method 09_B4_1

UPLC (Method 09_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95 $CH_3CN$, 0.05% TFA. The following linear gradient was used: 95% A, 5% B to 5 A, 95% B over 16 minutes at a flow-rate of 0.40 ml/min.

Method 09_B2_1

UPLC (Method 09_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95 $CH_3CN$, 0.05% TFA. The following linear gradient was used: 95% A, 5% B to 40% A, 60% B over 16 minutes at a flow-rate of 0.40 ml/min.

Method 10_B14_1

UPLC (Method 10_B14_1): The RP-analyses was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C.

The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.

Method 05_B8_1

UPLC (Method 05_B8_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 50% A, 50% B to 20% A, 80% B over 8 minutes at a flow-rate of 0.40 ml/min.

Method 07_B4_1

UPLC (Method 07_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.40 ml/min.

Method 04_A6_1

UPLC (Method 04_A6_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 10% A, 90% B over 16 minutes at a flow-rate of 0.35 ml/min.

Method 05_B2_1

UPLC (Method 05_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95 $CH_3CN$, 0.05% TFA. The following linear gradient was used: 95% A, 5% B to 40% A, 60% B over 16 minutes at a flow-rate of 0.40 ml/min.

Method 02_B4_4

HPLC (Method 02_B4_4): The RP-analysis was performed using a Alliance Waters 2695 system fitted with a Waters 2487 dualband detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 ml/min.

Method 02_B5_1

HPLC (Method 02_B5_1): The RP-analyses was performed using a Alliance Waters 2695 system fitted with a Waters 2487 dualband detector. UV detections were collected using a Symmetry C18, 3.5 um, 3.0 mm×100 mm column. Eluted with a linear gradient of 10-95% acetonitrile, 95-0% water, and 5% trifluoroacetic acid (1.0%) in water over 8 minutes at a flow-rate of 1.0 ml/min.

MALDI-MS Method

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

NMR Method

Proton NMR spectra were recorded using a Brucker Avance DPX 300 (300 MHz) with tetramethylsilane as an internal standard. Chemical shifts (δ) are given in ppm and splitting patterns are designated as follows: s, singlet; d, doublet; dd, double doublet; dt, double triplet t, triplet, tt, triplet of triplets; q, quartet; quint, quintet; sext, sextet; m, multiplet, and br=broad.

B. Synthesis of Intermediates

1. Synthesis of Mono Esters of Fatty Diacids

Overnight reflux of the C12, C14, C16 and C18 diacids with Boc-anhydride, DMAP, and t-butanol in toluene gives predominately the t-butyl mono ester. Obtained is after work-

2. Synthesis of 2-(1-Trityl-1H-imidazol-4-yl)-ethyl amine

Chem. 13

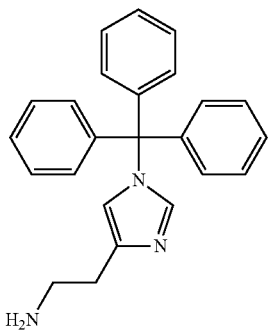

Histamine dihydrochloride (20.47 g; 0.111 mol) and triethylamine (48 mL; 0.345 mol) in absolute methanol (400 mL) were stirred at room temperature for 10 min. Trifluoroacetic acid ethyl ester (14.6 mL; 0.122 mol) in methanol (30 mL) was added dropwise over 30 min at 0° C. Reaction mixture was stirred for 3.5 hrs at room temperature and then it was evaporated to dryness in vacuo. The residue was dissolved in dichlormethane (450 mL) and triethylamine (31 mL; 0.222 mol) was added. Then trityl chloride (34.1 g; 0.122 mol) was added piecewise and mixture was stirred over night at room temperature. Chloroform (400 mL) and water (600 mL) were poured into reaction mixture. Aqueous layer was separated and extracted with chloroform (3×400 mL). The combined organic layers were dried over anhydrous magnesium sulfate. Solvent was removed and the beige solid was triturated with hexanes (1000 mL). Suspension was filtered to yield 2,2,2-trifluoro-N-[2-(1-trityl-1H-imidazol-4-yl)-ethyl]-acetamide as white solid.

Yield: 45.54 g (91%).

$^1$H NMR spectrum (300 MHz, CDCl$_3$, $\delta_H$): 8.44 (bs, 1H); 7.43 (s, 1H); 7.41-7.33 (m, 9H); 7.19-7.10 (m, 6H); 6.65 (s, 1H); 3.66 (q, J=5.9Hz, 2H); 2.79 (t, J=5.9Hz, 2H).

The above amide (45.54 g; 0.101 mmol) was dissolved in tetrahydrofuran (1000 mL) and methanol (1200 mL). A solution of sodium hydroxide (20.26 g; 0.507 mol) in water (500 mL) was added. Mixture was stirred for 2 hrs at room temperature and then it was concentrated in vacuo. The residue was separated between chloroform (1200 mL) and water (800 mL). Aqueous layer was extracted with chloroform (3×400 mL). Organic layers were combined and dried over anhydrous magnesium sulfate. Evaporation of the solvent yielded brown oil, which was dried for 3 days in vacuo to give the title product as beige solid.

Yield: 32.23 g (90%).

Overall yield: 82%.

M.p.: 111-113° C.

$^1$H NMR spectrum (300 MHz, CDCl$_3$, $\delta_H$): 7.39 (d, J=1.3, 1H); 7.38-7.32 (m, 9H); 7.20-7.12 (m, 6H); 6.61 (s, 1H); 3.00 (t, J=6.6Hz, 2H); 2.70 (t, J=6.5Hz, 2H); 1.93 (bs, 2H).

3. Synthesis of 2,2-Dimethyl-N-[2-(1-trityl-1H-imidazol-4-yl)-ethyl]-malonamic acid Chem. 14

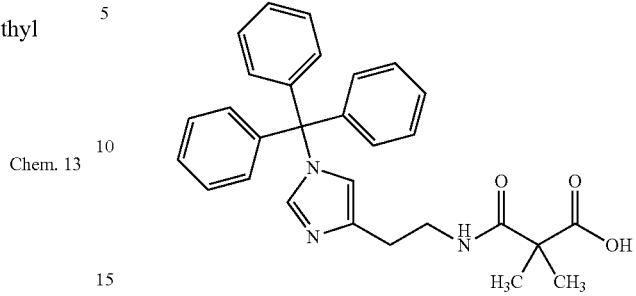

A mixture of Meldrum's acid (5.52 g, 38.3 mmol), potassium carbonate (26.5 g, 191 mmol) and methyl iodide (7.15 mL, 115 mmol) in acetonitrile (75 mL) was heated at 75° C. in a sealed tube for 7 hrs. The mixture was cooled to room temperature, diluted with dichloromethane (300 mL), filtered and the filtrate evaporated to dryness in vacuo. Ethyl acetate (75 mL), hexanes (75 mL) and water (50 mL) were added and phases were separated. The organic layer was washed with 10% aqueous solution of sodium thiosulfate (50 mL) and water (50 mL); dried over anhydrous magnesium sulfate and solvent removed in vacuo to give 2,2,5,5-tetramethyl-[1,3]dioxane-4,6-dione as white solid.

Yield: 6.59 g (79%).

R$_F$ (SiO$_2$, chloroform/ethyl acetate, 98:2): 0.60.

$^1$H NMR spectrum (300 MHz, CDCl$_3$, $\delta_H$): 1.76 (s, 6H); 1.65 (s, 6H).

A solution of 2-(1-Trityl-1H-imidazol-4-yl)-ethyl amine (5.00 g, 14.2 mmol) prepared as described above and triethylamine (9.86 mL, 70.7 mmol) in toluene (80 mL) was added dropwise over 50 min to a solution of the above dione compound (3.65 g, 21.2 mmol) in toluene (40 mL) at 75° C. The mixture was stirred at this temperature for additional 3 hrs (until the starting amine was detected on TLC), then it was evaporated to dryness. The residue was redissolved in chloroform (300 mL) and washed with 10% aqueous solution of citric acid (200 mL). The aqueous phase was extracted with chloroform (2×60 mL); the chloroform phases were combined, dried over anhydrous magnesium sulfate and solvent removed in vacuo. The residue was triturated with hot chloroform (140 mL); hexanes (70 mL) were added and the suspension was stirred at room temperature overnight. Solids were filtered off, washed with chloroform/hexanes mixture (1:1, 2×50 mL) and dried in vacuo to give the title product.

Yield: 6.73 g (88%).

M.p.: 161-162° C.

R$_F$ (SiO$_2$, chloroform/methanol, 85:15): 0.40.

$^1$H NMR spectrum (300 MHz, DMSO-d$_6$, $\delta_H$): 12.45 (bs, 1H); 7.66 (t, J=5.1Hz, 1H); 7.57-7.31 (m, 9H); 7.26 (s, 1H); 7.20-7.02 (m, 6H); 6.66 (s, 1H); 3.25 (m, 2H); 2.57 (t, J=7.3Hz, 2H); 1.21 (s, 6H).

4. Synthesis of 4-(4-tert-Butyl-phenyl)-butyric acid

Chem. 15

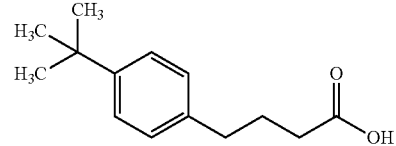

Aluminum chloride powder (80.0 g, 600 mmol) was added in portions to a stirred mixture of tert-butylbenzene (40.0 g, 300 mmol) and succinic anhydride (26.7 g, 267 mmol) and 1,1,2,2-tetrachloroethane (100 mL). After all the aluminum chloride had been added, the mixture was poured into a mixture of ice (500 mL) and concentrated hydrochloric acid (100 mL). The organic layer was separated, washed with water (500 mL) and the solvent distilled off. Solid residue was dissolved in hot 15% aqueous solution of sodium carbonate (1000 mL), filtered, cooled and the acid was precipitated with hydrochloric acid (acidified to pH=1). The crude acid was filtered, dried on air and recrystalised from benzene (500 mL) to give 4-(4-tert-butyl-phenyl)-4-oxo-butyric acid as colorless crystals.

Yield: 36.00 g (58%).

M.p.: 117-120° C.

$^1$H NMR spectrum (300 MHz, CDCl$_3$, δ$_H$): 7.93 (dm, J=8.3Hz, 2H); 7.48 (dm, J=8.3Hz, 2H); 3.30 (t, J=6.6Hz, 2H); 2.81 (t, J=6.6Hz, 2H); 1.34 (s, 9H).

A mixture of the above acid (36.0 g, 154 mmol), potassium hydroxide (25.8 g, 462 mmol), hydrazine hydrate (20 mL, 400 mmol) and ethylene glycol (135 mL) was refluxed for 3 hrs, and then distilled until the temperature of the vapor had risen to 196-198° C. After a further 14 hrs reflux, the mixture was allowed to cool slightly, and was then poured into cold water (200 mL). The mixture was acidified with concentrated hydrochloric acid (to pH=1) and extracted with dichloromethane (2×400 mL). The organic extracts were combined, dried over anhydrous magnesium sulfate, solvent removed in vacuo and the residue was purified by column chromatography (Silicagel 60A, 0.060-0.200 mm; eluent: hexanes/ethyl acetate 10:1-6:1) to give the title product as off white solid.

Yield: 16.25 g (48%).

M.p.: 59-60° C.

R$_F$ (SiO$_2$, ethyl acetate): 0.60.

$^1$H NMR spectrum (300 MHz, CDCl$_3$, δ$_H$): 7.31 (dm, J=8.1Hz, 2H); 7.12 (dm, J=8.1Hz, 2H); 2.64 (t, J=7.6Hz, 2H); 2.38 (t, J=7.4Hz, 2H); 1.96 (m, 2H); 1.31 (s, 9H).

5. Synthesis of 2,2-Dimethyl-N-(1-trityl-1H-imidazol-4-ylmethyl)-malonamic acid

Chem. 16

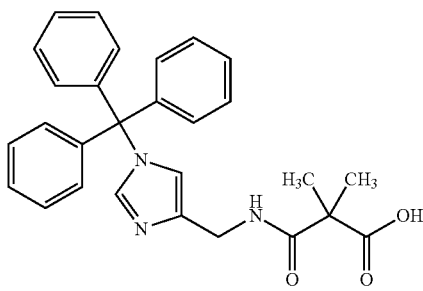

Hydroxylamine hydrochloride (15.9 g, 229 mmol) was added to a solution of 4(5)-imidazolecarboxaldehyde (20.0 g, 209 mmol) and sodium carbonate (12.1 g, 114 mmol) in water (400 mL) and the resulting solution was stirred at room temperature overnight. The mixture was evaporated to 100 mL and cooled in an ice bath. The solids were separated by filtration and the filtrate was concentrated to 40 mL. After cooling to 0° C., another portion of crystals was obtained. The solids (23 g) were combined and recrystallised from ethanol (approx. 160 mL) to afford imidazole-4(5)-carbaldehyde oxime as colorless crystals.

Yield: 15.98 g (69%).

$^1$H NMR spectrum (300 MHz, acetone-d$_3$+D$_2$O, δ$_H$): 7.78 (bs, 1H); 7.74 (d, J=0.9Hz, 1H); 7.43 (s, 1H).

Acetyl chloride (51.0 mL, 718 mmol) was added dropwise to methanol (670 mL) at 0° C. under argon. After 30 min, the cooling bath was removed and the above oxime (16.0 g, 144 mmol) was added, followed by palladium on carbon (5 wt %, 6.1 g). The mixture was hydrogenated at atmospheric pressure for 17 hrs, then it was filtered through Celite and the solvent evaporated to give pure 4-(aminomethyl)-imidazole dihydrochloride as colorless crystals.

Yield: 23.92 g (98%).

$^1$H NMR spectrum (300 MHz, D$_2$O, δ$_H$): 8.72 (s, 1H); 7.60 (s, 1H); 4.33 (s, 2H).

The above amine dihydrochloride (18.9 g; 111 mmol) and triethylamine (93 mL; 667 mmol) in methanol (1000 mL) were stirred at room temperature for 10 min. Trifluoroacetic acid ethyl ester (13.3 mL; 111 mmol) in methanol (30 mL) was added dropwise over 40 min at 0° C. Reaction mixture was stirred for 18 hrs at room temperature and then it was evaporated to dryness in vacuo. The residue was dissolved in dry dichlormethane (2000 mL) and triethylamine (31 mL; 222 mmol) was added. Then trityl chloride (31.6 g; 113 mmol) was added and the mixture was stirred overnight at room temperature. Chloroform (1000 mL) and water (1000 mL) were poured into the reaction mixture. Aqueous layer was separated and extracted with chloroform (2×300 mL). The combined organic layers were dried over anhydrous magnesium sulfate. Solvent was removed and the beige solid was triturated with hexanes (1000 mL). Suspension was filtered to yield 2,2,2-trifluoro-N-(1-trityl-1H-imidazol-4-ylm-ethyl)-acetamide as white solid.

Yield: 46.59 g (96%).

R$_F$ (SiO$_2$, dichloromethane/methanol 95:5): 0.35.

$^1$H NMR spectrum (300 MHz, DMSO-d$_6$, δ$_H$): 9.77 (t, J=5.7Hz, 1H); 7.47-7.34 (m, 9H); 7.33 (d, J=1.5Hz, 1H); 7.13-7.03 (m, 6H); 6.80 (d, J=0.8Hz, 1H); 4.25 (d, J=5.7Hz, 2H).

The above amide (46.6 g; 107 mmol) was dissolved in tetrahydrofuran (600 mL) and ethanol (310 mL). A solution of sodium hydroxide (21.4 g; 535 mmol) in water (85 mL) was added. Mixture was stirred for 5 hrs at room temperature and then it was concentrated in vacuo. The residue was separated between chloroform (1600 mL) and water (800 mL). Aqueous layer was extracted with chloroform (4×200 mL). Organic layers were combined and dried over anhydrous magnesium sulfate. Evaporation of the solvent yielded (1-trityl-1H-imidazol-4-yl)-methylamine as off white solid.

Yield: 36.30 g (100%).

$^1$H NMR spectrum (300 MHz, CDCl$_3$, δ$_H$): 7.38 (d, J=1.3, 1H); 7.36-7.30 (m, 9H); 7.18-7.10 (m, 6H); 6.69 (m, 1H); 3.77 (s, 2H); 1.80 (bs, 2H).

A solution of the above amine (10.0 g, 29.5 mmol) and triethylamine (20.5 mL, 147 mmol) in toluene (220 mL) was added dropwise over 45 min to a solution of 2,2,5,5-tetramethyl-[1,3]dioxane-4,6-dione (3.65 g, 21.2 mmol) in toluene (80 mL) at 75° C. The mixture was stirred at this temperature for additional 3 hrs (until the starting amine was detected on TLC), then it was evaporated to dryness. The residue was redissolved in chloroform (500 mL) and washed with 10% aqueous solution of citric acid (300 mL). The aqueous phase was extracted with chloroform (100 mL); the chloroform phases were combined, washed with water (150 mL) dried over anhydrous magnesium sulfate and solvent removed in vacuo. The residue was purified by flash column chromatography (silica gel Fluka 60, dichloromethane/methanol 98:2 to 9:1) and crystallised from chloroform/hexanes mixture to give the title product as beige crystals.

Yield: 9.80 g (73%).
M.p.: 174-175° C.
$R_F$ (SiO$_2$, chloroform/methanol, 85:15): 0.35.
$^1$H NMR spectrum (300 MHz, CDCl$_3$, $\delta_H$): 8.45 (t, J=5.8Hz, 1H); 7.53 (s, 1H); 7.40-7.28 (m, 9H); 7.14-7.01 (m, 6H); 6.84 (s, 1H); 4.39 (d, J=5.8Hz, 2H); 1.44 (s, 6H).

6. Synthesis of 3-(1-Trityl-1H-imidazol-4-yl)-propyl amine

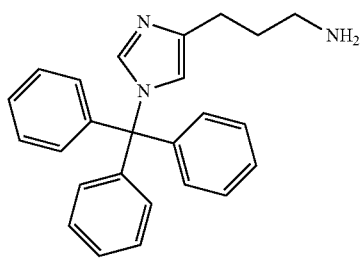

Chem. 17

Ethyl 3-(1-trityl-4-imidazolyl)propionate (93.0 g, 223 mmol) in tetrahydrofuran/diethyl ether (1:1, 100 mL) was added dropwise to a suspension of lithium aluminium hydride (17.0 g, 446 mmol) during 1 hr. The mixture was refluxed for 3 hrs, then treated with water (100 mL), 20% sodium hydroxide (100 mL) and water (100 mL) under cooling with ice/water, filtered and the solid washed with tetrahydrofuran. The organic phase was dried over anhydrous potassium carbonate, filtered and evaporated to give 3-(1-trityl-4-imidazolyl)propanol as white solid.

Yield: 68.0 g (82%).
M.p.: 127-129° C.
$^1$H NMR spectrum (300 MHz, CDCl$_3$, $\delta_H$): 7.40-7.24 (m, 10H); 7.17-7.06 (m, 6H); 6.55 (s, 1H); 3.72 (t, J=5.3Hz, 2H); 2.68 (t, J=6.6Hz, 2H); 1.86 (m, 2H).

Methanesulfonyl chloride (8 mL, 104 mmol) was added dropwise to a solution of the above alcohol (32.0 g, 86.8 mmol) in dichloromethane (400 mL) and triethyl amine (15.5 mL) at 0° C. during 1 hr. The mixture was stirred without cooling for an additional 1 hr; then it was washed with 5% sodium bicarbonate and dried over anhydrous magnesium sulfate. Dichloromethane was evaporated at 30° C. in vacuo and the residual oily mesylate was used directly in the next step.

Yield: 31.2 g (80%).
$^1$H NMR spectrum (300 MHz, CDCl$_3$, $\delta_H$): 7.37-7.30 (m, 10H); 7.16-7.09 (m, 6H); 6.58 (s, 1H); 4.24 (t, J=6.3Hz, 2H); 2.96 (s, 3H); 2.67 (m, 2H); 2.10 (m, 2H).

A mixture of the above mesylate (30.0 g, 67 mmol), potassium phtalimide (18.0 g, 100 mmol), sodium iodide (4.0 g, 26.7 mmol) and dimethylformamide (200 mL) was stirred overnight at ambient temperature and then treated with water (2 L) and benzene (2 L). The organic phase was dried over anhydrous magnesium sulfate, filtered and solvent evaporated giving a residue, which was recrystallised from benzene yielding 1-trityl-4-(3-phtalimidopropyl)imidazole as white solid.

Yield: 17.2 g (52%).
M.p.: 211-214° C.

$^1$H NMR spectrum (300 MHz, CDCl$_3$, $\delta_H$): 7.83 (m, 2H); 7.72 (m, 2H); 7.39-7.27 (m, 10H); 7.18-7.07 (m, 6H); 6.60 (d, J=0.9Hz, 1H); 3.72 (t, J=7.4Hz, 2H); 2.60 (t, J=7.5Hz, 2H); 1.99 (m, 2H).

The above imidazole derivative (26.6 g, 53.5 mmol) was dissolved in ethanol (300 mL) and tetrahydrofuran (150 mL) at 60° C., hydrazine hydrate (50 g, 1 mol) was added and the solution was refluxed for 6 hrs and then heated at 70° C. overnight. The solid was removed by filtration and the filtrate was treated with 25% aqueous solution of ammonia (2.5 l) and dichloromethane (2.5 L). The organic layer was dried over anhydrous potassium carbonate and evaporated to give a residue, which was purified by column chromatography on silica gel (Fluke 60, chloroform saturated with ammonia/methanol) giving the title compound as white solid.

Yield: 14.2 g (72%).
M.p.: 112-113° C.
$R_F$ (SiO$_2$, chloroform saturated with ammonia/methanol 9:1): 0.30.
$^1$H NMR spectrum (300 MHz, CDCl$_3$, $\delta_H$): 7.37-7.28 (m, 10H); 7.18-7.09 (m, 6H); 6.53 (d, J=1.3Hz, 1H); 2.74 (t, J=6.9Hz, 2H); 2.59 (t, J=7.4Hz, 2H); 1.95 (bs, 2H); 1.78 (m, 2H).

7. Synthesis of 2,2-Dimethyl-N-[3-(1-trityl-1H-imidazol-4-yl)-propyl]-malonamic acid

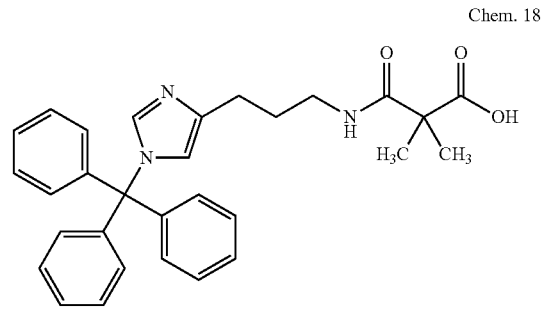 [SMILES: CC(C)(C(=O)O)C(=O)NCCCc1cn(C(c2ccccc2)(c2ccccc2)c2ccccc2)cn1]

Chem. 18

2-Chlorotrityl chloride resin (2.3 g, 3.0 mmol) was swelled in DCM for 20 mins and filtered. Dimethylmalonic acid (2 eq; 6.0 mmol; 793 mg) was dissolved i DCM:DMF 1:1 (10 mL) and added to the resin followed by DIPEA (6 eq; 18.0 mmol; 3.14 mL) and DCM (10 mL). The resin was shaken overnight at RT. The resin was filtered and washed with DCM:MeOH:DIPEA (17:2:1), DCM, NMP og DCM (2×25 mL of each). The resin was swelled in DMF for 20 mins and filtered. HOAt (3 eq; 9.0 mmol; 1.23 g), DIC (3 eq; 9.0 mmol; 1.40 mL) and DMF (25 mL) was added and the resin was shaken for 90 min at RT. The resin was filtered and 3-(1-Trityl-1H-imidazol-4-yl)-propyl amine (1.8 eq; 5.40 mmol; 1.84 g), DIPEA (4 eq; 6.0 mmol; 2.09 mL), and DMF (10 mL) was added. The resin was shaken for 2 days. The resin was filtered and washed with NMP (5×20 mL) and DCM (10×20 mL). 2,2,2-Trifluoroethanol/dichlormethan 1:1 (20 mL) was added to the resin and it was shaken for 2 hrs. The resin was washed with 2,2,2-Trifluoroethanol/dichlormethan 1:1 (10 mL) and the combined filtrates were collected and concentrated in vacuo to yield the title compound.

Yield: 600 mg (41%).
LCMS4: m/z=482 (M+1)
UPLC (method 02_B4_4): Rt=8.07 min
1H NMR spectrum (300 MHz, DMSO-d$_6$, $\delta_H$): 7.36-7.44 (9H, m), 7.07-7.12 (6H, m), 6.62 (1H, s), 3.02-3.09 (2H, q), 2.38-2.43 (2H, t), 1.61-1.69 (2H, m), 1.26 (6H, s).

8. Synthesis of 2,2-Dimethyl-N-[3-(1-trityl-1H-imidazol-4-yl)-propyl]-malonamic acid Synthesis of 2,2-Dimethyl-N-pyridin-2-ylmethylmalonamic acid

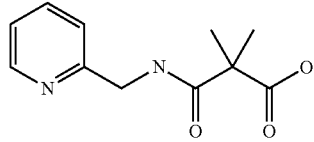

Chem. 19

Chlorotrityl chloride resin (2.3 g, 3.0 mmol) was swelled in DCM for 20 mins and filtered. Dimethylmalonic acid (2 eq; 6.0 mmol; 793 mg) was dissolved i DCM:NMP 1:1 (10 mL) and added to the resin followed by DIPEA (6 eq; 18.0 mmol; 3.14 mL) and DCM (10 mL). The resin was shaken overnight at RT. The resin was filtered and washed with DCM:MeOH: DIPEA (17:2:1), DCM, NMP og DCM (2×25 mL of each). The resin was swelled in NMP for 20 mins and filtered. HOAt (3 eq; 9.0 mmol; 1.23 g), DIC (3 eq; 9.0 mmol; 1.40 mL) and NMP (25 mL) was added and the resin was shaken for 90 min at RT. The resin was filtered and 2-(Aminomethyl)pyridine (2 eq; 6 mmol; 659 mg), DIPEA (4 eq; 6.0 mmol; 2.09 mL), and NMP (10 mL) was added. The resin was shaken for overnigth. The resin was filtered and washed with NMP (5×20 mL) and DCM (10×20 mL). TFA/TIS/water (95:2.5:2.5; 30 mL) was added to the resin and it was shaked for 1 hr, filtered and concentrated in vacuo to yield the title compound.

Yield: 600 mg (41%).
LCMS4: m/z=223 (M+1)
UPLC (method 08_B4__1): Rt=1.79 min

C. Synthesis of Compounds of the Invention

Example 1

[Aib$^8$,His$^{31}$,Gln$^{34}$]GLP-1(7-37)-peptide (SEQ ID NO: 4)

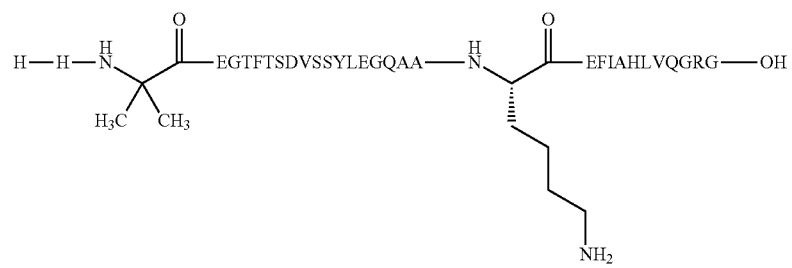

Chem. 20

Preparation method: SPPS method A
UPLC (method 05_B2__1): Rt=9.78 min (97%)
UPLC (method 04_A2__1): Rt=13.48 min (93%)
LCMS4: (M/4)+1=830; (M/3)+1=1106; Exact mass=3320; Calculated=3320

Example 2

N$^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib$^8$,His$^{31}$,Gln$^{34}$]GLP-1(7-37)-peptide (SEQ ID NO: 4)

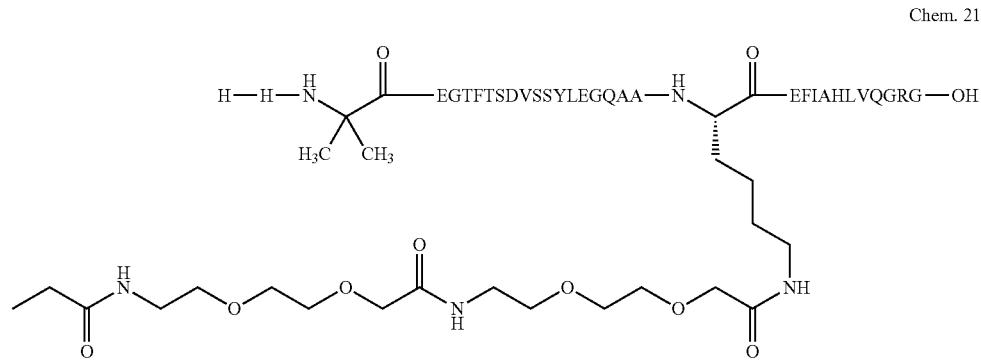

Chem. 21

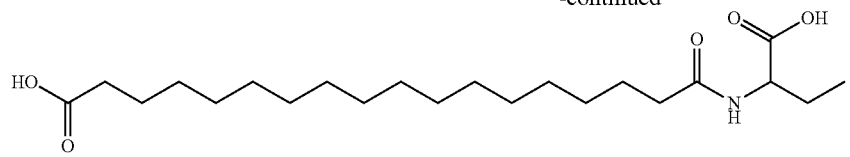

Preparation method: SPPS method A followed by manual Mtt group removal and manual coupling of Fmoc-OEG-OH, Fmoc-Glu-OtBu, and octadecanedioic acid mono-tert-butyl ester
HPLC (method 02_B4__4): Rt=9.02 min (99%)
HPLC (method 02_B5__1): Rt=13.15 min (98%)
LCMS4: (M/4)+1=1010; (M/3)+1=1346; Exact mass=4036; Calculated=4036

Example 3

[Aib$^8$,Glu$^{30}$,His$^{31}$,Gln$^{34}$,Lys$^{36}$] GLP-1(7-37)yl-Glu$^{38}$-peptide amide(SEQ ID NO: 2)

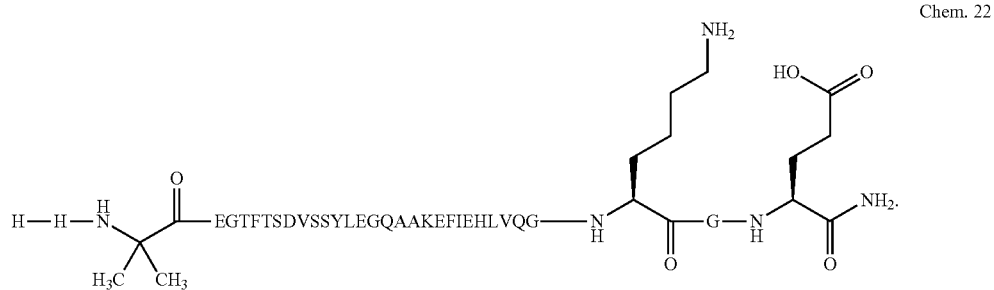

Chem. 22

Preparation method: SPPS method A
UPLC (method 05_B2__1): Rt=9.46 min (100%)
UPLC (method 04_A3__1): Rt=5.12 min (93%)
LCMS4: (M/4)+1=870; (M/3)+1=1160; Exact mass=3479; Calculated=3479

Example 4

N$^{\epsilon 12}$(2-{2-[2-(2-{2-[2-(17-Carboxy-heptadecanoylamino)ethoxy]ethoxy}acetylamino)ethoxy]ethoxy}acetyl) [Aib$^8$,Lys$^{12}$, Glu$^{22}$,Arg$^{26}$,His$^{31}$,Gln$^{34}$]GLP-1(7-37)-peptide (SEQ ID NO: 5)

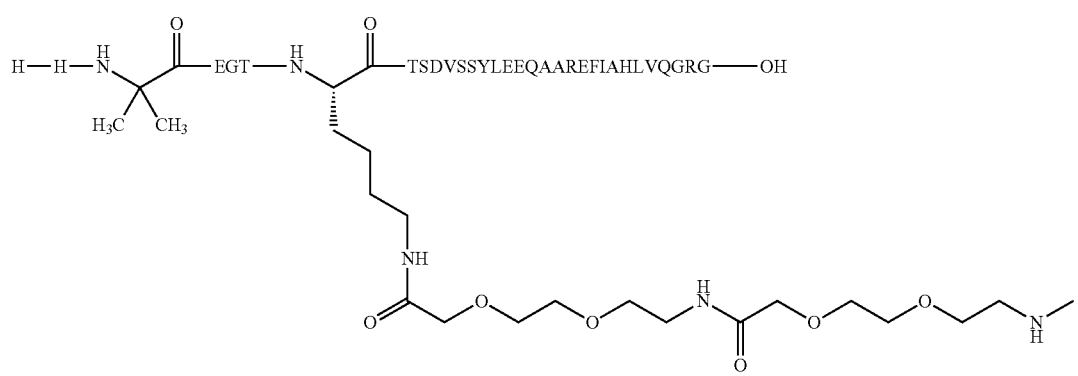

Chem. 23

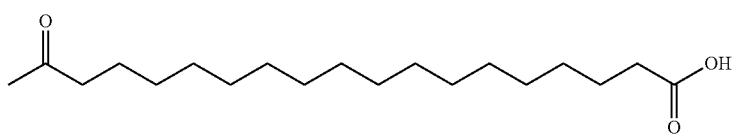

Preparation method: The peptide was prepared by SPPS method B using a Wang-resin (LL). Fmoc-Lys(Mtt)-OH was used in position 12, and Boc-His(trt)-OH was used in position 7. The Mtt was removed with HFIP manually. The final product was characterised by UPLC and MALDI-MS.
UPLC (method 08_B4_1): Rt=8.2 min
UPLC (method 04_A3_1): Rt=9.85 min
MALDI-MS: 3986

Example 5

$N^{\epsilon 12}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib$^8$,Lys$^{12}$, His$^{31}$,Gln$^{34}$]GLP-1(7-37)-peptide (SEQ ID NO: 7)

Chem. 24

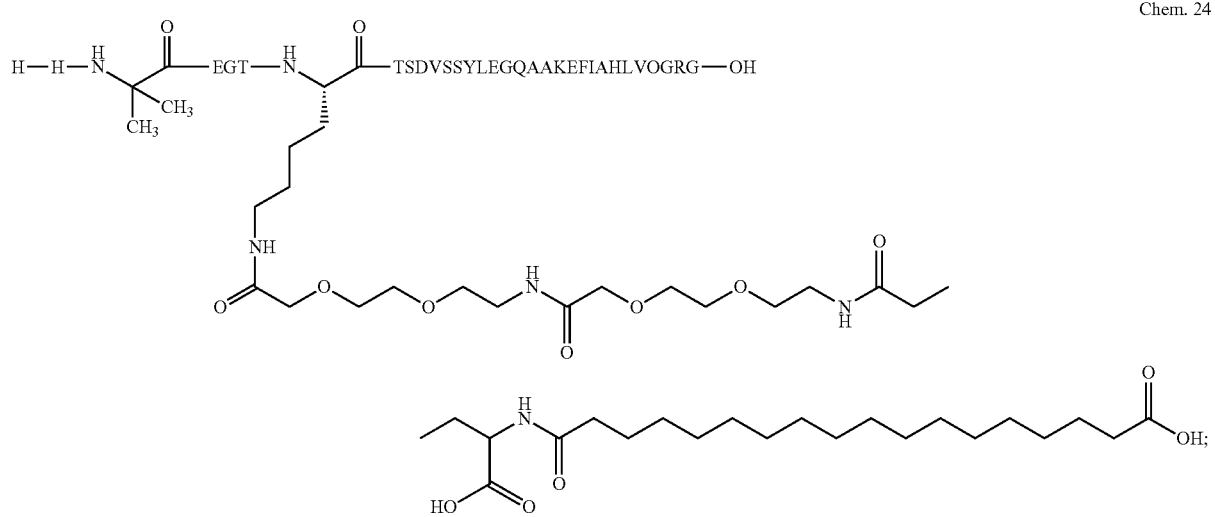

Preparation method: The peptide was prepared by SPPS method B using a Wang-resin (LL). Fmoc-Lys(Mtt)-OH was used in position 12, and Boc-His(trt)-OH was used in position 7. The Mtt was removed with HFIP manually. The final product was characterised by UPLC and MALDI-MS.
UPLC (method 08_B4_1): Rt=7.9 min
UPLC (method 04_A4_1): Rt=3.9 min
MALDI-MS: 4016.8

Example 6

$N^{\epsilon 12}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib$^8$,Lys$^{12}$, Glu$^{22}$,Arg$^{26}$,His$^{31}$,Gln$^{34}$]GLP-1(7-37)-peptide (SEQ ID NO: 5)

Chem. 25

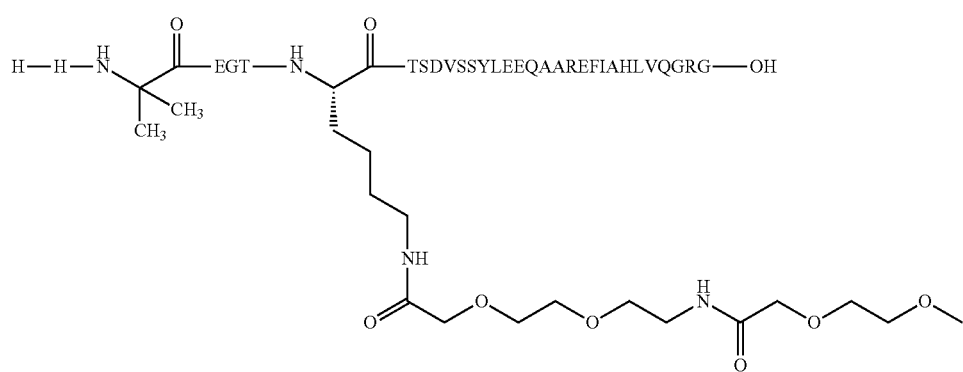

-continued

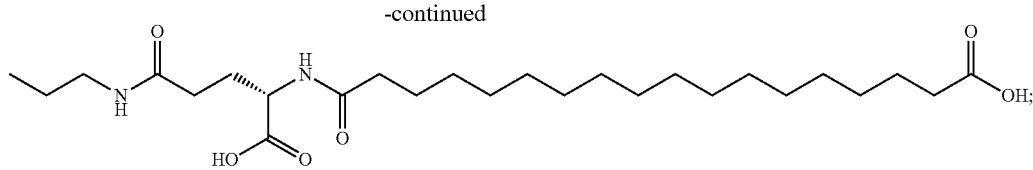

Preparation method: The peptide was prepared by SPPS method B using a Wang-resin (LL). Fmoc-Lys(Mtt)-OH was used in position 12, and Boc-His(trt)-OH was used in position 7. The Mtt was removed with HFIP manually. The final product was characterised by UPLC and MALDI-MS.
UPLC (method 08_B4_1): Rt=7.9 min
UPLC (method 04_A3_1): Rt=7.1 min
MALDI-MS: 4114

Example 7

$N^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His$^{31}$,Gln$^{34}$]GLP-1-(7-37)-peptide (SEQ ID NO: 9)

Chem. 26

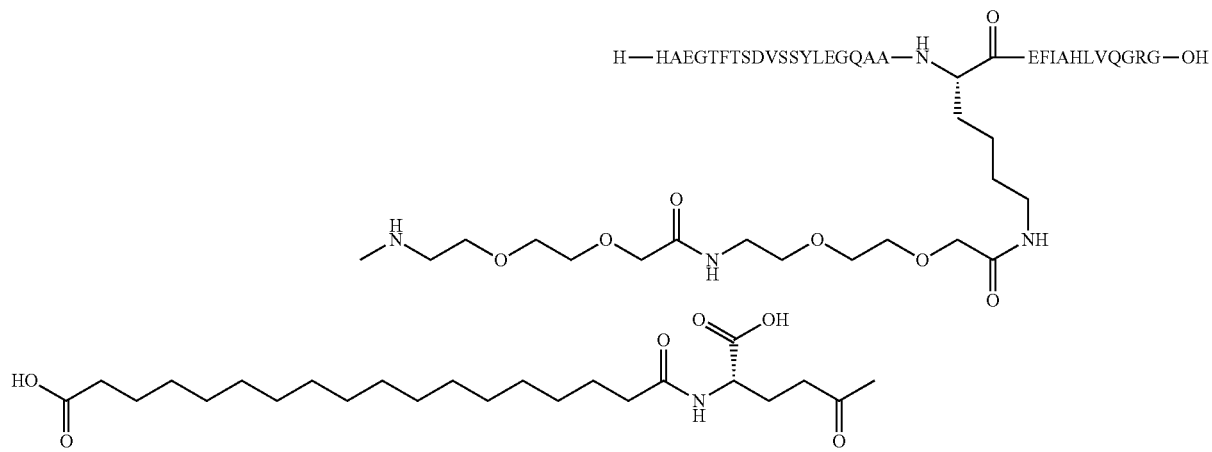

Preparation method: SPPS method A
UPLC (method 08_B2_1): Rt=12.90 min (96%)
UPLC (method 05_B5_1): Rt=6.34 min (91%)
LCMS4: (M/4)+1=1006; (M/3)+1=1341; Exact mass=4022; Calculated=4023

Example 8

$N^{\epsilon 18}$[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib$^8$,Lys$^{18}$,Glu$^{22}$,Arg$^{26}$,His$^{31}$,Gln$^{34}$] GLP-1(7-37)-peptide (SEQ ID NO: 10)

Chem. 27

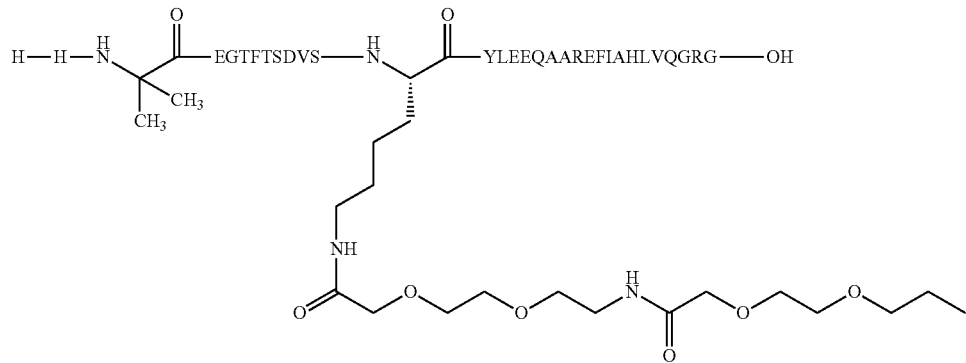

-continued

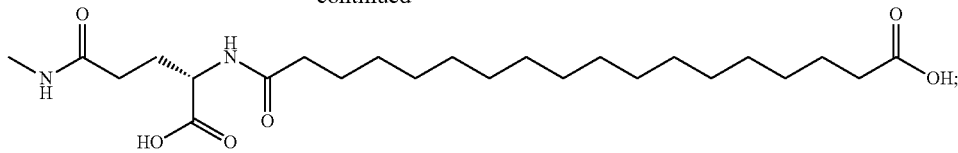

Preparation method: The peptide was prepared by SPPS Method B and the final product was characterised by analytical UPLC and LC-MS with the exception that the Mtt removal and coupling of the linker was done by method D.
UPLC (method 08_B2_1): Rt=12.4 min
UPLC (method 04_A3_1): Rt=8.5 min
LCMS4: 4178.0
Calculated MW=4177.7

Example 9

$N^{\epsilon 26}$[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Gly$^8$,His$^{31}$,Gln$^{34}$] GLP-1(7-37)-peptide (SEQ ID NO: 12)

Chem. 28

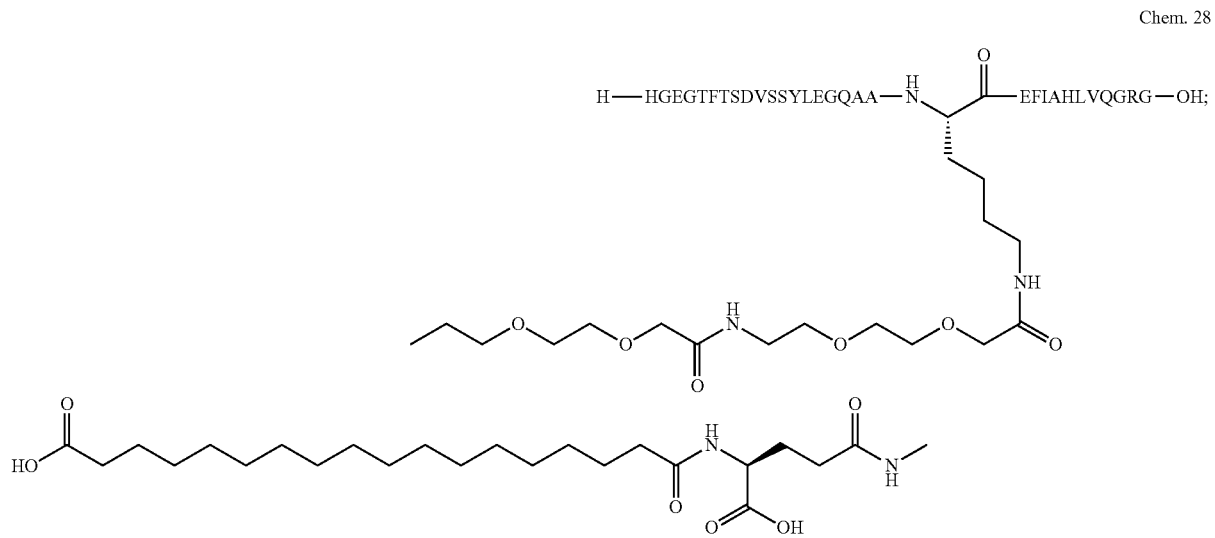

Preparation method: The peptide was prepared by SPPS Method B and the final product was characterised by analytical UPLC and LC-MS with the exception that the Mtt removal and coupling of the linker was done by method D.
UPLC (method 08_B2_1): Rt=13.0 min
UPLC (method 04_A3_1): Rt=10.0 min
LCMS4: 4008.0
Calculated MW=4008.49

Example 10

$N^{\epsilon 26}$ [(S)-4-Carboxy-4-(2-{2-[2-(2-{2-[2-(17-carboxy-heptadecanoylamino)ethoxy]ethoxy}acetylamino)ethoxy]-ethoxy}acetylamino)butyryl] [Aib$^8$,His$^{31}$,Gln$^{34}$]GLP-1(7-37)-peptide (SEQ ID NO: 4)

Chem. 29

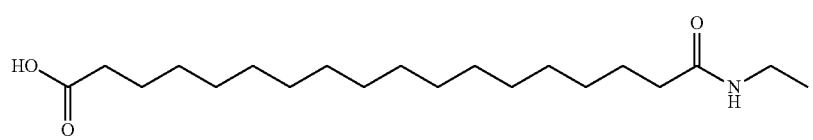

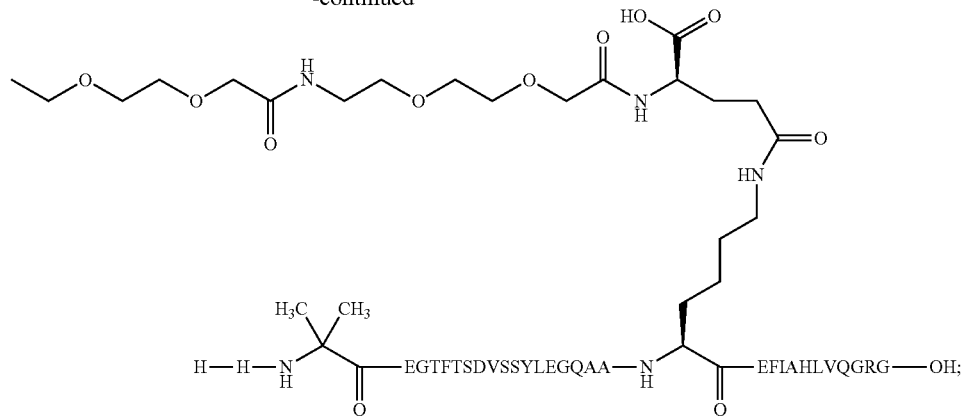

The SPPS method B was used, and the final product was characterised by UPLC and LC-MS.
UPLC (method 04_A4_1): Rt=6.08 min
UPLC (method 08_B4_1): Rt=8.61 min
LCMS4: (1010×4)−4=4036
Calculated MW=4036.5

Example 11

N$^{\epsilon 28}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][D-Ala$^8$,His$^{31}$,Gln$^{34}$]GLP-1(7-37)-peptide (SEQ ID NO: 15)

Chem. 30

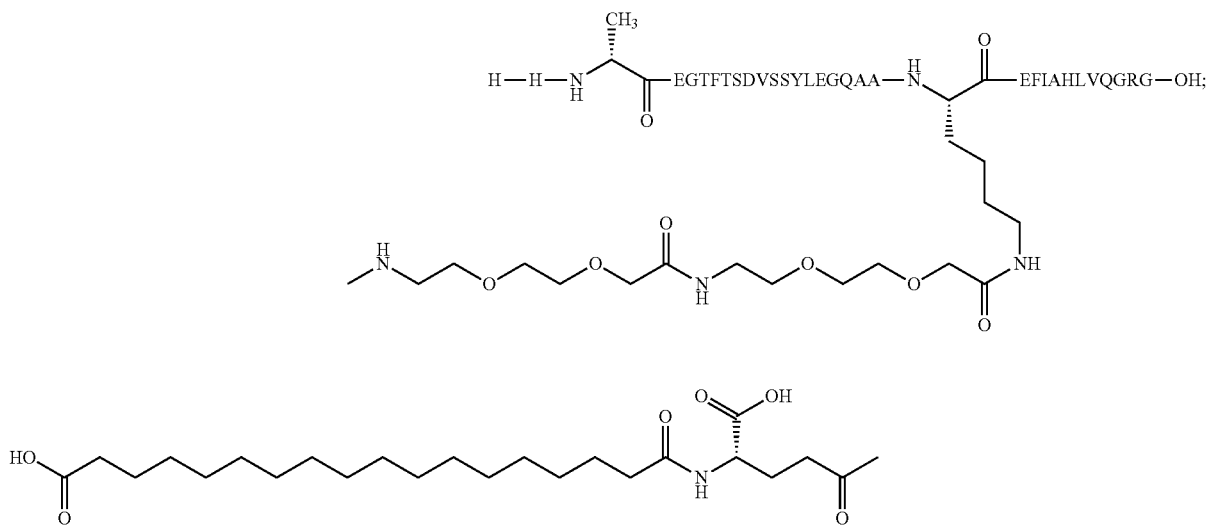

Preparation method: The SPPS method B was used, and the final product was characterised by UPLC and LCMS
UPLC (method 04_A3_1): Rt=10.33 min
UPLC (method 08_B4_1): Rt=8.80 min
LCMS4: (1005.97×4)−4=4019.9
Calculated MW=4022.5

Example 12

N$^8$ 3H-Imidazol-4-yl-acetyl, N$^{\epsilon 28}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His$^{31}$,Gln$^{34}$]GLP-1(8-37)-peptide (SEQ ID NO: 9)

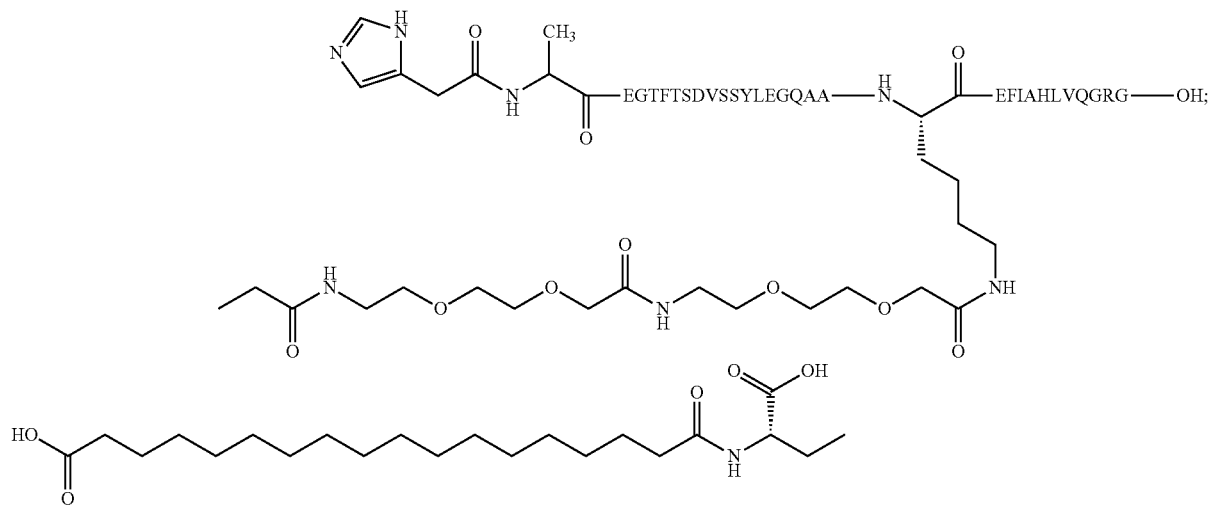

Chem. 31

Preparation method: The peptide was prepared by SPPS Method B and the final product was characterised by analytical UPLC and LC-MS with the exception that the 2 equivalents DIEA was added to the solution of Imidazole-4-acetic acid hydrochloride and HOAt, and the solution was filtered before use.

UPLC (method 04_A3__1): Rt=9.82 min
UPLC (method 08_B4__1): Rt=8.95 min

LCMS1: (999.26×4)−4=3393.0
Calculated MW=3393.5

Example 13

N$^{\epsilon 26}$[2-(2-{2-[2-(2-{2-[(S) 4-Carboxy-4-(17-carboxyheptadecanoylamino)butyrylamino]ethoxy}ethoxy)acetylamino]ethoxy}ethoxy)acetyl][Ser$^8$,His$^{31}$,Gln$^{34}$] GLP-1(7-37)-peptide (SEQ ID NO: 16)

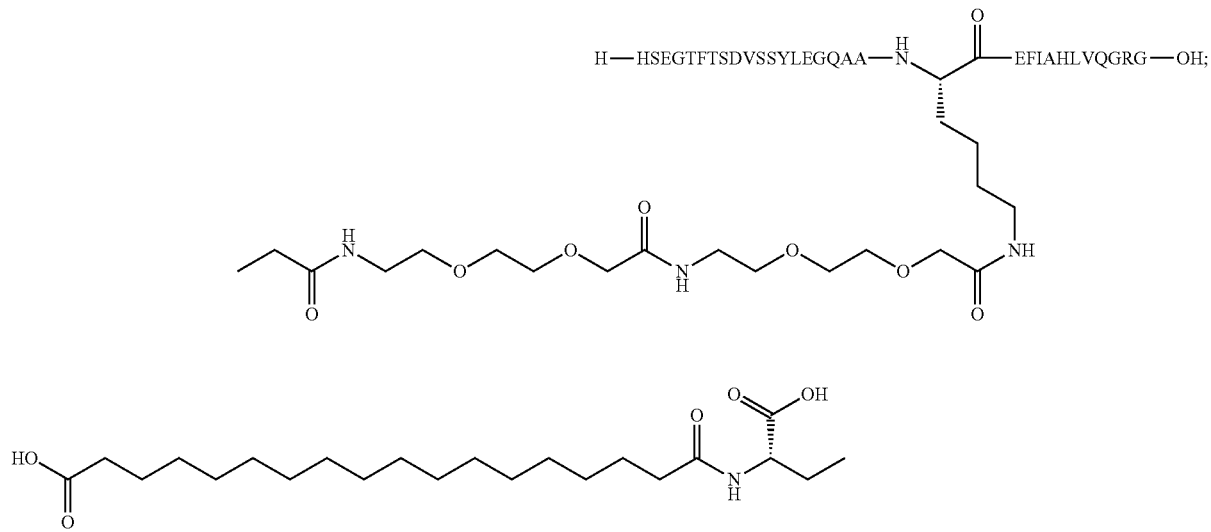

Chem. 32

Preparation method: The peptide was prepared by SPPS Method B and the final product was characterised by analytical UPLC and LC-MS with the exception that the Mtt removal and coupling of the linker was done by method D.
UPLC (method 08_B2_1): Rt=12.8 min
UPLC (method 04_A4_1): Rt=4.5 min
LCMS4: 4038.0
Calculated MW=4008.51

Example 14

$N^{\epsilon 26}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl][Aib$^8$,His$^{31}$,Gln$^{34}$]GLP-1(7-37)-peptide (SEQ ID NO: 4)

Chem. 33

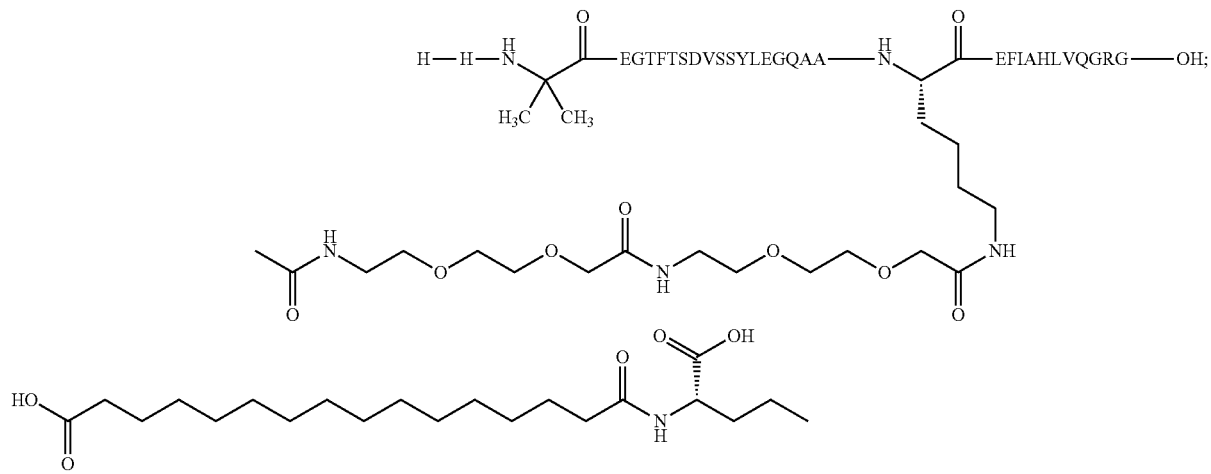

Preparation method: SPPS method A
UPLC (method 09_B2_1): Rt=12.48 min (91%)
UPLC (method 05_B5_1): Rt=5.67 min (91%)
LCMS4: (M/4)+1=1002; (M/3)+1=1337; Exact mass=4008; Calculated=4008

Example 15

$N^{\epsilon 27}$-{2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl}-(Aib$^8$,Arg$^{26}$,Lys$^{27}$,His$^{31}$,Gln$^{34}$) GLP-1(7-37)-peptide (SEQ ID NO: 17)

Chem. 34

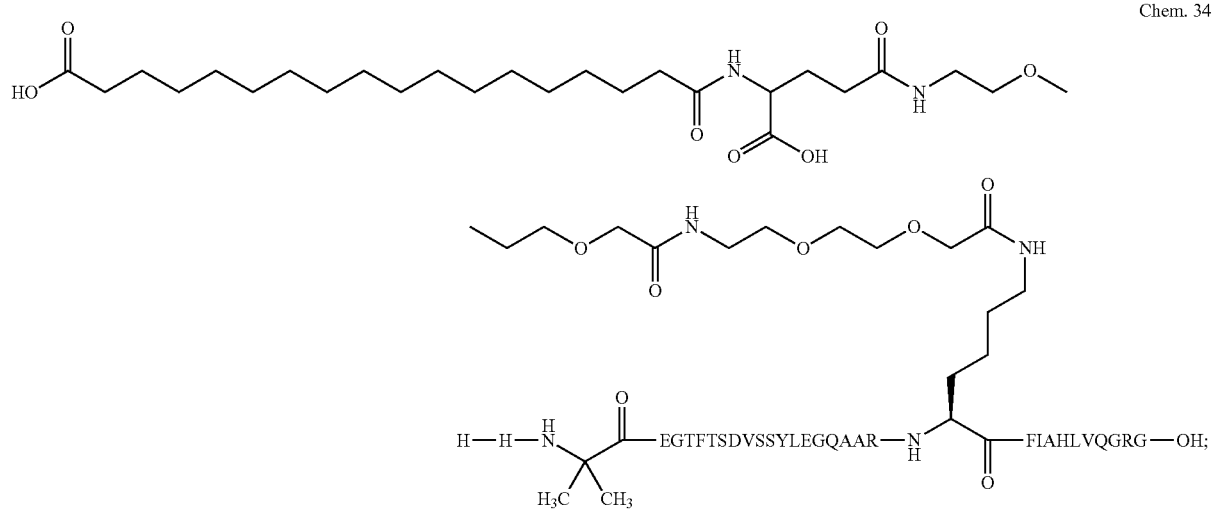

Preparation method: The peptide was prepared by SPPS Method E and the final product was characterised by analytical UPLC and MALDI TOF-MS:
UPLC (method 07_B4__1): Rt=8.3 min
UPLC (method 04_A3__1): Rt=11.2 min
MALDI-MS: 4062
Calculated MW=4064

Example 16

$N^{\epsilon 26}$ [2-(2-(2-{2-[(S)-4-Carboxy-4-(15-carboxypentadecanoylamino)butyrylamino]ethoxy}ethoxy)acetyl][Aib$^8$,His$^{31}$,Gln$^{34}$]GLP-1(7-37)-peptide (SEQ ID NO: 4)

HPLC on a 20 mm×250 mm column packed with either 5 u or 7 u C18 silica. The peptide was dissolved in 5 ml 50% acetic acid and diluted to 20 ml with H$_2$O and injected on the column which then was eluted with a gradient of 40-60% CH$_3$CN in 0.1% TFA 10 ml/min during 50 min at 40° C. The peptide containing fractions were collected and purity assessed by MALDI and UPLC. The purified peptide was lyophilised after dilution of the eluate with water.

The theoretical molecular mass of 3863.3 was confirmed by MALDI.

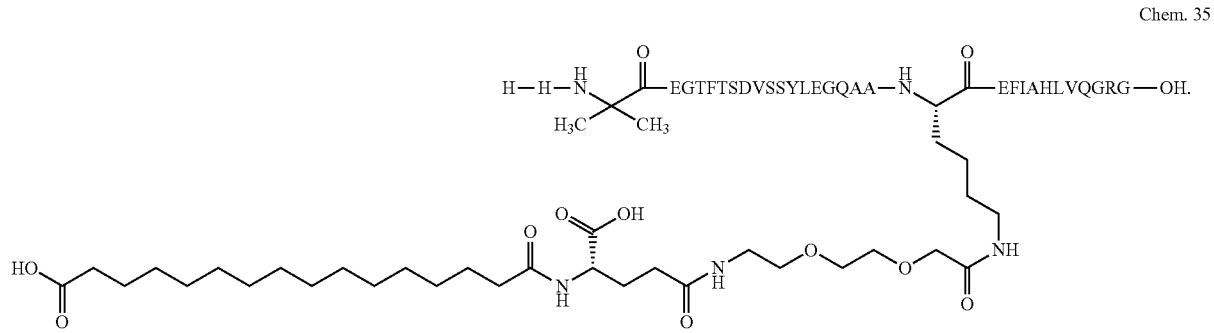

Chem. 35

The peptide was synthesised on Gly-PHB Tentagel resin with a loading of 0.22 mmol/g. The synthesis was performed on a Liberty synthesiser under microwave conditions using 5 minute single couplings with DIC/HOAt at up to 70° C. except for histidine which was coupled for 20 minutes at up to 50° C. All amino acids were protected with standard protecting groups except for lysines to be acylated (in this case Lys26) which were protected with Mtt. Deprotection was with 5% piperidine in NMP at 50° C. for 3 minutes. After the synthesis was completed, the N-terminus was blocked with 10 equivalents of Boc-carbonate and 10 equivalents of DIPEA for 30 minutes. The Mtt groups were removed by treatment with neat hexafluoroisopropanol for 20 minutes and the side chains were built stepwise on the Liberty using the same protocol as above using Fmoc-8-amino-3,6-dioxaoctanoic acid, Fmoc-Glu-OBut, and hexadecanedioic acid mono-t-butyl ester. The peptide was cleaved with TFA/water/TIS (95:2.5:2.5) for 2 hours and isolated by precipitation with diethylether. The crude peptide was purified by preparative Retention time on UPLC (Method 08_B4__1) was 8.32 minutes.
Retention time on UPLC (Method 04_A3__1) was 8.69 minutes.

Example 17

$N^{\epsilon 26}$ [(S)-4-Carboxy-4-(15-carboxypentadecanoylamino)butyryl][Aib$^8$,His$^{31}$,Gln$^{34}$]GLP-1(7-37)-peptide (SEQ ID NO: 4)

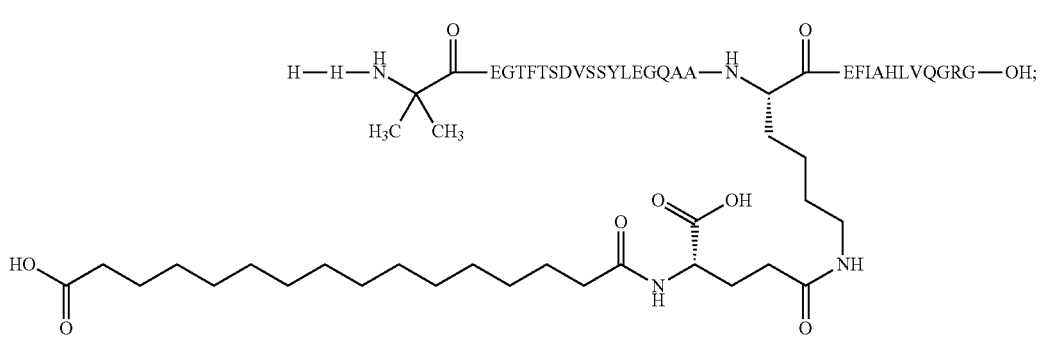

Chem. 36

This compound was prepared as in Example 16.
The theoretical molecular mass of 3716.2 was confirmed by MALDI.
Retention time on UPLC (Method 08_B4__1) was 8.48 minutes.
Retention time on UPLC (Method 04_A3__1) was 9.07 minutes.

Example 18

N⁹-{2-[2-(1H-Imidazol-4-yl)-ethylcarbamoyl]-2-methyl-propionyl}-N^{ε26}-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His³¹,Gln³⁴]GLP-1(9-37)-peptide (SEQ ID NO:9)

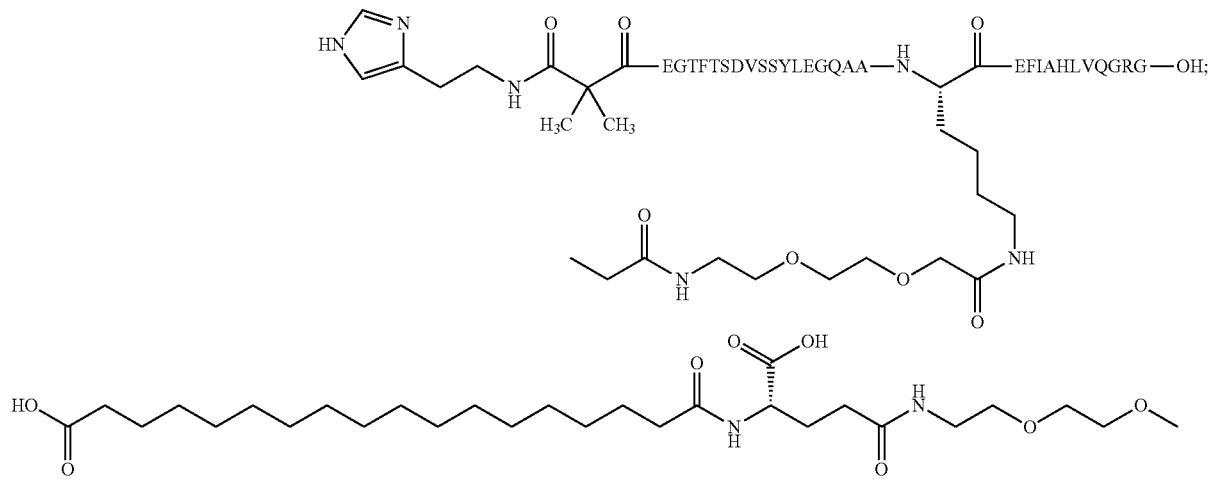

Chem. 37

Preparation method: SPPS method B. 2,2-Dimethyl-N-[2-(1-trityl-1H-imidazol-4-yl)-ethyl]-malonamic acid, Fmoc-Oeg-OH, Fmoc-Glu-OtBu, and octadecanedioic acid mono-tert-butyl ester were coupled using the same coupling condition as an Aib amino acid.
UPLC (method 04_A3_1): Rt=10.16 min
UPLC (method 08_B4_1): Rt=8.76 min
LCMS4: Rt=2.23 min. m/z=1341 (m/3), 1006 (m/4)

Example 19

N^{ε26}[2-(2-{2-[(S)-4-Carboxy-4-(2-{2-[2-(17-carboxy-heptadecanoylamino)ethoxy]ethoxy}acetylamino)butyryl amino]ethoxy}ethoxy)acetyl] [Aib⁸,His³¹,Gln³⁴]GLP-1(7-37)-peptide (SEQ ID NO: 4)

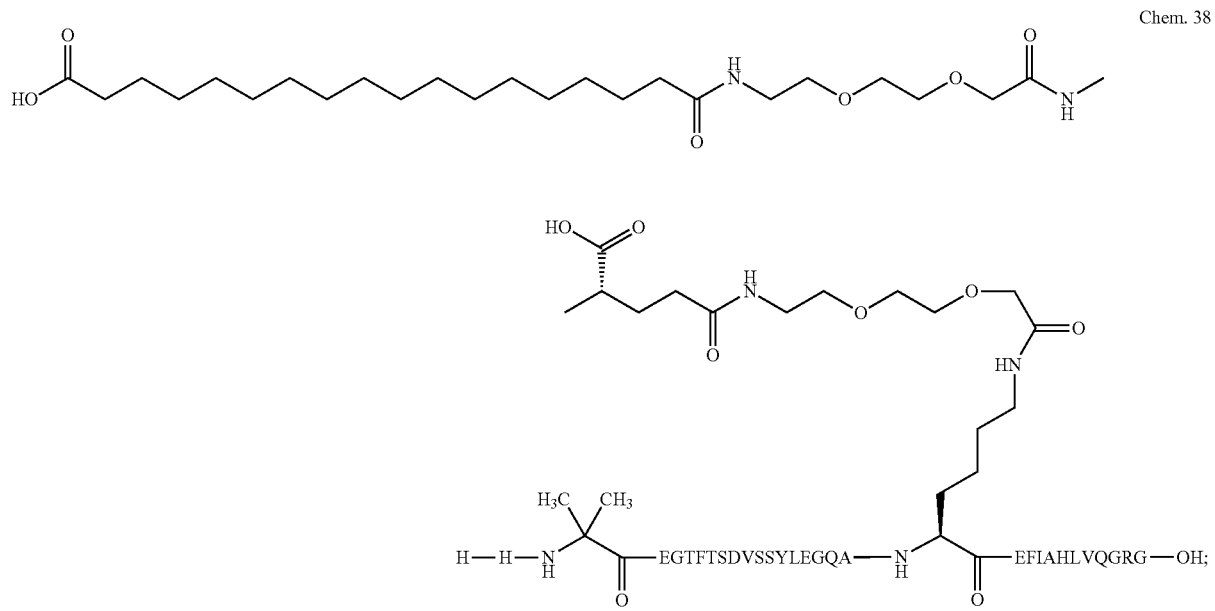

Chem. 38

Preparation method: SPPS method B. Fmoc-Oeg-OH, Fmoc-Glu-OtBu, and octadecanedioic acid mono-tert-butyl ester were coupled using the same coupling condition as an Aib amino acid.
UPLC (method 04_A3_1): Rt=11.9 min
UPLC (method 09_B4_1): Rt=8.67 min
LCMS4: (1010×4)−4=4036, (1346×3)−3=4036.5
Calculated mass=4036

Example 20

$N^{\varepsilon27}$-{2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl}-($Aib^8$,$Glu^{22}$,$Arg^{26}$,$Lys^{27}$,$His^{31}$,$Gln^{34}$) GLP-1(7-37)-peptide (SEQ ID NO: 18)

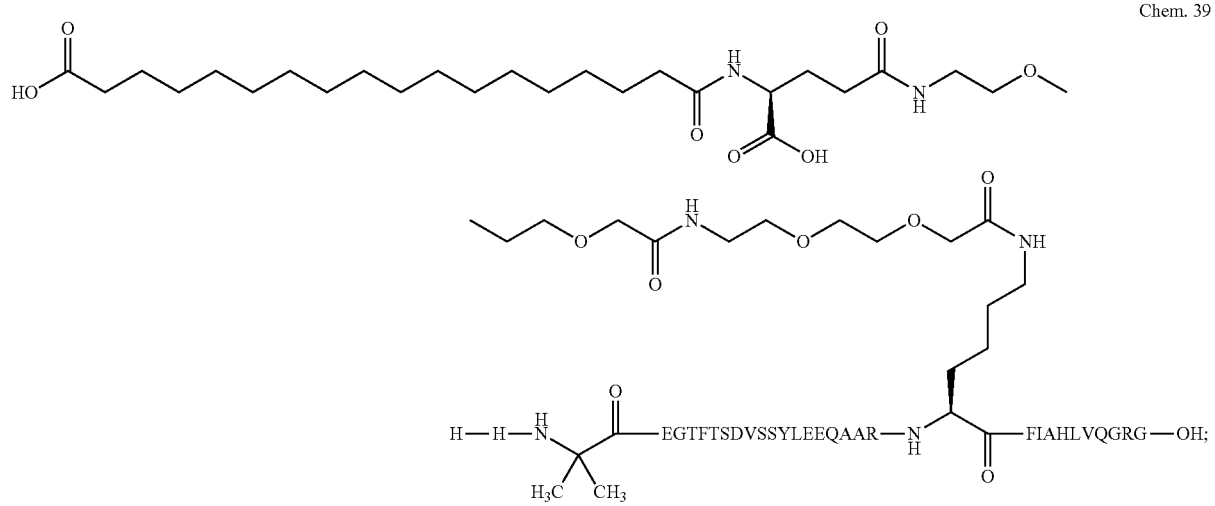

Chem. 39

Preparation method: The peptide was prepared by SPPS method E and the final product was characterised by analytical UPLC and MALDI TOF-MS:
UPLC (method 07_B4_1): Rt=8.2 min
UPLC (method 04_A3_1): Rt=9.9 min
MALDI-MS: 4136
Calculated MW=4135

Example 21

[$Imp^7$,$Glu^{22}$,$Arg^{26}$,$His^{31}$,$Gln^{34}$,$Lys^{37}$]-GLP-1-(7-37)-peptide (SEQ ID NO: 3)

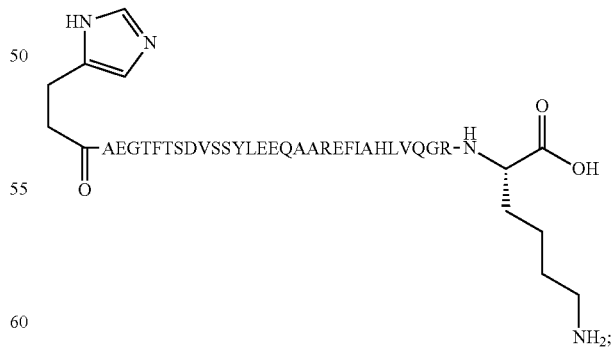

Chem. 40

Preparation method: SPPS method A
UPLC (method 05_B2_1): Rt=9.50 min
UPLC (method 04_A2_1): Rt=13.22 min
LCMS4 (M/4)+1=866; (M/3)+1=1154; Exact mass=4874

Example 22

$N^{\epsilon 37}$-[2-[2-[2-[[2-[2-[2-[[(4R)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Imp$^7$,Glu$^{22}$,Arg$^{26}$, His$^{31}$,Gln$^{34}$,Lys$^{37}$]-GLP-1-(7-37)-peptide (SEQ ID NO: 3)

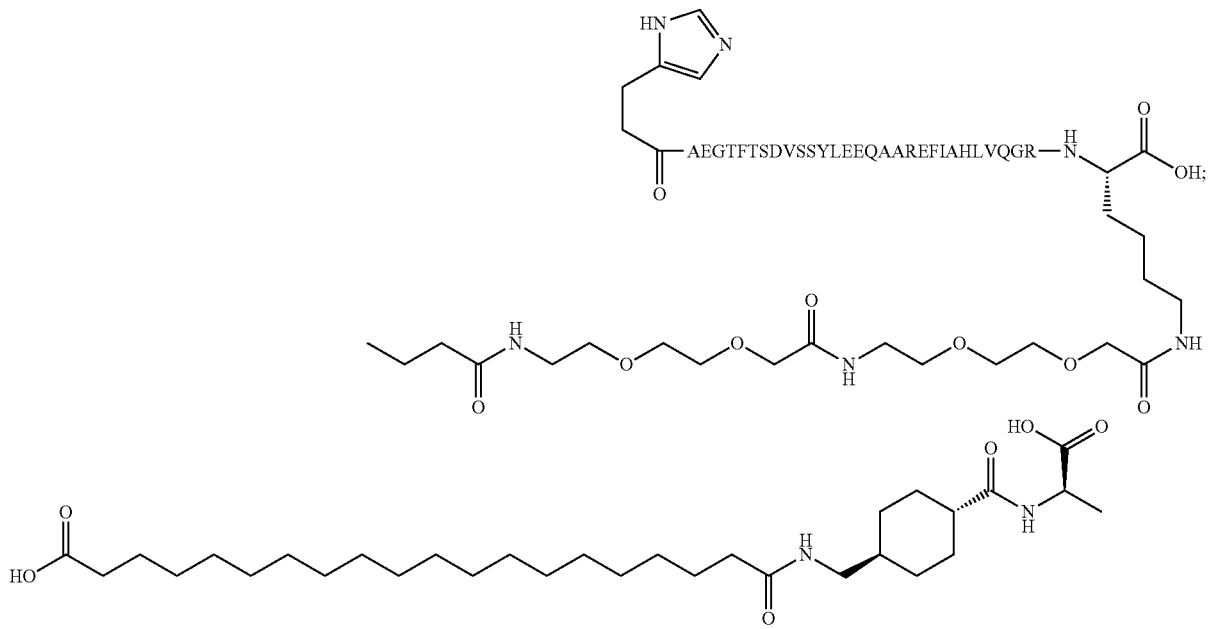

Chem. 41

Preparation method: SPPS method A
UPLC (method 05_B2__1): Rt=14.15 min
UPLC (method 04_A3__1): Rt=11.41 min
LCMS4 (M/5)+1=870; (M/4)+1=1087; Exact mass=4345

Example 23

$N^{\epsilon 36}$-[2-[2-[2-(17-carboxyheptadecanoylamino)ethoxy]ethoxy]acetyl]-[Aib$^8$,Glu$^{30}$,His$^{31}$,Gln$^{34}$, Lys$^{36}$]-GLP-1-(7-37)-peptidyl-Glu amide(SEQ ID NO: 2)

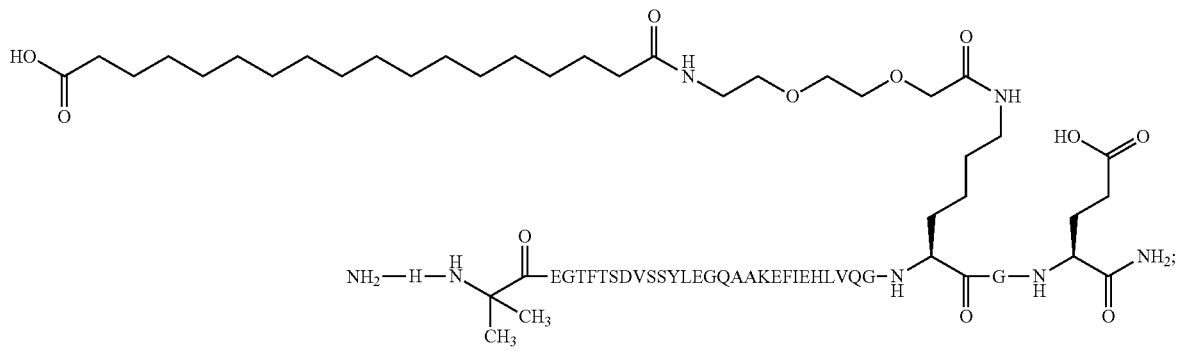

Chem. 42

Preparation method: SPPS method A
UPLC (method 05_B2_1): Rt=13.32 min
UPLC (method 04_A3_1): Rt=10.14 min
LCMS4 (M/5)+1=785; (M/4)+1=981; Exact mass=3920

Example 24

N$^\alpha$([Aib$^8$,His$^{31}$,Gln$^{34}$]-GLP-1-(7-37)-peptidyl)-Lysine(SEQ ID NO: 6)

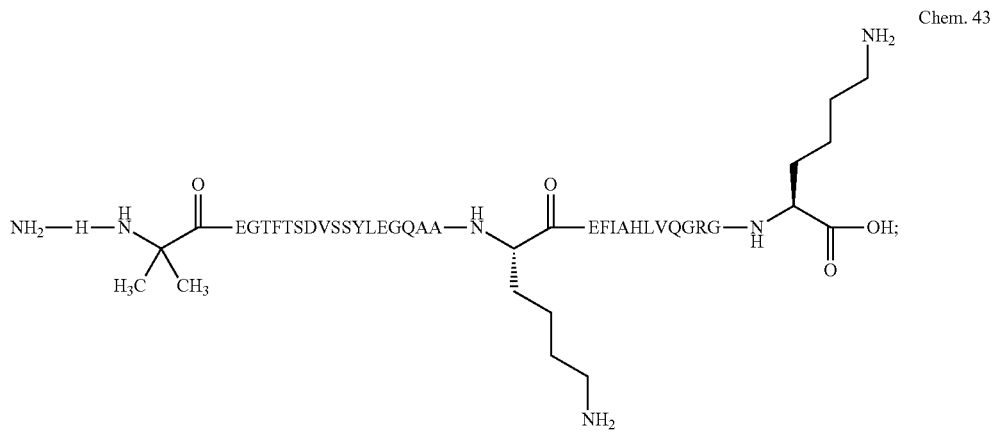

Chem. 43

Preparation method: SPPS method A
UPLC (method 08_B2_1): Rt=9.30 min
UPLC (method 04_A2_1): Rt=15.55 min
LCMS4 (M/5)+1=690; (M/4)+1=863; Exact mass=3449

Example 25

[Aib$^8$,His$^{31}$,Gln$^{34}$,Lys$^{37}$]-GLP-1-(7-37)-peptide (SEQ ID NO: 8)

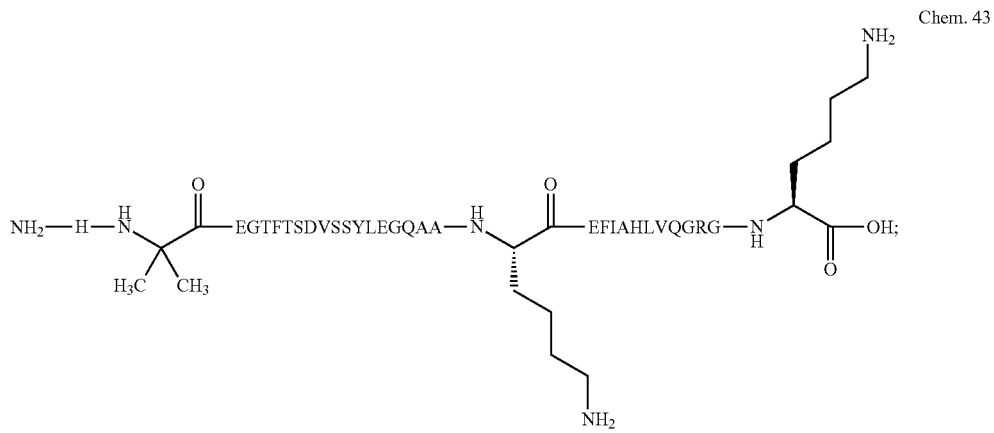

Chem. 43

Preparation method: SPPS method A
UPLC (method 08_B2_1): Rt=9.28 min
LCMS4 (M/5)+1=679; (M/4)+1=849; Exact mass=3449

Example 26

$N^{\epsilon 26}$-[(4S)-4-carboxy-4-(tetradecanoylamino)butanoyl], $N^{\epsilon 37}$-[(4S)-4-carboxy-4-(tetradecanoylamino)butanoyl]-[Aib$^8$,His$^{31}$,Gln$^{34}$,Lys$^{37}$]-GLP-1-(7-37)-peptide (SEQ ID NO: 8)

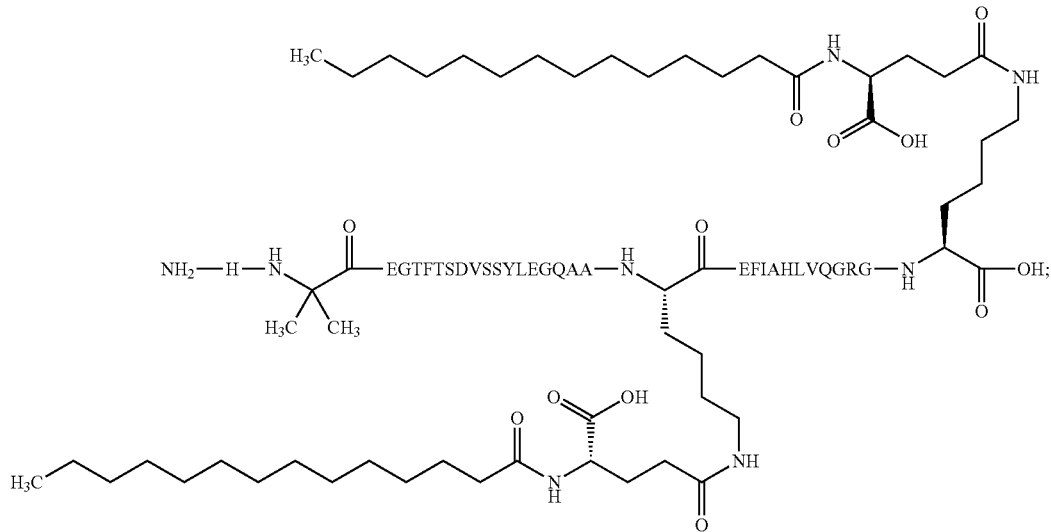

Chem. 45

Preparation method: SPPS method A
UPLC (method 08_B4_1): Rt=11.76 min
LCMS4 (M/5)+1=815; (M/4)+1=1018; Exact mass=4071

Example 27

$N^{\epsilon 12}$-12-[2-[2-[2-[[2-[2-[2-(17-carboxyheptadecanoylamino)ethoxy]ethoxy]acetyl]amino]ethoxy]ethoxy]acetyl]-[Lys$^{12}$,Glu$^{22}$,Arg$^{26}$,His$^{31}$,Gln$^{34}$]-GLP-1-(7-37)-peptide (SEQ ID NO: 11)

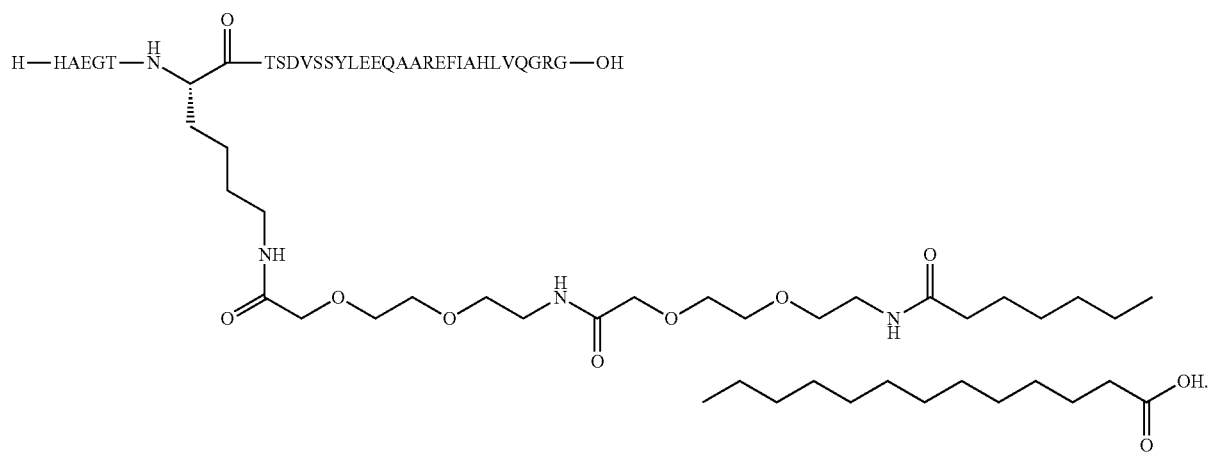

Chem. 46

Preparation method: SPPS method B
UPLC (method 09_B4_1): Rt=8.08 min
UPLC (method 04_A6_1): Rt=6.01 min
LCMS4: Rt=1.85 min. m/z: 3975; M/4=994; M/5=795

Example 28

N$^{\epsilon 26}$-[2-(2-[2-(2-[2-(2-[4-(10-(4-Carboxyphenoxy) decanoylamino)-4(S)-carboxybutyrylamino]ethoxy) ethoxy]acetylamino)ethoxy]ethoxy)acetyl]-N$^{\epsilon 37}$-[2-(2-[2-(2-[2-(2-[4-(10-(4-Carboxyphenoxy) decanoylamino)-4(S)-carboxybutyrylamino]ethoxy) ethoxy]acetylamino) ethoxy]ethoxy)acetyl][Aib$^8$, His$^{31}$,Gln$^{34}$,Lys$^{37}$]GLP-1(7-37)-peptide (SEQ ID NO: 8)

Chem. 47
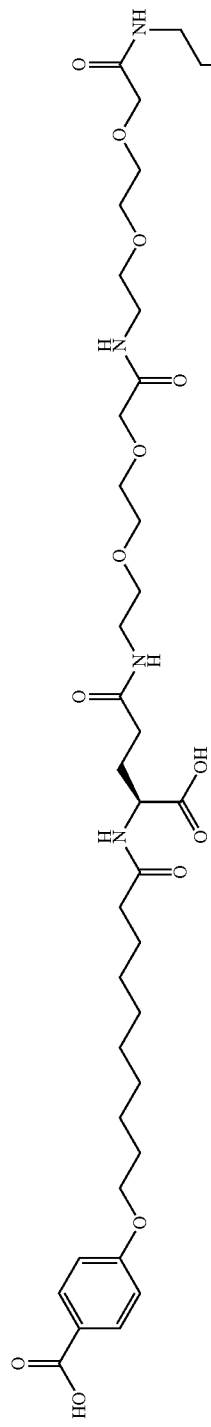
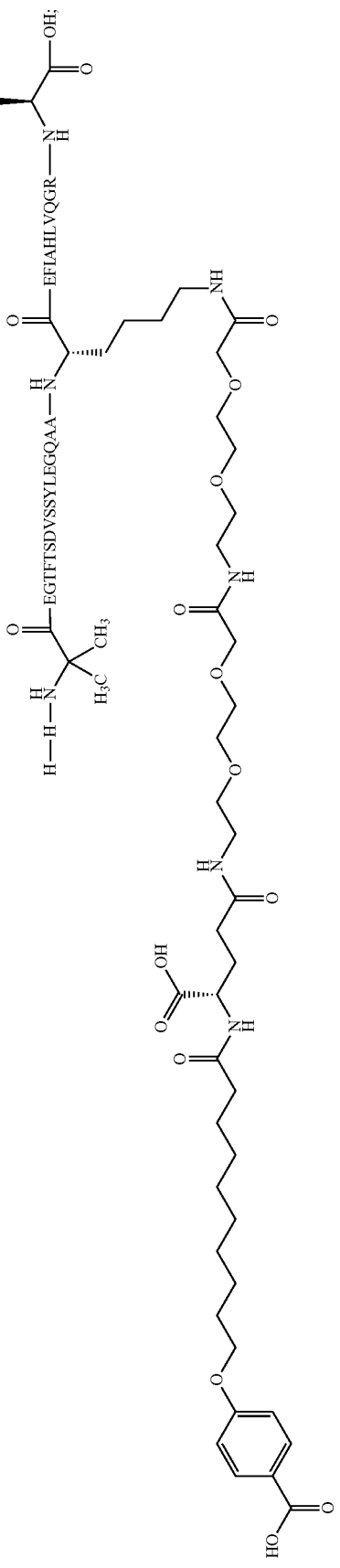

Preparation: SPPS method A, starting with low-load Fmoc-Lys(Mtt)-Wang resin. Fmoc-Lys(Mtt)-OH was used in position 26, and Boc-His(trt)-OH was used in position 7. The Mtt was removed with HFIP, and 8-(9-fluorenylmethyloxycarbonyl-amino)-3,6-dioxaoctanoic acid (commercially available from Iris Biotech) was coupled twice followed by Fmoc-Glu-OtBu and 4-(9-carboxy-nonyloxy)-benzoic acid tert-butyl ester (prepared as described in Example 25, step 2 of WO 2006/082204) were coupled using SPPS method A.
UPLC (method 05_B5_1): Rt=4.95 min (92%)
LCMS4: m/z=4011, calculated=4011

Example 29

$N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl] [Aib$^8$,His$^{31}$,Gln$^{34}$,Lys$^{37}$]GLP-1(7-37)-peptide (SEQ ID NO: 8)

Chem. 48

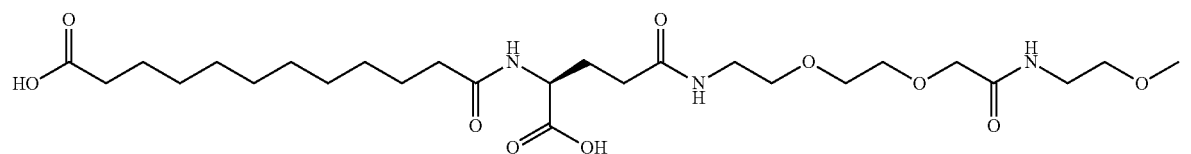

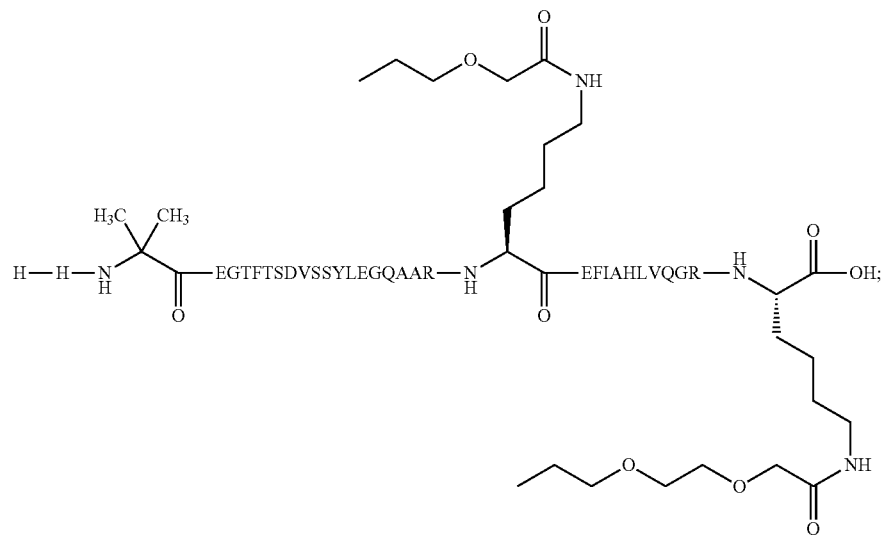

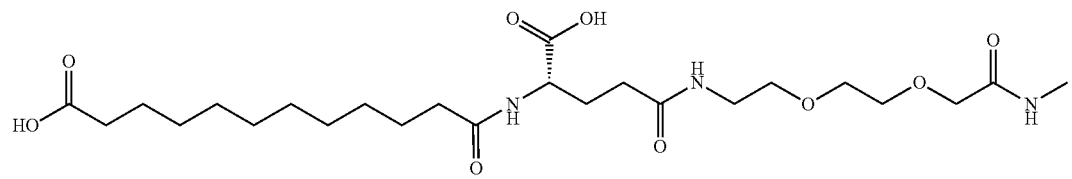

Preparation method: As in Example 16 except that Lys(Mtt)-Wang resin with a loading of 0.35 mmol/g was used.
The theoretical molecular mass of 4655.2 was confirmed by MALDI
UPLC (method 08_B4_1): Rt 7.72 min
UPLC (method 04_A3_1): Rt 5.70 min

Example 30

$N^{\varepsilon 26}$-2,3-bis[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]propanoyl-[Aib$^8$,His$^{31}$,Gln$^{34}$]-GLP-1-(7-37)-peptide (SEQ ID NO: 4)

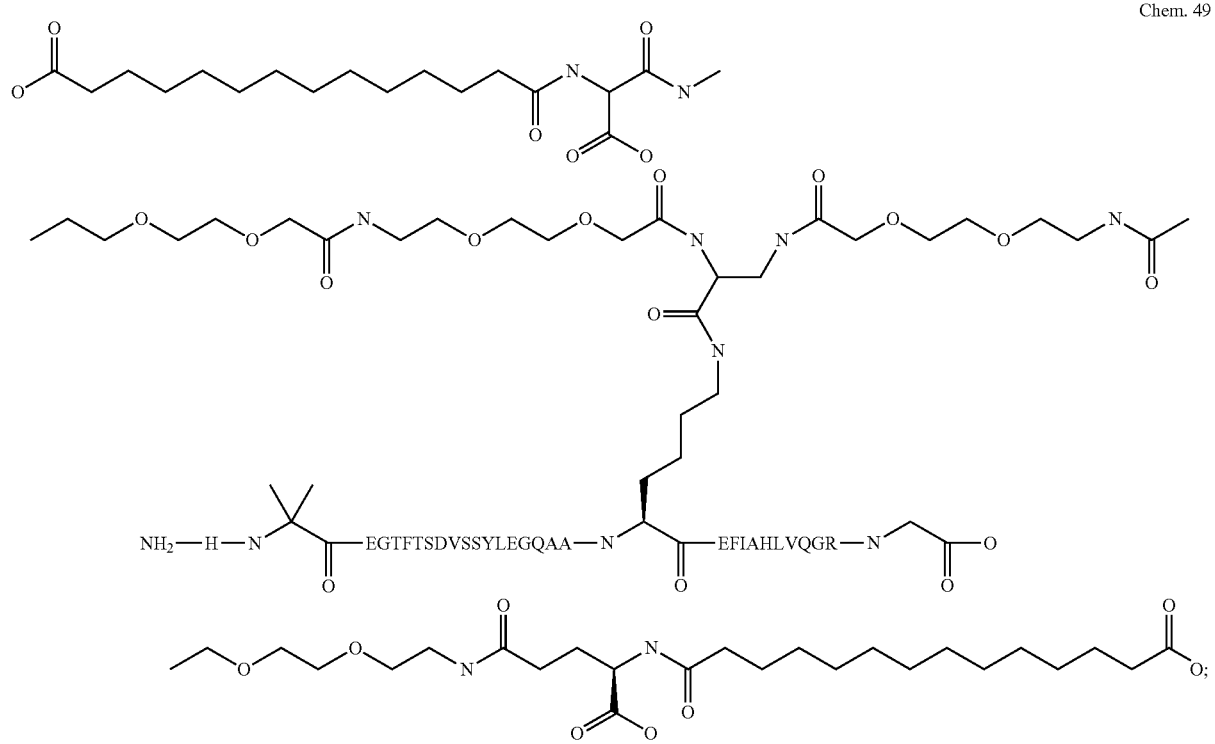

Chem. 49

Preparation method: SPPS method B
UPLC (method 08_B4_1): Rt=8.12 min
UPLC (method 04_A3_1): Rt=7.12 min
LCMS_4: Rt=1.42 min. m/z: 4727; M/3=1575; M/4=1182

Example 31

$N^{\varepsilon 8}$-18-[2-[2-[2-[[2-[2-[2-[[(4S)-4-carboxy-4-[[1-(19-carboxynonadecanoyl)piperidine-4-carbonyl]amino]butanoyl]amino]ethoxy]ethoxy]acetyl]amino]ethoxy]ethoxy]acetyl]-[Aib$^8$,Lys$^{18}$,Glu$^{22}$,His$^{26}$,His$^{31}$,Gln$^{34}$]-GLP-1-(7-37)-peptide (SEQ ID NO: 13)

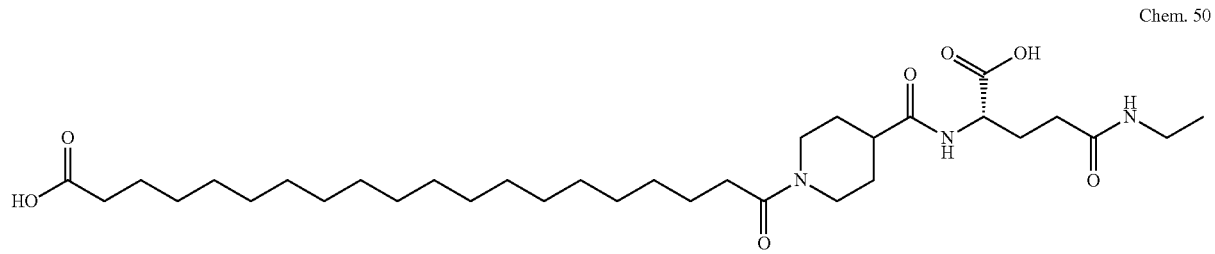

Chem. 50

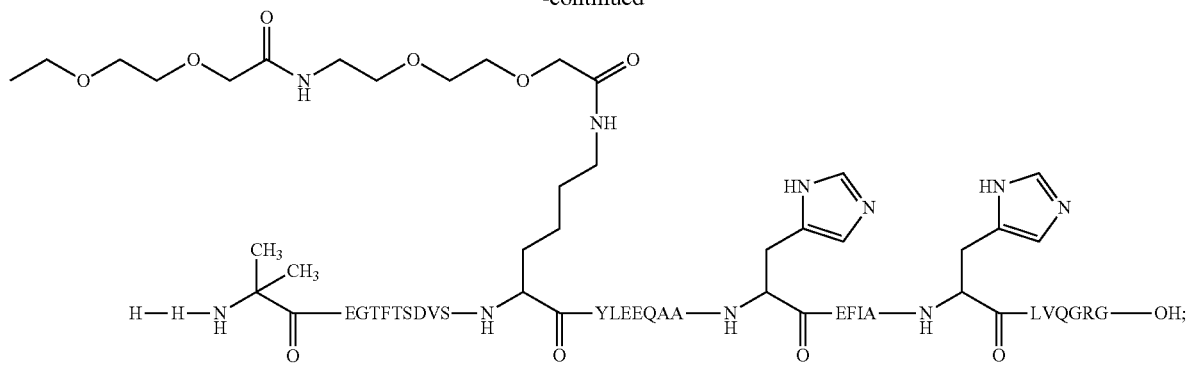

Preparation method: SPPS method B
LCMS4: Rt=3.62 min, m/z: 4297.0
UPLC (method 08_B2_1): Rt=12.25 min
UPLC (method 04_A3_1): Rt=10.68 min Example 32

$N^{\epsilon 27}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$, Glu$^{22}$,Arg$^{26}$,Lys$^{27}$,Glu$^{30}$,His$^{31}$,Gln$^{34}$,Pro$^{37}$]-GLP-1-(7-37)-peptide (SEQ ID NO: 19)

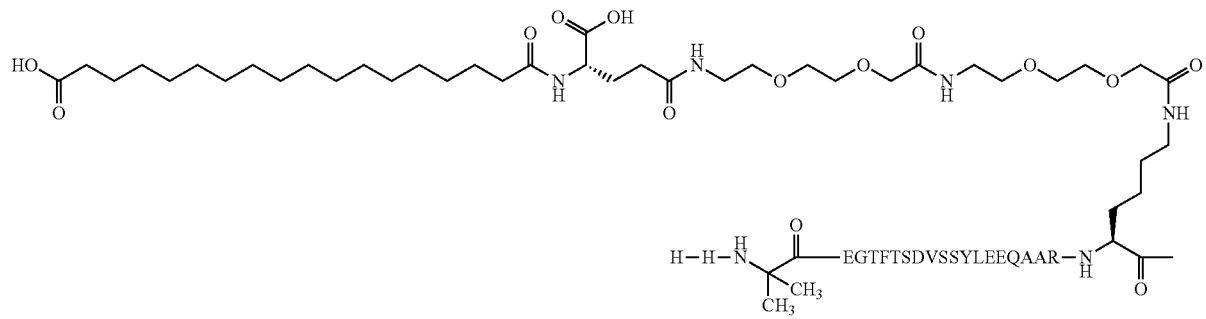

Chem. 51

Preparation method: SPPS method B
The theoretical molecular mass of 4234 was confirmed by MALDI-MS (alpha-cyano-4-hydroxy cinnamic acid); m/z: 4234 (1A)
UPLC (method 07_B4_1): Rt=8.3 min
UPLC (method 04_A3_1): Rt=9.2 min

Example 33

$N^{\epsilon 26}$-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl][His$^{31}$, Gln$^{34}$]-GLP-1-(7-37)-peptide (SEQ ID NO: 9)

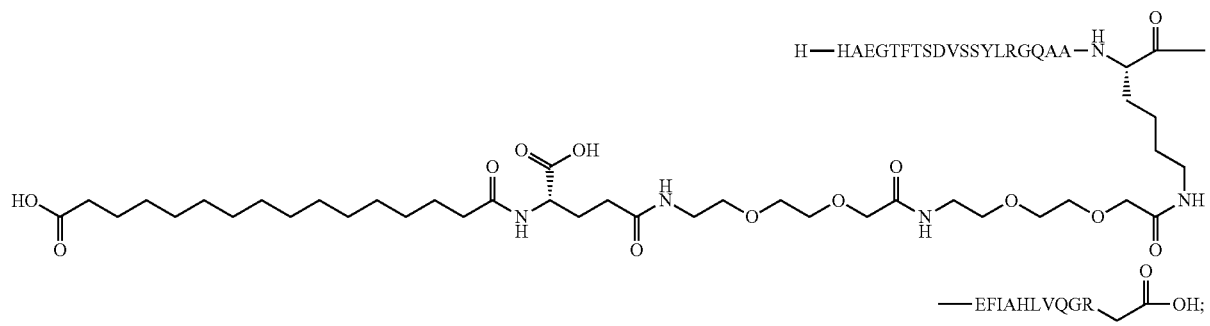

Chem. 52

Preparation method: SPPS method B
LCMS4: Rt=1.94 min, m/z: 3994.5
UPLC (method 08_B2__1): Rt=12.25 min
UPLC (method 04_A3__1): Rt=8.63 min

Example 34

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]a cetyl][His$^{31}$,Gln$^{34}$,Lys$^{37}$]-GLP-1-(7-37)-peptide (SEQ ID NO: 20)

Chem. 53
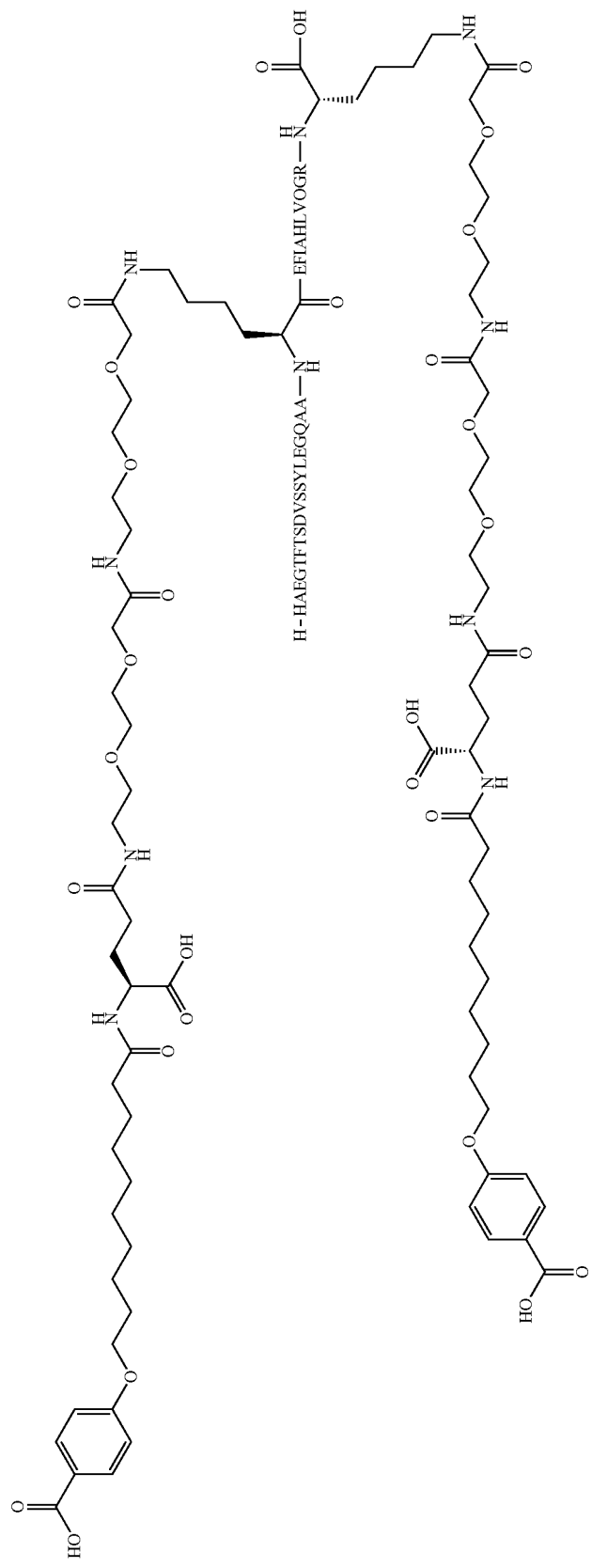

Preparation method: SPPS method B
LCMS4 Rt: =1.92 min m/z: 4797.3; M/4: 1199.8; M/3: 1599.4
UPLC (method 09_B4_1): Rt=8.12 min
UPLC (method: 05_B8_1): Rt=2.03 min

Example 35

$N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[His$^{31}$, Gln$^{34}$,Lys$^{37}$]-GLP-1-(7-37)-peptide (SEQ ID NO: 20)

Chem. 54

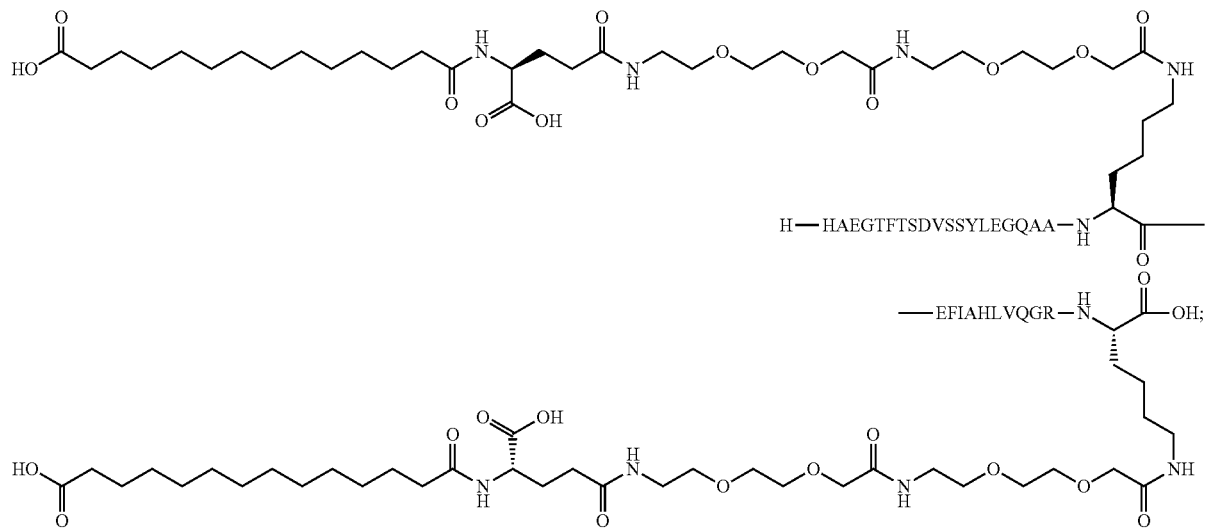

Preparation method: SPPS method B
LCMS4: Rt=1.99 min, m/z: 4697.0
UPLC (method 09_B2_1): Rt=12.20 min
UPLC (method 05_B5_1): Rt=5.31 min

Example 36

$N^{\epsilon 26}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[His$^{31}$, Gln$^{34}$,Lys$^{37}$]-GLP-1-(7-37)-peptide (SEQ ID NO: 20)

Chem. 55

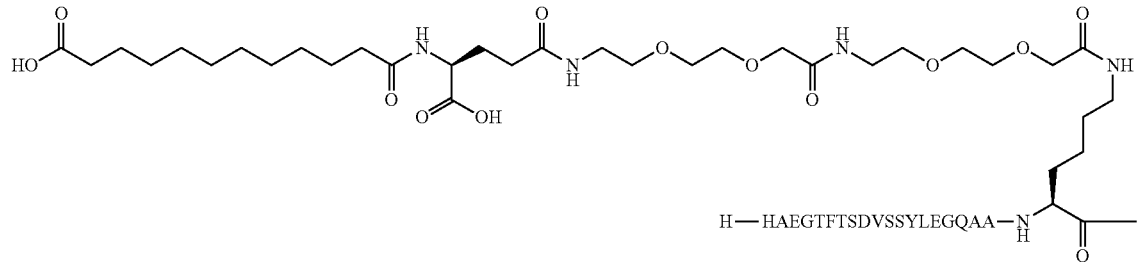

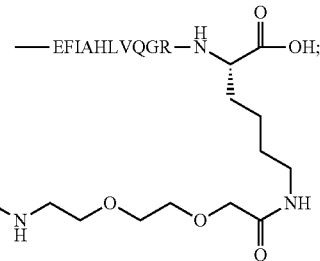
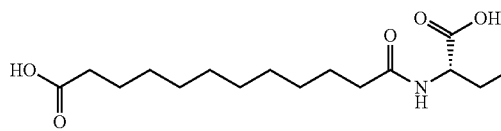

Preparation method: SPPS method B
LCMS4: Rt=1.89 min, m/z: 4641.2
UPLC (method 09_B2_1): Rt=11.20 min
UPLC (method 05_B5_1): Rt=4.00 min Example 37

$N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 37}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl][His$^{31}$,Gln$^{34}$,Lys$^{37}$]-GLP-1-(7-37)-peptide (SEQ ID NO: 20)

Chem. 56
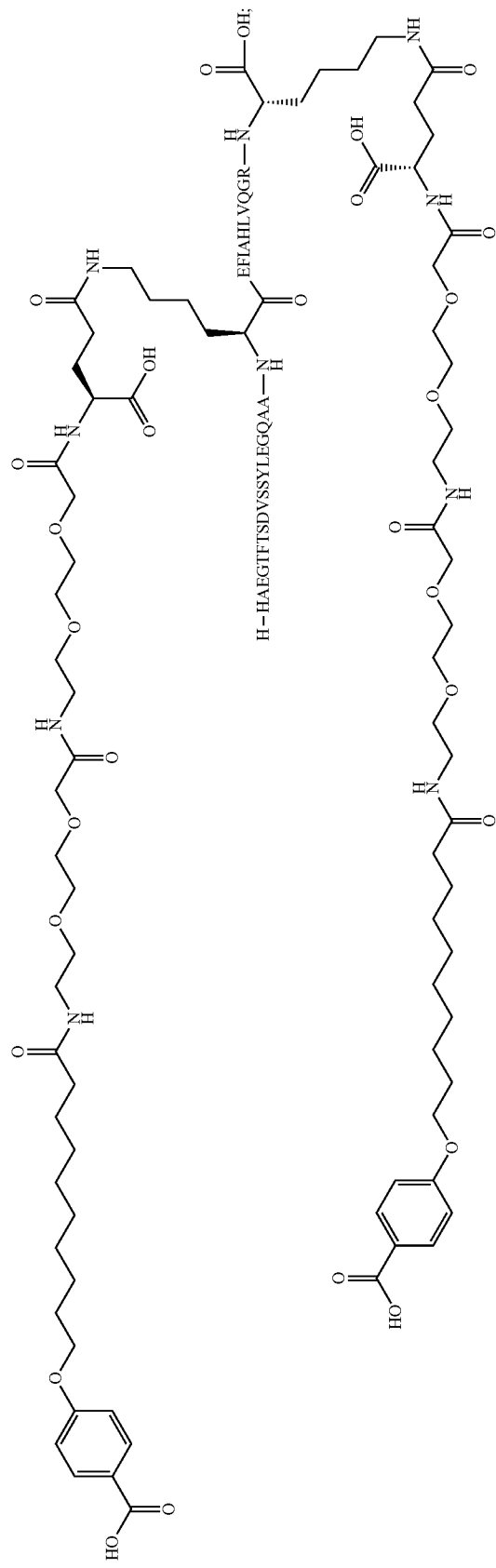

Preparation method: SPPS method B
LCMS4 Rt=1.97 min m/z: 4797.3; M/4: 1200.1; M/5: 1599.8
UPLC (method 09_B4_1): Rt=8.24 min
UPLC (method 05_B8_1): Rt=2.88 min Example 38

$N^{\epsilon 26}$-4-[16-(1H-tetrazol-5-yl)hexadecanoylsulfamoyl]butanoyl-[His$^{31}$,Gln$^{34}$]-GLP-1-(7-37)-peptide (SEQ ID NO: 9)

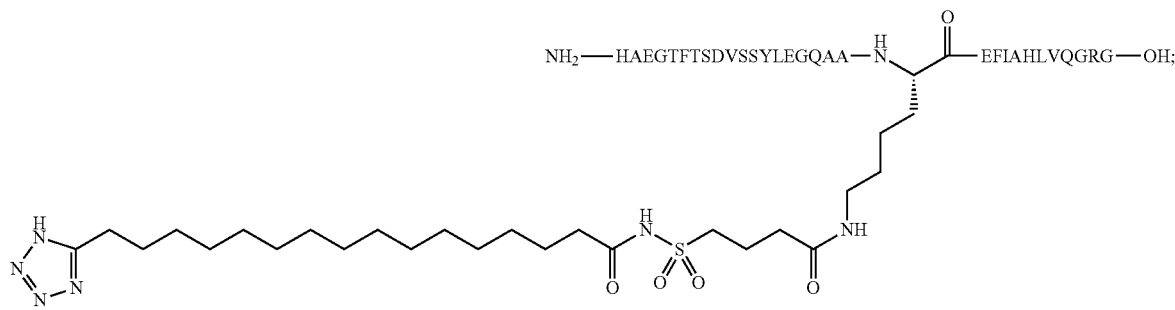

Chem. 57

Preparation method: SPPS method A
UPLC (method 09_B2_1): Rt=8.29 min
UPLC (method 05_B5_1): Rt=6.40 min
LCMS4 m/z: 3762

Example 39

$N^{8}$-methyl, $N^{\epsilon 26}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl][His$^{31}$,Gln$^{34}$]-GLP-1-(7-37)-peptide (SEQ ID NO: 9)

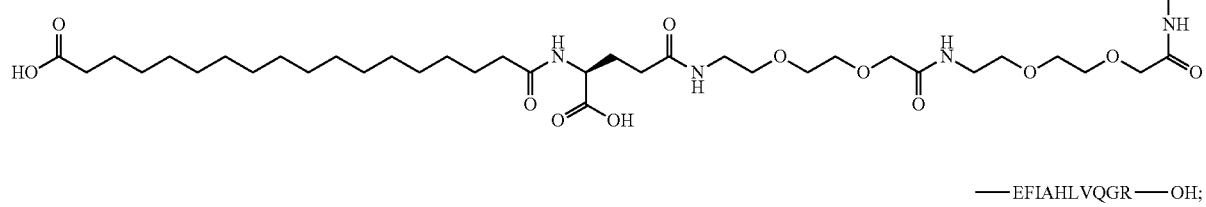

Chem. 58

Preparation method: SPPS method B

The theoretical molecular mass of 4037 was confirmed by MALDI-MS (alpha-cyano-4-hydroxy cinnamic acid); m/z: 4035 (1A)

UPLC (method 05_B5_1): Rt=5.8 min
UPLC (method 07_B4_1): Rt=8.5 min

Example 40

N$^{\epsilon 22}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys$^{22}$, Arg$^{26}$,His$^{31}$,Gln$^{34}$]-GLP-1-(7-37)-peptide (SEQ ID NO: 21)

Chem. 59

Preparation method: SPPS method B
LCMS4: Rt=1.89 min, m/z: 4121.6
UPLC (method 09_B2__1): Rt=11.97 min
UPLC (method 05_B5__1): Rt=5.30 min

Example 41

N$^{\epsilon 24}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^{8}$, Glu$^{22}$,Lys$^{24}$,Arg$^{26}$,His$^{31}$,Gln$^{34}$]-GLP-1-(7-37)-peptide (SEQ ID NO: 22)

Chem. 60

Preparation method: SPPS method B
UPLC (method 08_B4__1): Rt=7.9 min
UPLC (method 05_B8__1): Rt=3.11 min
MALDI-MS (alpha-cyano-4-hydroxy cinnamic acid): m/z: 4194

Example 42

N$^{\epsilon 27}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$, Ile$^{25}$,Arg$^{26}$,Lys$^{27}$,His$^{31}$,Gln$^{34}$]-GLP-1-(7-37)-peptide (SEQ ID NO: 23)

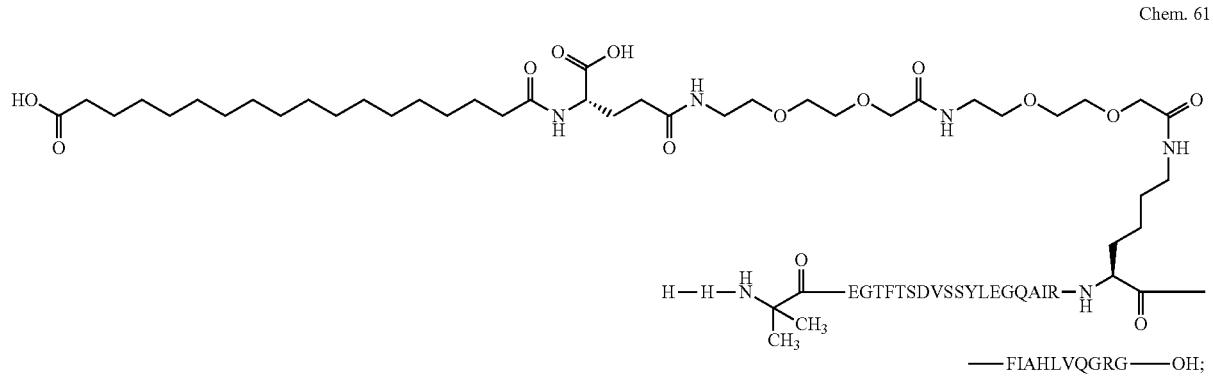

Chem. 61

Preparation method: SPPS method B
The theoretical molecular mass of 4106 was confirmed by MALDI-MS (alpha-cyano-4-hydroxy cinnamic acid); m/z: 4105 (1A)
UPLC (method 07_B4_1): Rt=8.5 min

Example 43

N$^{\epsilon 16}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$, Lys$^{16}$,Glu$^{22}$,Arg$^{26}$,His$^{31}$,Gln$^{34}$]-GLP-1-(7-37)-peptide (SEQ ID NO: 24)

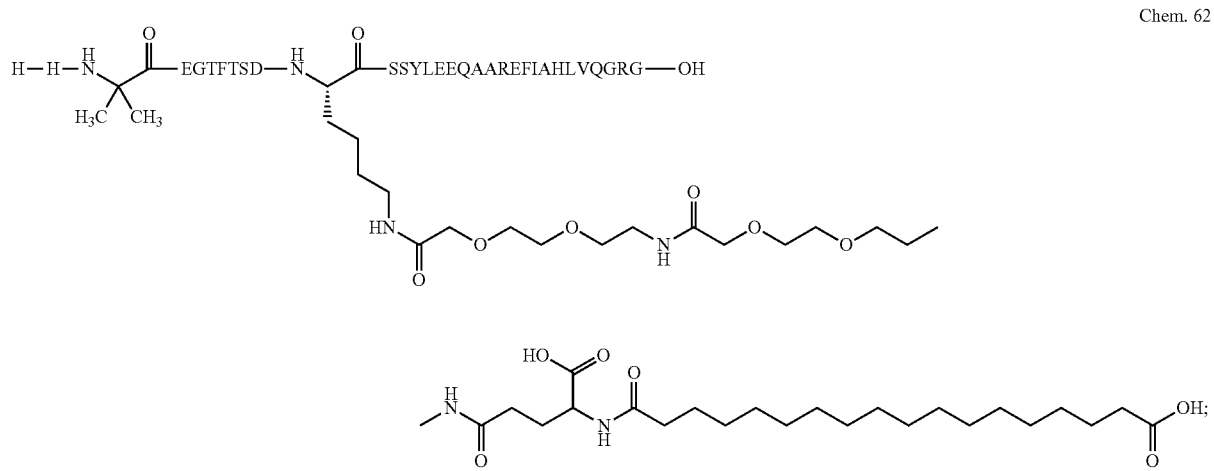

Chem. 62

Preparation method: SPPS method B
UPLC (method 08_B4_1): Rt=8.06 min
LCMS4: (M/5)+1=834; (M/4)+1=1042; Exact mass=4167

Example 44

$N^{\epsilon 26}$-[(4S)-4-carboxy-4-(15-carboxypentadecanoyl-amino)butanoyl]-[His$^{31}$,Gln$^{34}$]-GLP-1-(7-37)-peptide (SEQ ID NO: 9)

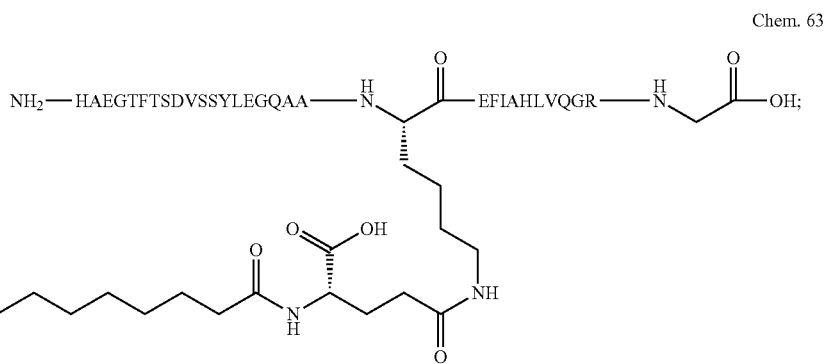

Chem. 63

Preparation method: SPPS method A
UPLC (method 10_B14__1): Rt=6.66 min
LCMS4 (M/4)+1=927; (M/3)+1=1235; Exact mass=3704

Example 45

$N^{\epsilon 26}$-[(4S)-4-carboxy-4-(hexadecanoylamino)butanoyl]-[His$^{31}$,Gln$^{34}$]-GLP-1-(7-37)-peptide (SEQ ID NO: 9)

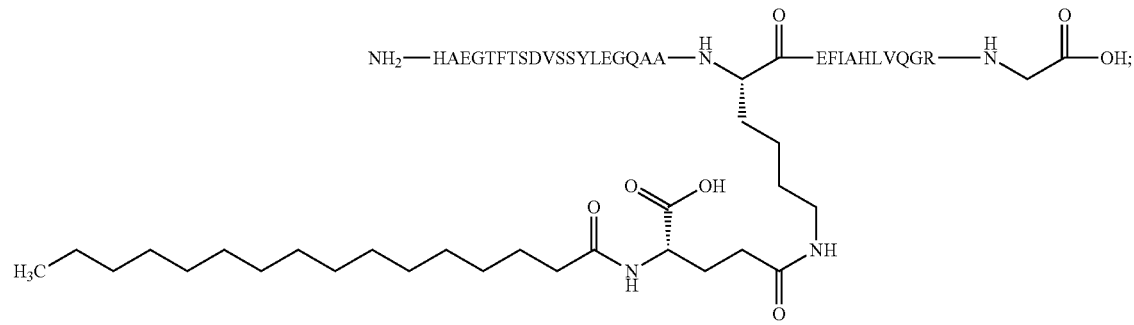

Chem. 64

Preparation method: SPPS method A
UPLC (method 10_B14__1): Rt=10.13 min
LCMS4 (M/4)+1=913; (M/3)+1=1226; Exact mass=3675

Example 46

$N^{\epsilon2}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys$^{12}$, Glu$^{22}$,Arg$^{26}$,His$^{31}$,Gln$^{34}$]-GLP-1-(7-37)-peptide
(SEQ ID NO: 11)

Chem. 65

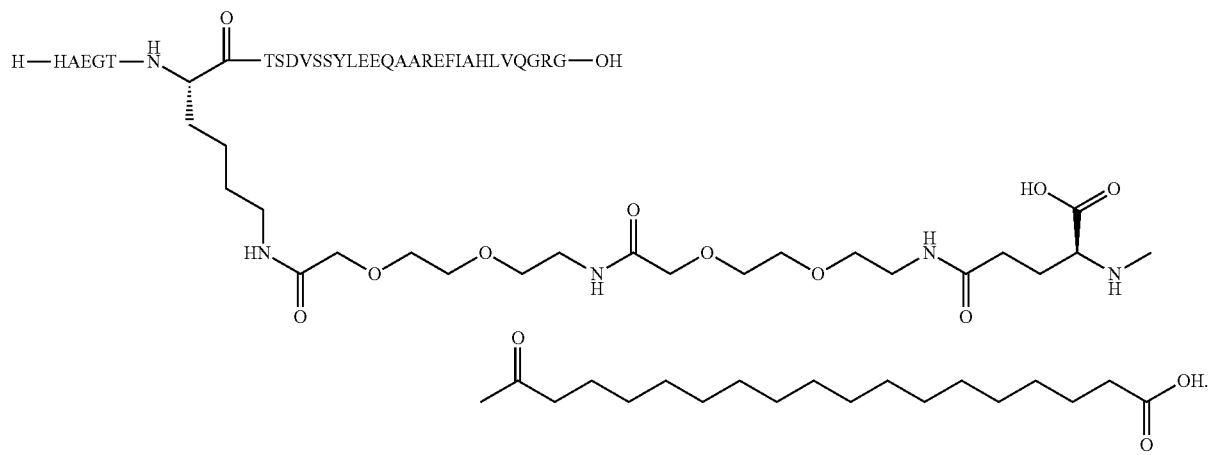

Preparation method: SPPS method B
UPLC (method 08_B4_1): Rt=7.76 min
MALDI-MS (alpha-cyano-4-hydroxy cinnamic acid): m/z: 4102

Example 47

$N^{\epsilon24}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Glu$^{22}$, Lys$^{24}$,Arg$^{26}$,His$^{31}$,Gln$^{34}$]-GLP-1-(7-37)-peptide
(SEQ ID NO: 25)

Chem. 66

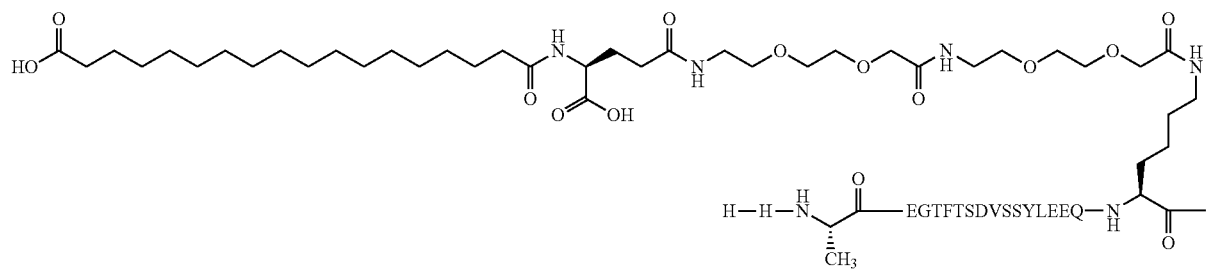

Preparation method: SPPS method B
UPLC (method 08_B4_1): Rt=7.78 min
MALDI-MS (alpha-cyano-4-hydroxy cinnamic acid): m/z: 4178

Pharmacological Methods

Example 48

In Vitro Potency

The purpose of this example is to test the activity, or potency, of the GLP-1 compounds of the invention in vitro.

The potencies of the GLP-1 analogues and derivatives of Examples 1-47 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 analogue or derivative in question, and the potency of cAMP production was measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 5% FCS, 1% Pen/Strep (Penicillin/Streptomycin) and 0.5 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in 10 ml of Buffer 1 (20 mM Na-HEPES, 10 mM EDTA, pH=7.4), centrifuged 15 min at 20.000 rpm and the pellet resuspended in 10 ml of Buffer 2 (20 mM Na-HEPES, 0.1 mM EDTA, pH=7.4). The suspension was homogenised for 20-30 sec and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in ½-area 96-well plates, flat bottom (Costar cat. no: 3693). The final volume per well was 50 µl.

Solutions and Reagents

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and
Biotinylated-cAMP (133 U/µl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% TWEEN™ polysorbate surfactant (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 uM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 analogue or derivative to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3 \times 10^{-11}$ of cAMP.

Membrane/Acceptor Beads

Use hGLP-1/BHK 467-12A membranes; 6 µg/well corresponding to 0.6 mg/ml (the amount of membranes used pr. well may vary)

"No membranes": Acceptor Beads (15 µg/ml final) in AlphaScreen buffer

"6 µg/well membranes": membranes+Acceptor Beads (15 µg/ml final) in AlphaScreen buffer Add 10 µl "No membranes" to the cAMP standard (per well in duplicates) and the positive and negative controls Add 10 µl "6 µg/well membranes" to GLP-1 and analogues (per well in duplicates/triplicates)

Pos. Control: 10 µl "no membranes"+10 µl AlphaScreen Buffer

Neg. Control: 10 µl "no membranes"+10 µl cAMP Stock Solution (50 µM)

As the beads are sensitive to direct light, any handling was in the dark (as dark as possible), or in green light. All dilutions were made on ice.

Procedure

1. Make the AlphaScreen Buffer.
2. Dissolve and dilute the GLP-1/Analogues/cAMP standard in AlphaScreen Buffer.
3. Make the Donor Beads solution and incubate 30 min. at R.T.
4. Add the cAMP/GLP-1/Analogues to the plate: 10 µl per well.
5. Prepare membrane/Acceptor Beads solution and add this to the plates: 10 µl per well.
6. Add the Donor Beads: 30 µl per well.
7. Wrap the plate in aluminum foil and incubate on the shaker for 3 hours (very slowly) at RT.
8. Count on AlphaScreen—each plate pre incubates in the AlphaScreen for 3 minutes before counting.

Results

The $EC_{50}$ [pM] values were calculated using the GraphPad Prism software (version 5), The potency of all compounds, analogues and derivatives, in vitro was confirmed. 44 compounds had a good in vitro potency corresponding to an $EC_{50}$ of 2000 pM or below; 40 compounds were even more potent having an $EC_{50}$ at 1000 pM or below; 33 compounds had a still further improved potency corresponding to an $EC_{50}$ at 500 pM or below; 21 compounds were very potent corresponding to an $EC_{50}$ at 200 pM or below; and 13 compounds had a very good potency corresponding to an $EC_{50}$ at 100 pM or below. The $EC_{50}$ of the five analogues was in the range of 40-160 pM.

If desired, the fold variation in relation to GLP-1 may be calculated as $EC_{50}$ (GLP-1)/$EC_{50}$ (analogue)–3693.2.

Example 49

GLP-1 Receptor Binding

The purpose of this experiment is to investigate the binding to the GLP-1 receptor of the GLP-1 compounds of the invention, and how the binding is potentially influenced by the presence of albumin. This is done in an in vitro experiment as described below.

The binding affinity of the GLP-1 analogues and derivatives of Examples 1-47 to the human GLP-1 receptor was measured by way of their ability to displace of $^{125}$I-GLP-1 from the receptor. In order to test the binding of the compounds to albumin, the assay was performed with a low concentration of albumin (0.005%—corresponding to the residual amount thereof in the tracer), as well as with a high concentration of albumin (2.0% added).

A shift in the binding affinity, $IC_{50}$, is an indication that the peptide in question binds to albumin, and thereby a prediction of a potential protracted pharmacokinetic profile of the peptide in question in animal models.

Conditions

Species (in vitro): Hamster
Biological End Point: Receptor Binding
Assay Method: SPA
Receptor: GLP-1 receptor
Cell Line: BHK tk-ts13

Cell Culture and Membrane Purification

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

The cells (approx. 80% confluence) were washed twice in PBS and harvested with Versene (aqueous solution of the tetrasodium salt of ethylenediaminetetraacetic acid), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate was centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at minus 80° C.

Buffer 1: 20 mM Na-HEPES+10 mM EDTA, pH 7.4
Buffer 2: 20 mM Na-HEPES+0.1 mM EDTA, pH 7.4
Binding Assay:
SPA:

Test compounds, membranes, SPA-particles and [$^{125}$I]-GLP-1(7-36)NH$_2$ were diluted in assay buffer. 25 ul (micro liter) of test compounds were added to Optiplate. HSA ("high albumin" experiment containing 2% HSA), or buffer ("low albumin" experiment containing 0.005% HSA), was added (50 ul). 5-10 ug protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with [$^{125}$I]-GLP-1]-(7-36)NH$_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.

Assay Buffer:
50 mM HEPES
5 mM EGTA
5 mM MgCl2
0.005% TWEEN™ polysorbate-20
pH 7.4
HSA was SIGMA A1653

Calculations

The IC$_{50}$ value was read from the curve as the concentration which displaces 50% of $^{125}$I-GLP-1 from the receptor, and the ratio of [(IC$_{50}$/nM) high HSA]/[(IC$_{50}$/nM) low HSA] was determined.

Generally, the binding to the GLP-1 receptor at low albumin concentration should be as good as possible, corresponding to a low IC$_{50}$ value.

The IC$_{50}$ value at high albumin concentration is a measure of the influence of albumin on the binding of the compound to the GLP-1 receptor. As is known, the GLP-1 derivatives also bind to albumin. This is a generally desirable effect, which extends their lifetime in plasma. Therefore, for the derivatives, the IC$_{50}$ value at high albumin will generally be higher than the IC$_{50}$ value at low albumin, corresponding to a reduced binding to the GLP-1 receptor, caused by albumin binding competing with the binding to the GLP-1 receptor.

A high ratio (IC$_{50}$ value (high albumin)/IC$_{50}$ value (low albumin)) may therefore be taken as an indication that the derivative in question binds well to albumin (may have a long half-life), and also per se binds well to the GLP-1 receptor (the IC$_{50}$ value (high albumin) is high, and the IC$_{50}$ value (low albumin) is low).

Results

The following results were obtained, where "ratio" refers to [(IC$_{50}$/nM) high HSA]/[(IC$_{50}$/nM) low HSA]):

Except for the five analogues and two of the derivatives, all compounds had a ratio above 1.0; 35 derivatives were above 10; 27 derivatives were above 25; 23 derivatives were above 50; 13 derivatives above 100; and 7 derivatives had a ratio above 250.

Furthermore as regards IC$_{50}$ (low albumin), all compounds had an IC$_{50}$ (low albumin) below 600 nM; all but one below 500 nM; all but three were below 100 nM; 39 were below 50 nM; 34 compounds were below 25.00 nM; 27 compounds were below 10.00 nM; 21 compounds were below 5.00 nM; and 10 compounds were below 1.00 nM. The five analogues had an IC$_{50}$ (low albumin) in the range of 2-15 nM.

Finally as regards IC$_{50}$ (high albumin), all compounds had an IC$_{50}$ (high albumin) at 1000.00 nM or below; 41 compounds were below 1000.00 nM; 29 compounds were below 500.00 nM; 13 compounds were below 100.00 nM; and 10 compounds were below 50.00 nM. The five analogues had an an IC$_{50}$ (high albumin) in the range of 0.35-2.97 nM.

All compounds, analogues as well as derivatives, bind well to the GLP-1 receptor in the presence of low albumin. Furthermore, as expected, it is mainly the binding of the derivatives to the receptor, that is influenced by the increased albumin concentration.

Example 50

Stability Against Degradation by Intestinal Enzymes

The purpose of this Example is to test the stability of the compounds of the invention against degradation by intestinal enzymes.

GLP-1(7-37) was used in the assay as a kind of a standard, and liraglutide and semaglutide were included for comparison.

The compounds tested were the analogues and derivatives of Examples 1-23, 27-30, 32-35, 38-39, and 41-47.

The strongest proteolytic activities in the intestine are of pancreatic origin and include the serine endopeptidases trypsin, chymotrypsin, and elastase as well as several types of carboxypeptidases.

An assay with small intestine extract from rats was developed and used as described in the following.

Extracts from Rat Small Intestine

Small intestines were prepared from rats and flushed with 8 ml of 150 mM NaCl, 20 mM Hepes pH 7.4. The solutions were centrifuged for 15 min at 4,600 rpm in a Heraeus Multifuge 3 S-R centrifuge with a 75006445 rotor. The supernatants were removed and filtered through a 0.22 μm Millipore Millex GV PVDF membrane. Filtrates of several animals were pooled to average out individual differences.

The protein content of the obtained extracts was determined by Bradford Assay (see e.g. Analytical Biochemistry (1976), vol. 72, p. 248-254, and Analytical Biochemistry (1996), vol. 236 p. 302-308).

Degradation Assay 2.5 nmol of the compounds to be tested were incubated with the intestinal extract in a volume of 250 μl at 37° C. over a period of one hour. Intestinal samples were assayed in presence of 20 mM Hepes at pH 7.4. The concentration of the intestinal extract was titrated in pilot experiments so that the half-life (t½) of GLP-1(7-37) was in the range of 10-20 minutes. The small intestine extract was used at a concentration of 1.4 μg/ml. All components except for the intestinal extract were mixed and pre-warmed for ten minutes at 37° C.

Immediately after addition of the intestinal extract a sample of 50 µl was taken and mixed with the same volume of 1% trifluoroacetic acid (TFA). Further samples were taken accordingly after 15, 30, and 60 minutes.

Sample Analysis

UPLC Analysis

10 µl of the samples were analysed by UPLC using a Waters Acquity system with a BEH C18 1.7 µm 2.1×50 mm column and a 30 to 65% gradient of 0.1% TFA and 0.07% TFA in acetonitrile over 5 minutes at a flow rate of 0.6 ml/min. After baseline subtraction the peak integrals of the intact compounds in the HPLC chromatogram recorded at a wavelength of 214 nm were determined.

MALDI-TOF Analysis

1 µl of each sample was transferred to a Bruker/Eppendorf PAC HCCA 384 MALDI target. Analysis was performed with a Bruker Autoflex matrix-assisted laser desorption and ionisation-time of flight (MALDI-TOF) mass spectrometer using the pre-defined method "PAC_measure" with an extended detection range of 500 to 5000 Da and the pre-defined calibration method "PAC_calibrate".

Data Analysis

The peak integrals of the HPLC chromatograms were plotted against time. The half-life of the respective compound was calculated by fitting the data using SigmaPlot 9.0 software and an equation for a 2-parameter exponential decay.

For each compound tested, the relative half-life (relative $T_{1/2}$) was calculated as the half-life ($T_{1/2}$) of the compound in question, divided by the half-life ($T_{1/2}$) of GLP-1(7-37), determined in the same way.

Results

The relative half-life of the known compounds liraglutide and semaglutide was 4.8 and 1.2, respectively.

All thirty-eight tested GLP-1 analogues and derivatives had a relative half-life of at least 1; thirty-six compounds had a relative half-life of at least 2; thirty compounds had a half-life of at least 5, nine compounds had a half-life of at least 10; and three compounds had a half-life of at least 15. Thirty-seven compounds had a relative half-life higher than that of semaglutide. Twenty-five compounds had a relative half-life higher than that of liraglutide. The relative half-life of the three analogues that were tested was in the range of 3-6.

Example 51

Pharmacokinetics in Rat

The purpose of this Example is to investigate half-life in vivo in rat of the derivatives of the invention.

In vivo pharmacokinetic studies in rats were performed with the derivatives of Examples 2, 7, 14, 16-17, 20, 30, and 38, as described in the following. Semaglutide was included for comparison.

Male Sprague Dawley rats of same age with a body weight from 400 to 600 g were obtained from Taconic (Denmark) and assigned to the treatments by simple randomisation on body weight, approximately 3-6 rats per group, so that all animals in each group were of similar body weight.

The GLP-1 derivatives (approximately 6 nmole/ml) were dissolved in 50 mM sodium phosphate, 145 mM sodium chloride, 0.05% TWEEN™ polysorbate-80, pH 7.4. Intravenous injections (1.0 ml/kg) of the compounds were given through a catheter implanted in the right jugular vein. Blood was sampled from vena sublingualis for 5 days post dosing. Blood samples (200 µl) were collected in EDTA buffer (8 mM) and then centrifuged at 4° C. and 10000G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoasssay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemi-luminescence which was measured in an Envision plate reader. The amount of light was proportional to the concentration of the compound.

Plasma concentration-time profiles were analyzed using WinNonlin (ver. 5.0, Pharsight Inc., Mountain View, Calif., USA), and the half-life ($T_{1/2}$) calculated using individual plasma concentration-time profiles from each animal (harmonic mean).

Results

The half-life of semaglutide was 4 hours.

All eight derivatives tested had a half-life of at least 5 hours, and seven had a half-life of at least 10 hours.

Example 52

Pharmacokinetics in Minipigs

The purpose of this study is to determine the protraction in vivo of the GLP-1 derivatives of the invention after i.v. administration to minipigs, i.e. the prolongation of their time of action.

This is done in a pharmacokinetic (PK) study, where the terminal half-life of the derivative in question is determined. By terminal half-life is generally meant the period of time it takes to halve a certain plasma concentration, measured after the initial distribution phase. Male Göttingen minipigs obtained from Ellegaard Göttingen Minipigs (Dalmose, Denmark) approximately 7-14 months of age and weighing from approximately 16-35 kg were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between dosings.

The animals were fasted for approximately 18 h before dosing and for at least 4 h after dosing, but had ad libitum access to water during the whole period.

The GLP-1 derivatives of Examples 2, 7, 14-15, and 20 were dissolved in 50 mM sodium phosphate, 145 mM sodium chloride, 0.05% TWEEN™ polysorbate-80, pH 7.4 to a concentration of usually from 20-60 nmol/ml. Intravenous injections (the volume corresponding to usually 1-2 nmol/kg, for example 0.033 ml/kg) of the compounds were given through a catheter, and blood was sampled at predefined time points for up till 13 days post dosing (preferably through the other catheter). Blood samples (for example 0.8 ml) were collected in EDTA buffer (8 mM) and then centrifuged at 4° C. and 1942G for 10 minutes. Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in WinNonlin v. 5.0 (Pharsight Inc., Mountain View, Calif., USA), and the resulting terminal half-lives (harmonic mean) determined.

Results

All derivatives tested had a half-life of at least 12 hours, five had a half-life of at least 24 hours, four had a half-life of at least 36 hours, and three had a half-life of at least 48 hours.

Example 53

Estimate of Oral Bioavailability

The purpose of this experiment is to estimate the oral bioavailability of the GLP-1 derivatives of the invention.

To this end, the exposure in plasma after direct injection into the intestinal lumen of the GLP-1 derivatives of Examples 2, 14-17, 20, 28-30, 38, and 41-47 was studied in vivo in rats, as described in the following.

The GLP-1 derivatives were tested in a concentration of 1000 uM in a solution of 55 mg/ml sodium caprate.

32 male Sprague Dawley rats with a body weight upon arrival of approximately 240 g were obtained from Taconic (Denmark) and assigned to the different treatments by simple randomisation, 4 rats per group. The rats were fasted for approximately 18 hours before the experiment and taken into general anaesthesia (Hypnorm/Dormicum).

The GLP-1 derivatives were administered in the jejunum either in the proximal part (10 cm distal for the duodenum) or in the mid-intestine (50 cm proximal for the cecum). A PE50-catheter, 10 cm long was inserted into the jejunum, forwarded at least 1.5 cm into the jejunum, and secured before dosing by ligature around the gut and the catheter with 3/0 suture distal to tip to prevent leak or catheter displacement. Catheter was placed without syringe and needle and 2 ml saline was administered into abdomen before closing the incision with wound clips.

100 µl of the respective GLP-1 derivative was injected into the jejunal lumen through the catheter with a 1 ml syringe. Subsequently, 200 µl of air was pushed into the jejunal lumen with another syringe to "flush" the catheter. This syringe was leaved connected to the catheter to prevent flow back into the catheter.

Blood samples (200 ul) were collected at desired intervals (usually at times 0, 10, 30, 60, 120 and 240 min) into EDTA tubes from the tail vein and centrifuged 5 minutes, 10000G, at 4° C. within 20 minutes. Plasma (75 ul) was separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

After the blood sampling the rats were sacrificed under anaesthesia and the abdomen was opened to verify correct catheter placement.

The mean (n=4) plasma concentrations (pmol/l) were determined as a function of time. The ratio of plasma concentration (pmol/l) divided by the concentration of the dosing solution (µmol/l) was calculated for each treatment, and the results for t=30 min (30 minutes after the injection of the compound in the jejunum) were assessed (dose-corrected exposure at 30 min) as a surrogate measure of intestinal bioavailability. The dose-corrected exposure has been shown to correlate significantly with the actual bioavailability.

The following results were obtained, where dose-corrected exposure at 30 min refers to (the plasma concentration 30 minutes after injection of the compound in the jejunum (pM)), divided by (the concentration of the compound in the dosing solution (µM)):

Results:

All but three of the tested derivatives had a dose-corrected exposure at 30 min of above 48; eight were above 100; three were above 125; and one was above 150.

For comparison, the compounds of Examples 69 and 71 of WO09030771 had a dose-corrected exposure at 30 min of 48, and 20, respectively.

Example 54

Effect on Blood Glucose and Body Weight

The purpose of the study is to verify the effect of the GLP-1 compounds of the invention on blood glucose (BG) and body weight (BW) in a diabetic setting.

The GLP-1 derivatives of Examples 2, 4, 7, 14 and 15 were tested in a dose-response study in an obese, diabetic mouse model (db/db mice) as described in the following.

Fifty db/db mice (Taconic, Denmark), fed from birth with the diet NIH31 (NIH 31M Rodent Diet, commercially available from Taconic Farms, Inc., US, see www.taconic.com), were enrolled for the study at the age of 7-9 weeks The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The 8 mice with the lowest blood glucose values were excluded from the experiments. Based on the mean blood glucose values, the remaining 42 mice were selected for further experimentation and allocated to 7 groups (n=6) with matching blood glucose levels. The mice were used in experiments with duration of 5 days for up to 4 times. After the last experiment the mice were euthanised.

The seven groups received treatment as follows:
1: Vehicle, s.c.
2: GLP-1 derivative, 0.3 nmol/kg, s.c.
3: GLP-1 derivative, 1.0 nmol/kg, s.c.
4: GLP-1 derivative, 3.0 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.
Vehicle: 50 mM sodium phosphate, 145 mM sodium chloride, 0.05% TWEEN™ polysorbate-80, pH 7.4.

The GLP-1 derivative was dissolved in the vehicle, to concentrations of 0.05, 0.17, 0.5, 1.7, 5.0 and 17.0 nmol/ml. Animals were dosed s.c. with a dose-volume of 6 ml/kg (i.e. 300 µl per 50 g mouse).

On the day of dosing, blood glucose was assessed at time −½h (8.30 am), where after the mice were weighed. The GLP-1 derivative was dosed at approximately 9 am (time 0).

On the day of dosing, blood glucose was assessed at times 1, 2, 4 and 8 h (10 am, 11 am, 1 pm and 5 pm).

On the following days, the blood glucose was assessed at time 24, 48, 72, and 96 h after dosing (i.e. at 9 am on day 2, 3, 4, 5). On each day, the mice were weighed following blood glucose sampling.

The mice were weighed individually on a digital weight.

Samples for the measurement of blood glucose were obtained from the tail tip capillary of conscious mice. Blood, 10 µl, was collected into heparinised capillaries and transferred to 500 µl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

$ED_{50}$ is the dose giving rise to half-maximal effect in nmol/kg. This value is calculated on the basis of the ability of the derivatives to lower body weight as well as the ability to lower blood glucose, as explained below.

$ED_{50}$ for body weight is calculated as the dose giving rise to half-maximum effect on delta BW 24 hours following the subcutaneous administration of the derivative. For example, if the maximum decrease in body weight after 24 hours is 4.0 g, then $ED_{50}$ bodyweight would be that dose in nmol/kg which gives rise to a decrease in body weight after 24 hours of 2.0 g. This dose ($ED_{50}$ body weight) may be read from the dose-response curve.

$ED_{50}$ for blood glucose is calcualated as the dose giving rise to half-maximum effect on AUC delta BG 8 hours following the subcutaneous administration of the analogue.

The $ED_{50}$ value may only be calculated if a proper sigmoidal dose-response relationship exists with a clear definition of the maximum response. Thus, if this would not be the case the derivative in question is re-tested in a different range of doses until the sigmoidal dose-response relationship is obtained.

The following results were obtained:

The tested derivatives had the expected effect on blood glucose as well as on body weight (a lowering in both cases). Furthermore, a sigmoidal dose-response curve was obtained enabling the calculation of the $ED_{50}$ values for blood glucose and body weight, respectively, as explained above.

Example 55

Effect on Glucose Mediated Insulin Secretion

The purpose of this example is to test the effect of GLP-1 compounds of the invention on glucose mediated insulin secretion.

This is done in Göttingen minipigs using intravenous glucose tolerance test (IVGTT).

Male Göttingen minipigs (Ellegaard Göttingen minipigs A/S, Dalmose, Denmark), 7-14 months of age are used in the studies. The animals are housed in single pens during acclimatisation and during experiments. After at least 2 weeks of acclimatisation two permanent central venous catheters are implanted in vena cava caudalis or cranialis in each animal. The animals are allowed 1 week recovery after the surgery, and are then used for repeated studies with a suitable washout period between dosings.

The pigs are fed restrictedly 1-2 times a day with SDS minipig fodder (Special Diets Services, Essex, UK) and are allowed ad libitum access to water.

The effect of the GLP-1 compounds is tested after a single dose or after a period with dose escalation to avoid adverse effects from acute high doses. The GLP-1 derivatives are given either i.v. or s.c. in the thin skin behind the ear.

For each tested GLP-1 compound there is a vehicle treated (or untreated) baseline group and 2-6 GLP-1 dose groups corresponding to 2-6 different plasma concentration levels, which are usually from around 3000-80000 pM (n=5-8).

For each GLP-1 compound a 1 or 2 hour intravenous glucose tolerance test is performed. The pigs are fasted for approximately 18 h before the experiment. Patency of the central venous catheters is checked, and two baseline blood samples are taken. After the sample at 0 minutes 0.3 g/kg glucose (Glucose 500 g/L, SAD) is given i.v. over a period of 30 seconds and the catheter is flushed with 10-20 ml of sterile 0.9% NaCl. Blood samples are usually taken at the following time points in relation to the glucose bolus: −10, −5, 0, 2, 5, 10, 15, 20, 25, 30, 40, 50, 60, 70, 80, 90, 100, 110, 120 minutes, and after each blood sample the catheter is flushed with 4 ml of sterile 0.9% NaCl with 10 U/ml Heparin. Blood samples for insulin, glucose and plasma concentrations of the derivatives are transferred to tubes coated with EDTA. The tubes are stored on wet ice until centrifugation within 1 hour (4° C., 3000 rpm, 10 min), plasma is pipetted into Micronic tubes on dry ice and stored at −20° C. until analysis. Depending of the half life of the GLP-1 derivative plasma concentrations are measured at t=0 min, or at t=0 min and at the end of the test (t=60 min or t=120 min). Glucose is analyzed using the glucose oxidase method according to the manufacturer's instructions with 10 µL plasma in 500 µL buffer (EBIO plus autoanalyzer and solution, Eppendorf, Germany). Insulin is analyzed using a suitable immunometric assay (such as LOCI, see e.g. Journal of Biomolecular Screening 2007, vol. 12, p. 240-247). The plasma concentration of GLP-1 derivative is analyzed using ELISA or a similar antibody based assay or LC-MS.

For each study the area under the insulin curve (AUCinsulin) is calculated and used as a measure of insulin secretion. The different dose groups are compared to the respective vehicle/baseline group using one-way ANOVA or other appropriate statistical analysis. An EC50 for AUCinsulin may also be calculated.

Example 56

Effect on Feed Intake

The purpose of this experiment is to investigate the effect of GLP-1 compounds of the invention on feed intake in pigs. This is done in a pharmacodynamic (PD) study as described below, in which feed intake is measured 1, 2, 3, and 4 days after administration of a single dose of the GLP-1 derivative, as compared to a vehicle-treated control group.

Female Landrace Yorkshire Duroc (LYD) pigs, approximately 3 months of age, weighing approximately 30-35 kg are used (n=3-4 per group). The animals are housed in a group for 1-2 weeks during acclimatisation to the animal facilities. During the experimental period the animals are placed in individual pens from Monday morning to Friday afternoon for measurement of individual food intake. The animals are fed ad libitum with pig fodder (Svinefoder, Antonio) at all times both during the acclimatisation and the experimental period. Food intake is monitored on line by logging the weight of fodder every 15 minutes. The system used is Mpigwin (Ellegaard Systems, Faaborg, Denmark).

The GLP-1 derivatives are dissolved in a phosphate buffer (50 mM phosphate, 0.05% TWEEN™ polysorbate-80, pH 8) at concentrations of 12, 40, 120, 400 or 1200 nmol/ml corresponding to doses of 0.3, 1, 3, 10 or 30 nmol/kg. The phosphate buffer served as vehicle. Animals are dosed with a single subcutaneous dose of the GLP-1 derivative or vehicle (dose volume 0.025 ml/kg) on the morning of day 1, and feed intake is measured for 4 days after dosing. On the last day of each study, 4 days after dosing, a blood sample for measurement of plasma exposure of the GLP-1 derivative is taken from the heart in anaesthetised animals. The animals are thereafter euthanised with an intra-cardial overdose of pentobarbitone. Plasma content of the GLP-1 derivatives is analysed using ELISA or a similar antibody based assay.

Feed intake is calculated as mean±SEM 24 h food intake on the 4 days.

Statistical comparisons of the 24 hour feed intake in the vehicle vs. GLP-1 derivative group on the 4 days are done using one-way or two-way-ANOVA repeated measures, followed by Bonferroni post-test.

Example 57

Albumin Binding Affinity

The purpose of this Example is to measure the affinity of GLP-1 derivatives of the invention to human serum albumin (HSA).

The dissociation constant ($K_d$) is commonly used to describe the affinity between a drug and a protein, i.e. how tightly the drug binds to the protein.

The dissociation constants of the derivatives of Examples 2, 4-9, 11-18, 20-21, 23-25, and 27-46 to HSA were determined by a competition scintillation proximity assay (SPA) as described in the following.

Streptavidin-SPA beads (GE Healthcare RPNQ0009) were incubated with biotinylated HSA for 5 hours. The beads were washed with buffer to remove unbound HSA. The beads were mixed with a tracer, viz. $^{125}$I-labeled acylated GLP-1 analogue (N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino)ethoxy]ethoxy)acetyl][Aib8, $^{125}$I-Tyr19,Glu22,Arg26,Arg34,Lys37] GLP-1(7-37)-NH$_2$) in a buffer containing 100 mM Hepes, 100 mM NaCl, 10 mM MgSO$_4$, 0.025% TWEEN™ polysorbate-20, pH 7.4. The mixture was pipetted into the wells of a Perkin Elmer Optiplate-96 6005290 (100 μl per well) and 100 μl of a dilution series of the GLP-1 derivative to be measured was added in the same buffer. After 20 hours of gentle rocking at room temperature the plates were centrifuged and counted on a TopCounter. Bound cpm was plotted as a function of GLP-1 derivative concentration.

This assay is based on the assumption that the tested derivatives bind to the same binding site(s) as the tracer.

The $K_d$ may be calculated as the molar concentration of the GLP-1 derivative in question, multiplied by the molar concentration of HSA, and divided by the molar concentration of GLP-1-HSA complex. Thus, the dissociation constant has molar units (M), which correspond to the concentration of the GLP-1 derivative at which the binding site on HSA is half occupied, i.e. the concentration of the GLP-1 derivative, at which the concentration of the HSA-GLP-1 complex equals the concentration of HSA with no GLP-1 derivative bound. The smaller the dissociation constant, the more tightly bound the GLP-1 derivative is, or the higher the affinity between the GLP-1 derivative and HSA.

Alternatively, the $EC_K$ value of the competition curve may be used as a measure of the affinity of the derivative for HSA (herein "$K_d$ apparent").

Results:

All but five of the tested derivatives had a relatively low binding affinity to albumin, corresponding to a relatively high apparent dissociation constant ($K_d$ apparent, in μM) at or above 1. Twenty-three were at 5 or above. Eighteen were above 10, and twelve were above 20.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

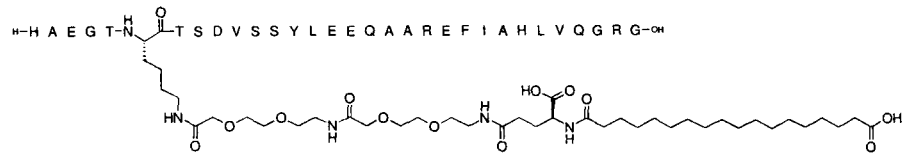

The invention claimed is:

1. A GLP-1 analogue which comprises a histidine residue at a position corresponding to position 31 of GLP-1(7-37) (SEQ ID NO: 1), a glutamine residue at a position corresponding to position 34 of GLP-1(7-37) (SEQ ID NO: 1), and a maximum of ten additional amino acid modifications as compared to GLP-1(7-37) (SEQ ID NO: 1); wherein the histidine residue is designated $H^{31}$, and the glutamine residue is designated $Q^{34}$; or a pharmaceutically acceptable salt, amide, or ester thereof.

2. A derivative of an analogue of claim 1, or a pharmaceutically acceptable salt, amide, or ester thereof.

3. The derivative of claim 2, which has an albumin binding moiety attached to a lysine residue of the analogue.

4. The derivative of claim 3, in which the albumin binding moiety comprises a protracting moiety selected from Chem. 1, Chem. 2, Chem. 3, and Chem. 4:

$CH_3—(CH_2)_x—CO—*$  Chem. 1:

$HOOC—(CH_2)_x—CO—*$  Chem. 2:

$HN_4C—(CH_2)_x—CO—*$  Chem. 3:

$HOOC—C_6H_4—O—(CH_2)_y—CO—*$,  Chem. 4:

in which x is an integer in the range of 6-18, and y is an integer in the range of 3-17.

5. The derivative of claim 4, wherein the albumin binding moiety further comprises a linker selected from Chem. 5, Chem. 6, Chem. 7, Chem. 8, Chem. 9, and Chem. 10:

$*—NH—CH_2—CH_2—(O—CH_2—CH_2)_k—O—(CH_2)_n—CO—*$  Chem. 5:

$*—NH—C(COOH)—(CH_2)_2—CO—*$  Chem. 6:

$*—N—C((CH_2)_2COOH)—CO—*$  Chem. 7:

$*—NH—C_6H_8—CO—*$  Chem. 8:

$*—NC_5H_8—CO—*$  Chem. 9:

$*—NH—SO_2—(CH_2)_3—CO—*$  Chem. 10:

wherein k is an integer in the range of 1-5, and n is an integer in the range of 1-5.

6. A GLP-1 compound selected from the following compounds:

[$Aib^8$,$His^{31}$,$Gln^{34}$]GLP-1(7-37)-peptide (SEQ ID NO: 4)

Chem. 20

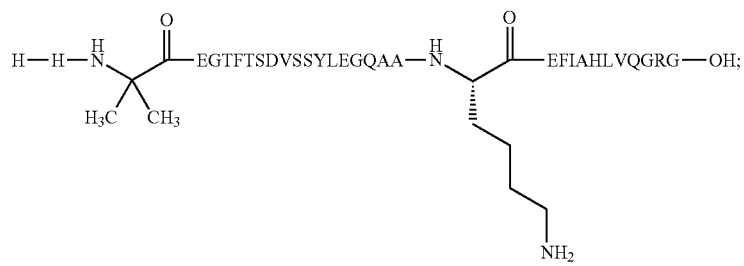

N$^{\epsilon 26}$-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Aib$^8$,His$^{31}$,Gln$^{34}$] GLP-1(7-37)-peptide (SEQ ID NO: 4)

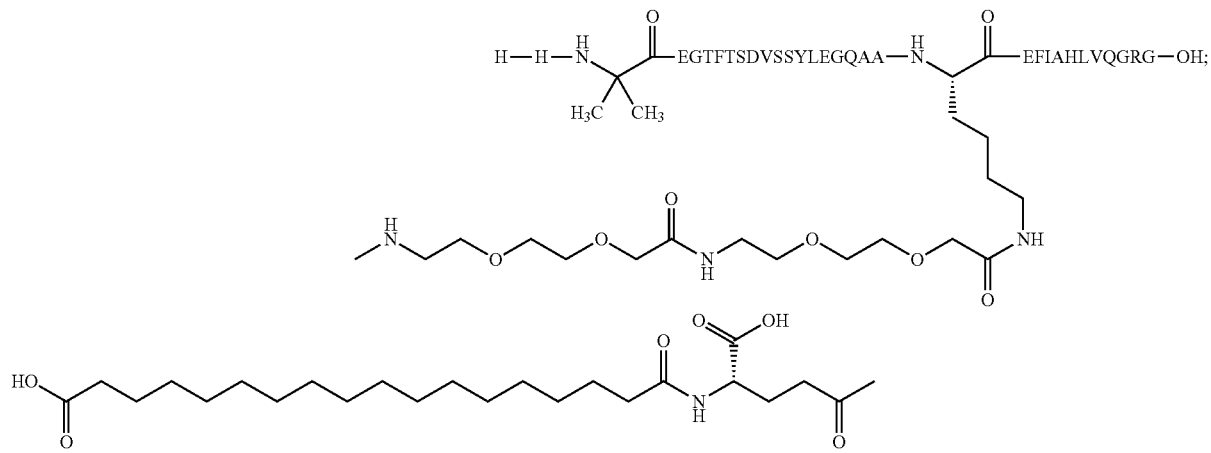

Chem. 21

[Aib$^8$,Glu$^{30}$,His$^{31}$,Gln$^{34}$,Lys$^{36}$] GLP-1(7-37)yl-Glu$^{38}$-peptide amide(SEQ ID NO: 2) Chem. 22:

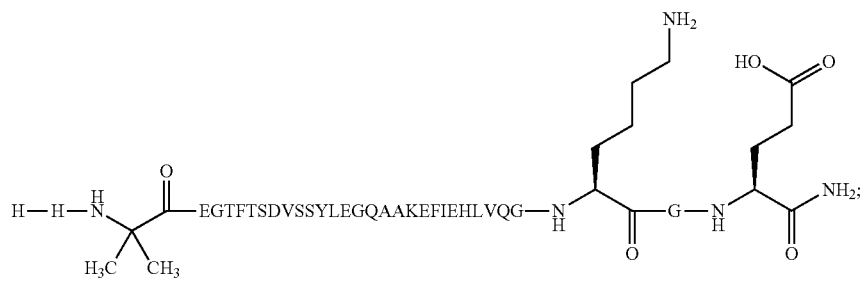

Chem. 22

N$^{\epsilon 2}$(2-{2-[2-(2-{2-[2-(17-Carboxy-heptadecanoylamino)ethoxy]ethoxy}acetylamino)ethoxy]ethoxy}acetyl) [Aib$^8$,Lys$^{12}$, Glu$^{22}$,Arg$^{26}$,His$^{31}$,Gln$^{34}$]GLP-1(7-37)-peptide (SEQ ID NO: 5)

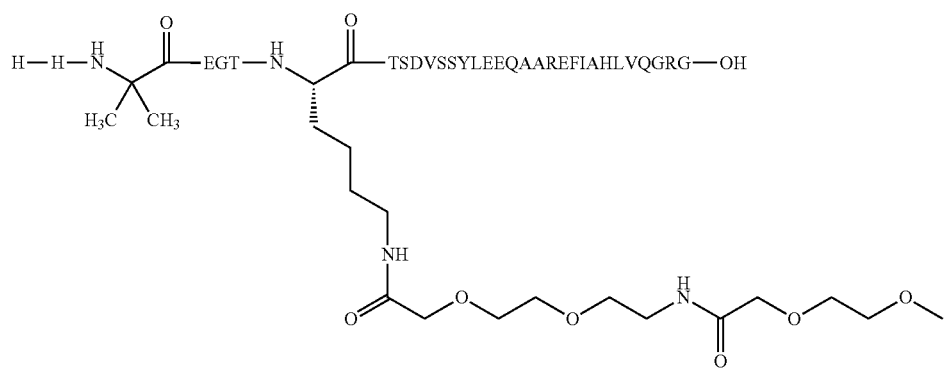

Chem. 23

-continued

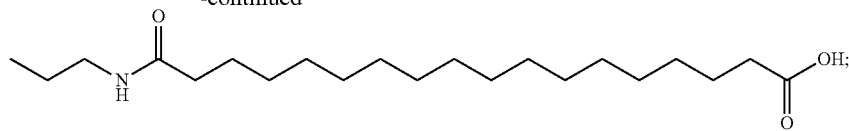

N$^{\epsilon 12}$-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Aib$^8$,Lys$^{12}$, His$^{31}$, Gln$^{34}$]GLP-1(7-37)-peptide (SEQ ID NO: 7)

Chem. 24

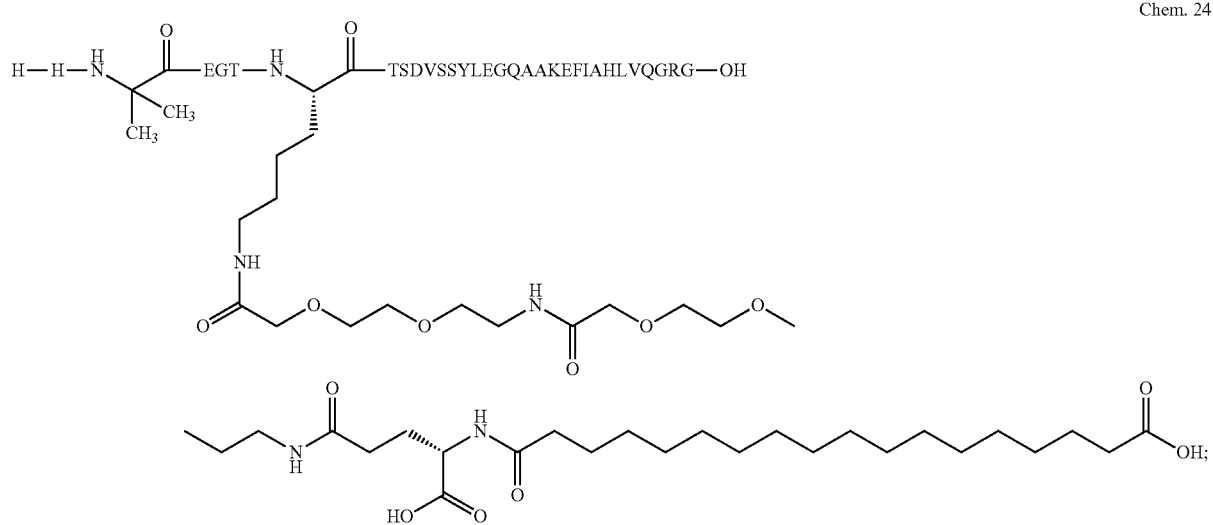

N$^{\epsilon 2}$-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Aib$^8$,Lys$^{12}$, Glu$^{22}$, Arg$^{26}$,His$^{31}$,Gln$^{34}$]GLP-1(7-37)-peptide (SEQ ID NO: 5)

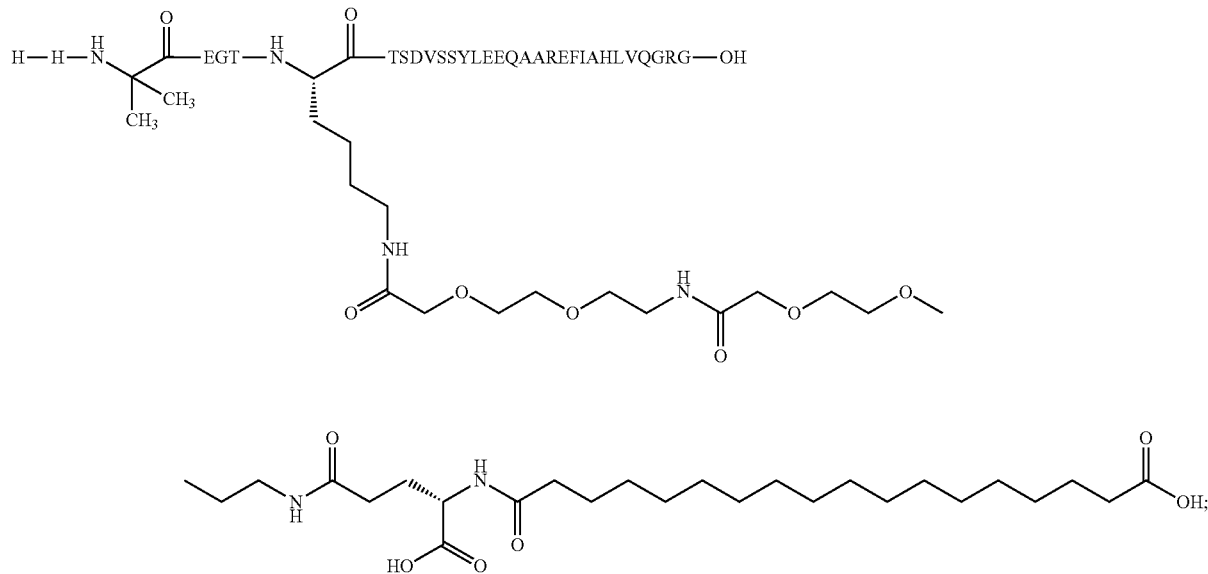

N^{ε26}-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][His^{31},Gln^{34}]GLP-1-(7-37)-peptide (SEQ ID NO: 9)
Chem. 26
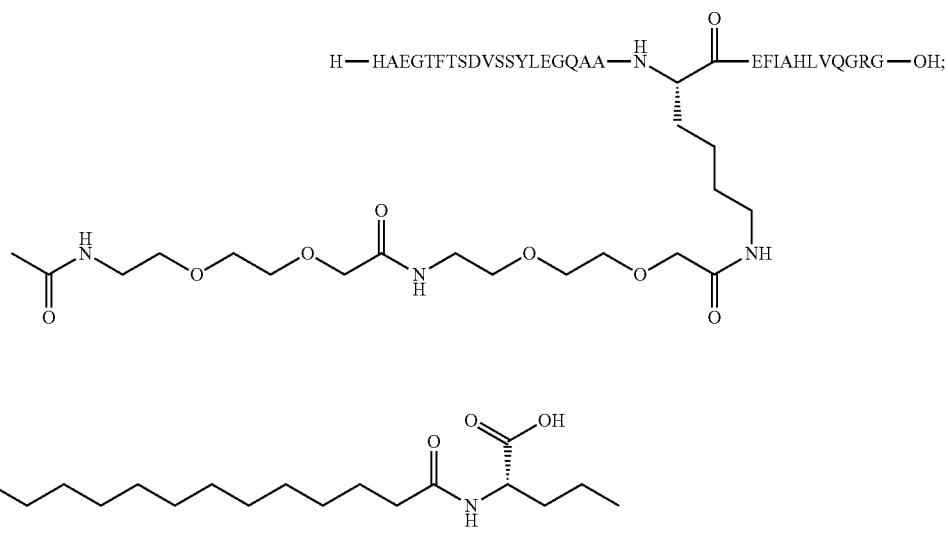
N^{ε18}[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Aib^8,Lys^{18},Glu^{22},Arg^{26},His^{31},Gln^{34}] GLP-1(7-37)-peptide (SEQ ID NO: 10)
35
Chem. 27
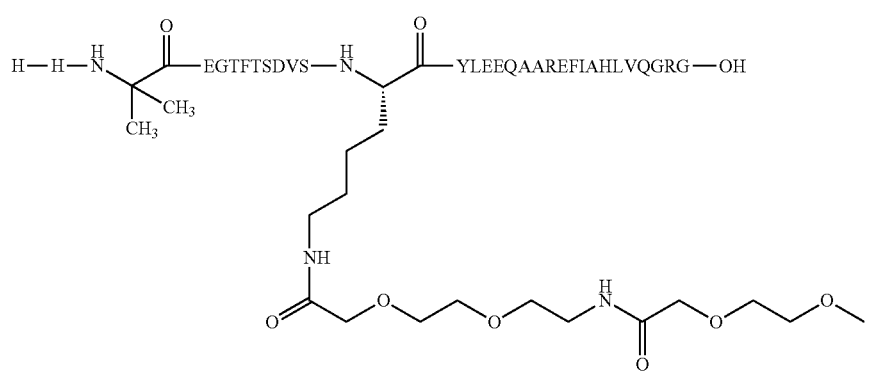
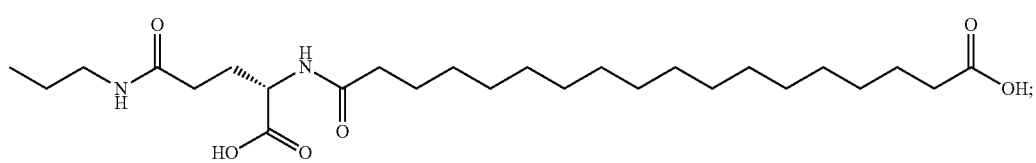

N^{ε26}[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Gly^8,His^{31},Gln^{34}] GLP-1(7-37)-peptide (SEQ ID NO: 12)

Chem. 28

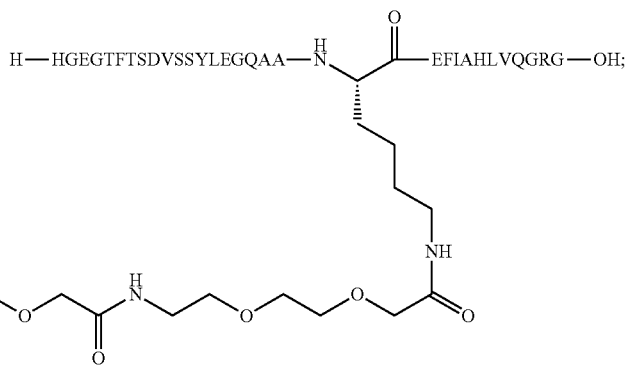

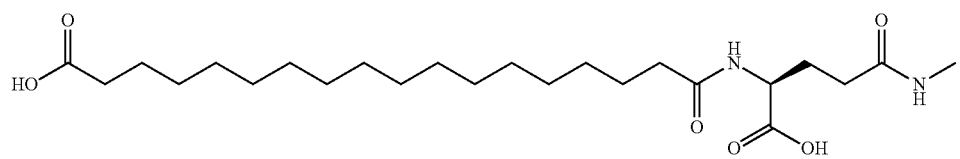

N^{ε26} [(S)-4-Carboxy-4-(2-{2-[2-(2-{2-[2-(17-carboxy-heptadecanoylamino)ethoxy]ethoxy}acetylamino)ethoxy]-ethoxy}acetylamino)butyryl] [Aib^8,His^{31}, Gln^{34}]GLP-1(7-37)-peptide (SEQ ID NO: 4)

Chem. 29

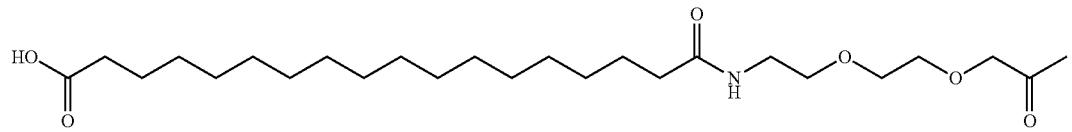

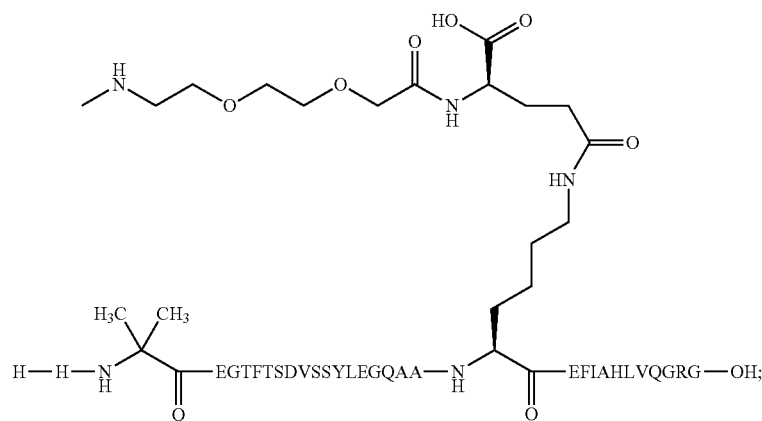

N^{ε26}-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][D-Ala^8,His^{31}, Gln^{34}]GLP-1(7-37)-peptide (SEQ ID NO: 15)

Chem. 30
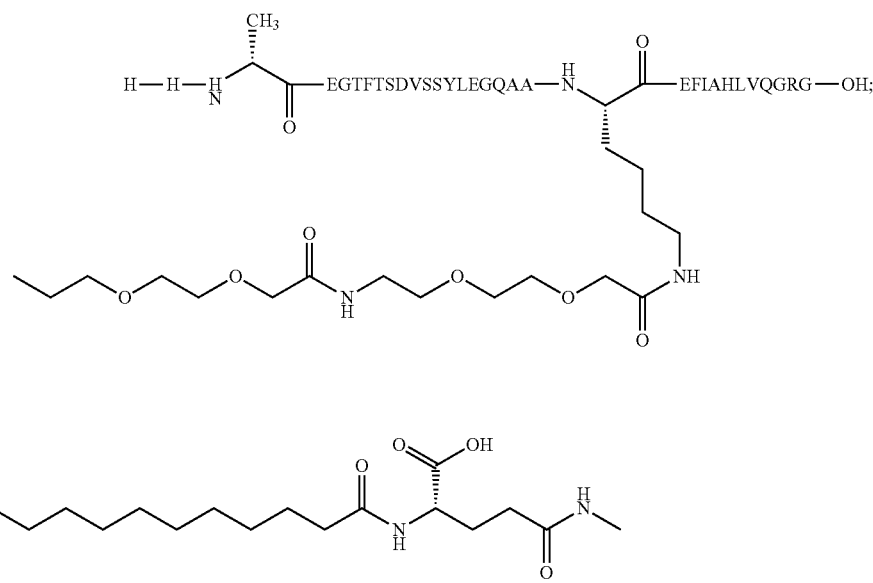
N^8 3H-Imidazol-4-yl-acetyl, N^{ε26}-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His^{31},Gln^{34}]GLP-1(8-37)-peptide (SEQ ID NO: 9)
Chem. 31
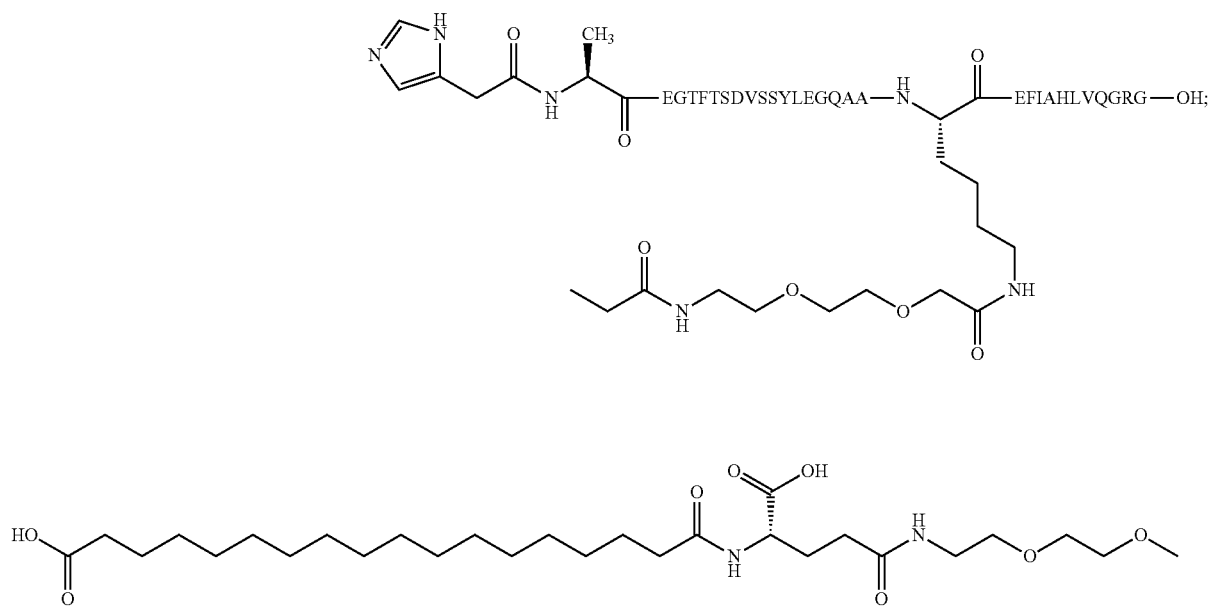
N^{ε26}[2-(2-{2-[2-(2-{2-[(S) 4-Carboxy-4-(17-carboxyheptadecanoylamino)butyrylamino]ethoxy}ethoxy)acetylamino]ethoxy}ethoxy)acetyl] [Ser^8,His^{31},Gln^{34}] GLP-1(7-37)-peptide (SEQ ID NO: 16)

Chem. 32
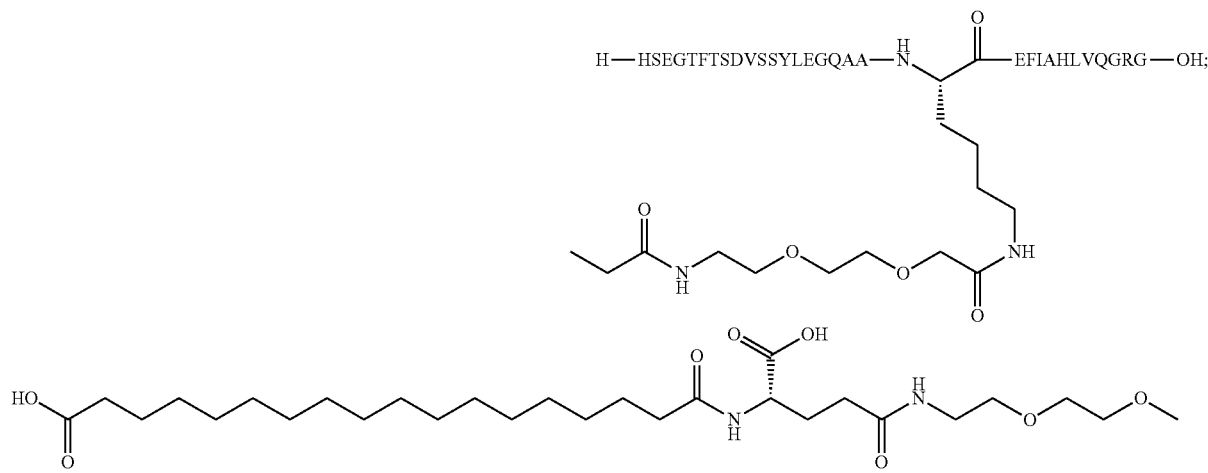
N$^{\varepsilon 26}$-[2-(2-{2-[2-(2-{2-[(S)-4-Carboxy-4-(15-carboxy-pentadecanoylamino)butyrylamino]ethoxy}ethoxy)acetylamino]ethoxy}ethoxy)acetyl][Aib$^8$,His$^{31}$,Gln$^{34}$] GLP-1(7-37)-peptide (SEQ ID NO: 4)
Chem. 33
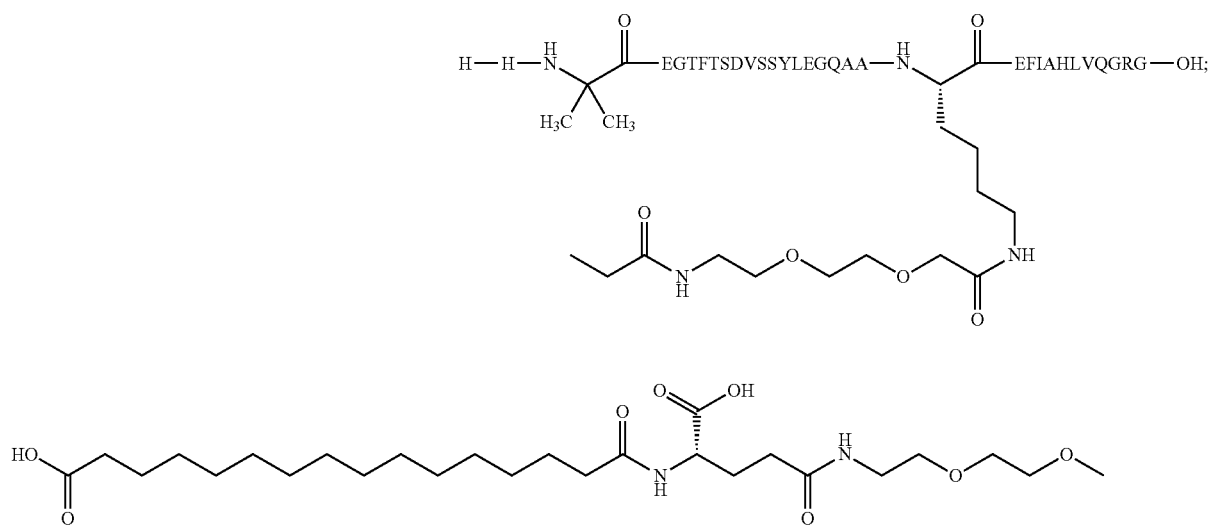
N$^{\varepsilon 27}$-{2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl}-(Aib$^8$,Arg$^{26}$,Lys$^{27}$,His$^{31}$,Gln$^{34}$) GLP-1(7-37)-peptide (SEQ ID NO: 17)
Chem. 34
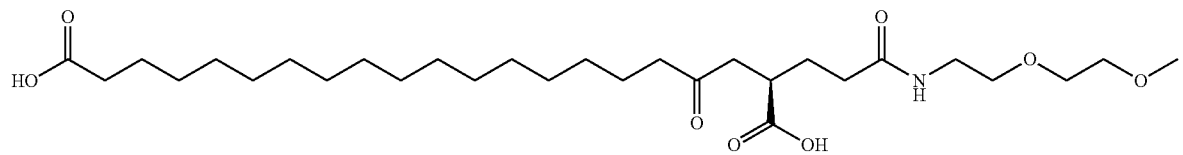

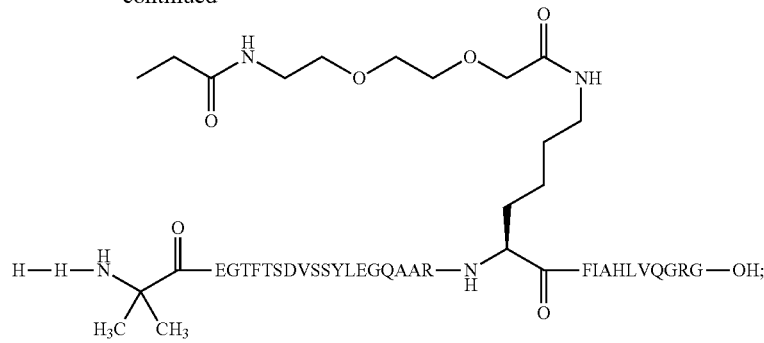

$N^{\epsilon 26}$ [2-(2-(2-{2-[(S)-4-Carboxy-4-(15-carboxypentadecanoylamino)butyrylamino]ethoxy}ethoxy)acetyl][Aib$^8$,His$^{31}$,Gln$^{34}$]GLP-1(7-37)-peptide (SEQ ID NO: 4)

Chem. 35

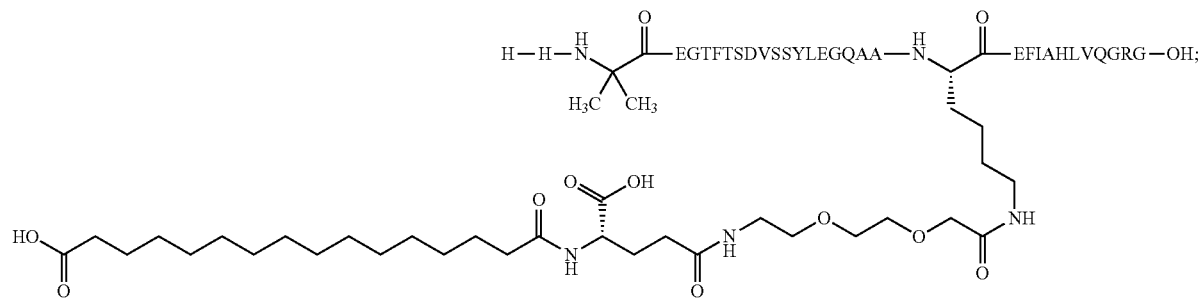

$N^{\epsilon 26}$ [(S)-4-Carboxy-4-(15-carboxypentadecanoylamino)butyryl][Aib$^8$,His$^{31}$,Gln$^{34}$]GLP-1(7-37)-peptide (SEQ ID NO: 4)

Chem. 36

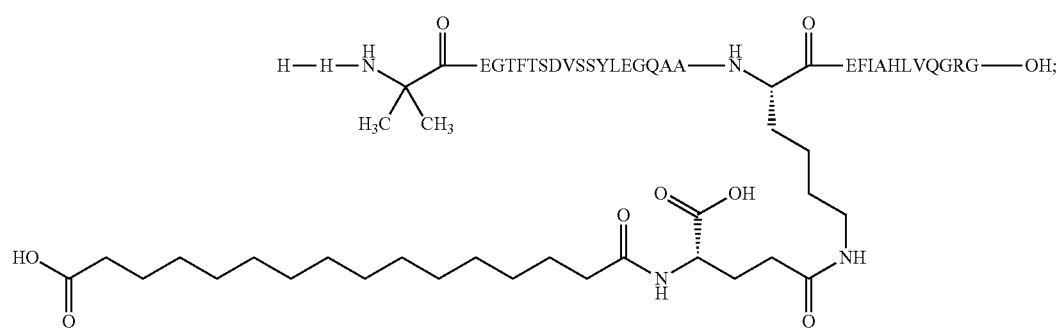

$N^{\alpha 9}$-{2-[2-(1H-Imidazol-4-yl)-ethylcarbamoyl]-2-methyl-propionyl}-$N^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His$^{31}$,Gln$^{34}$]GLP-1 (9-37)-peptide (SEQ ID NO:9)

Chem. 37
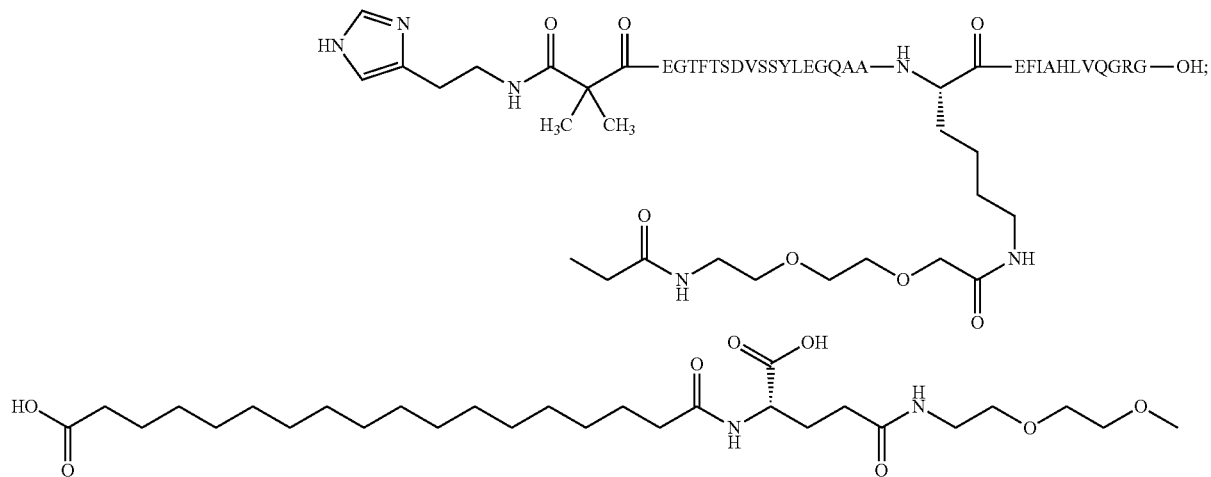
$N^{\epsilon 26}$[2-(2-{2-[(S)-4-Carboxy-4-(2-{2-[2-(17-carboxy-heptadecanoylamino)ethoxy]ethoxy}acetylamino)bu-tyryl amino]ethoxy}ethoxy)acetyl][Aib$^8$,His$^{31}$,Gln$^{34}$] GLP-1(7-37)-peptide (SEQ ID NO: 4)
Chem. 38
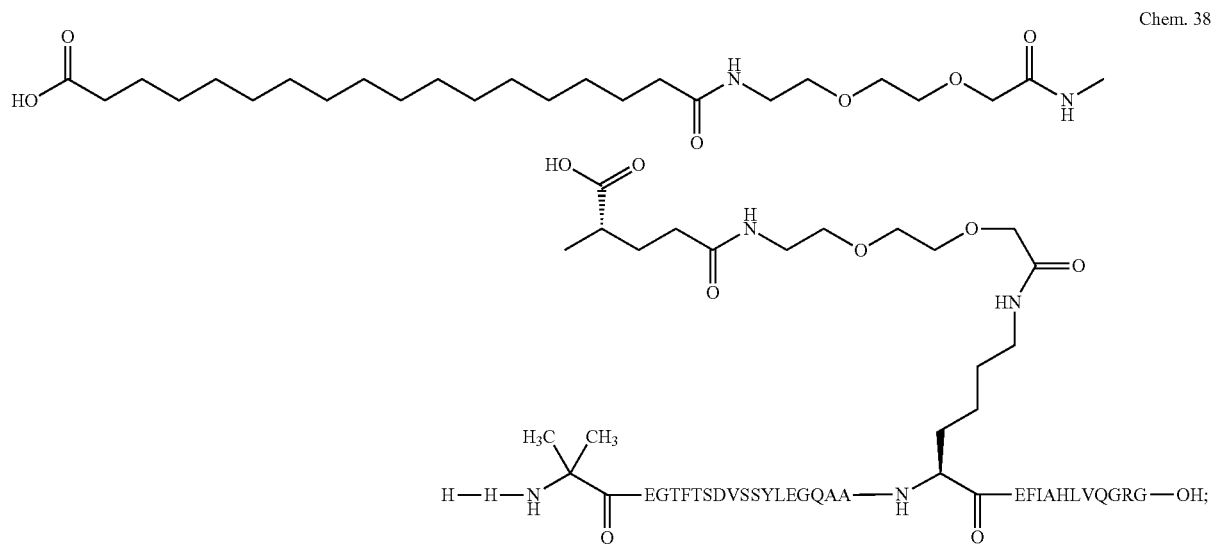
$N^{\epsilon 27}$-{2-(2-{2-[2-(2-{2-[(S)-4-Carboxy-4-(17-carboxy-heptadecanoylamino)butyrylamino]ethoxy}ethoxy) acetylamino]ethoxy}ethoxy)acetyl}-(Aib$^8$,Glu$^{22}$, Arg$^{26}$,Lys$^{27}$,His$^{31}$,Gln$^{34}$) GLP-1(7-37)-peptide (SEQ ID NO: 18)
Chem. 39
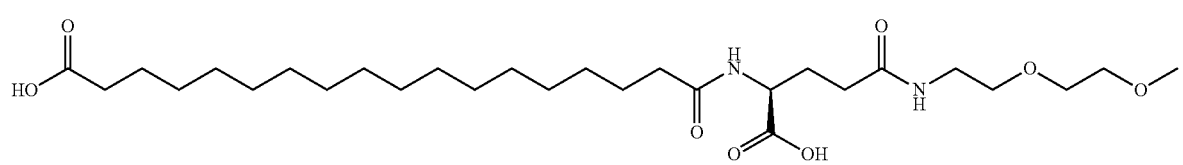

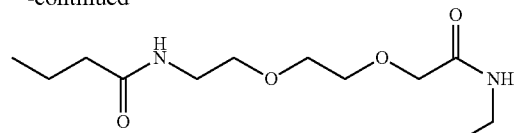
[Imp⁷,Glu²²,Arg²⁶,His³¹,Gln³⁴,Lys³⁷]-GLP-1-(7-37)-peptide (SEQ ID NO: 3)
Chem. 40
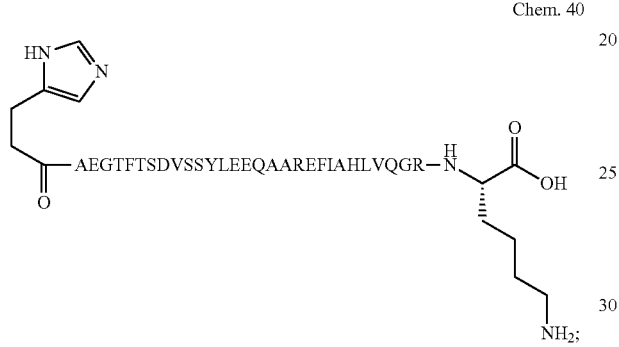
$N^{\epsilon 37}$-[2-[2-[2-[[2-[2-[2-[[(4R)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Imp⁷,Glu²²,Arg²⁶,His³¹,Gln³⁴,Lys³⁷]-GLP-1-(7-37)-peptide (SEQ ID NO: 3)
Chem. 41
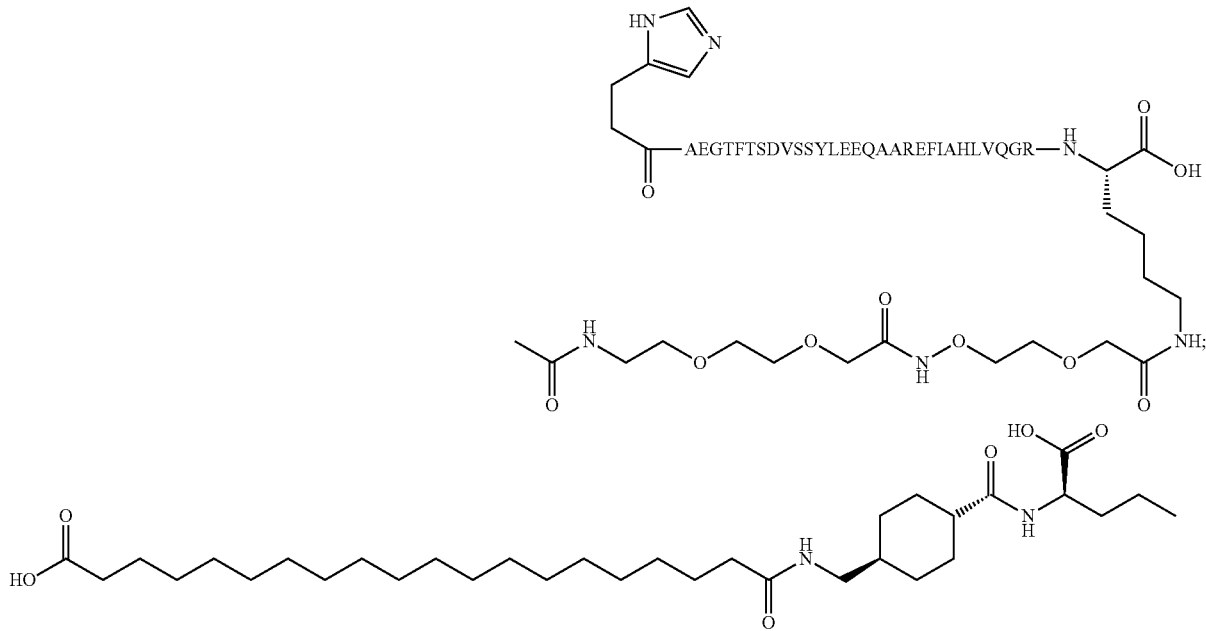

$N^{\epsilon 36}$-[2-[2-[2-(17-carboxyheptadecanoylamino)ethoxy]ethoxy]acetyl]-[Aib$^8$,Glu$^{30}$,His$^{31}$,Gln$^{34}$,Lys$^{36}$]-GLP-1-(7-37)-peptidyl-Glu amide(SEQ ID NO: 2)
Chem. 42
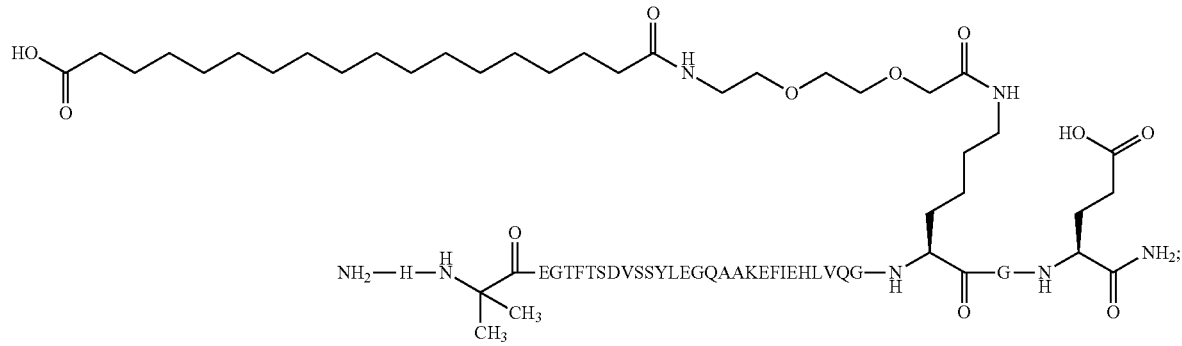
$N^{\alpha}$([Aib$^8$,His$^{31}$,Gln$^{34}$]-GLP-1-(7-37)-peptidyl)-Lysine (SEQ ID NO: 6)
Chem. 43
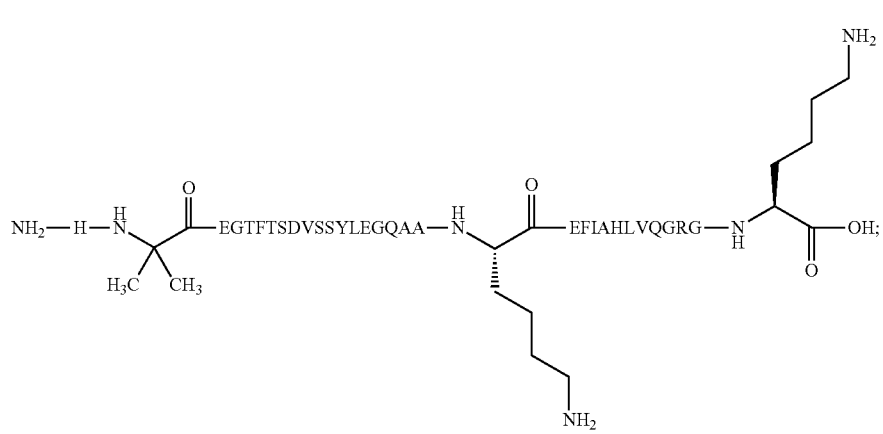
[Aib$^8$,His$^{31}$,Gln$^{34}$,Lys$^{37}$]-GLP-1-(7-37)-peptide (SEQ ID NO: 8)
Chem. 44
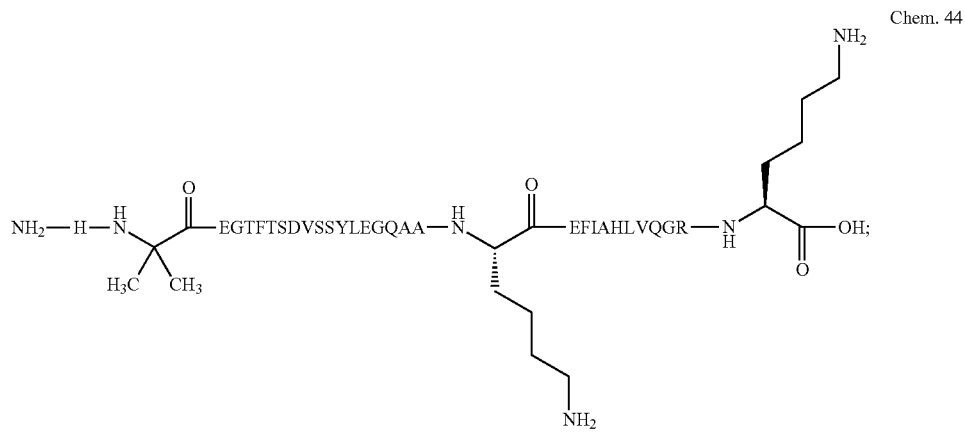

$N^{\epsilon26}$-[(4S)-4-carboxy-4-(tetradecanoylamino)butanoyl], $N^{\epsilon37}$-[(4S)-4-carboxy-4-(tetradecanoylamino)butanoyl]-[Aib$^8$,His$^{31}$,Gln$^{34}$,Lys$^{37}$]-GLP-1-(7-37)-peptide (SEQ ID NO: 8)

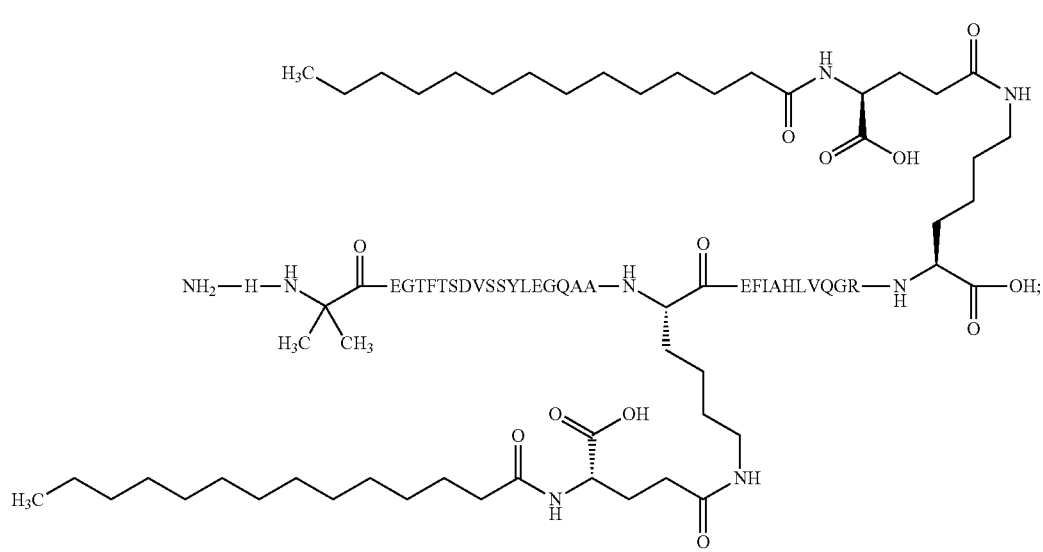

Chem. 45

$N^{\epsilon12}$-12-[2-[2-[2-[[2-[2-[2-(17-carboxyheptadecanoylamino)ethoxy]ethoxy]acetyl]amino]ethoxy]ethoxy]acetyl]-[Lys$^{12}$,Glu$^{22}$,Arg$^{26}$,His$^{31}$,Gln$^{34}$]-GLP-1-(7-37)-peptide (SEQ ID NO: 11)

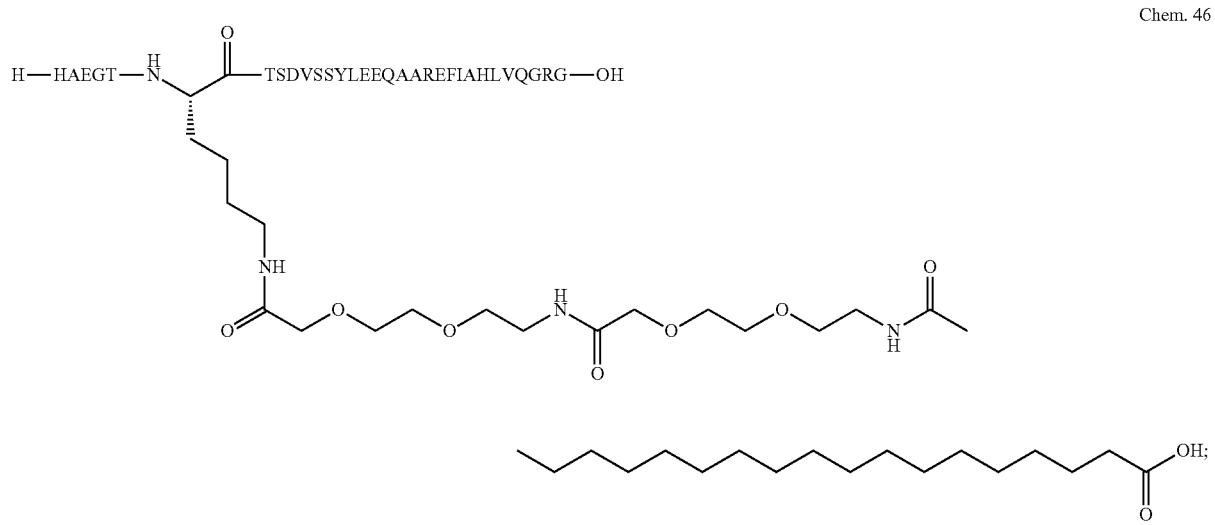

Chem. 46

$N^{\epsilon26}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl]-$N^{\epsilon37}$-[2-(2-[2-(2-[2-(2-[4-(10-(4-Carboxyphenoxy)decanoylamino)-4(S)-carboxybutyrylamino]ethoxy)ethoxy]acetylamino) ethoxy]ethoxy)acetyl][Aib$^8$,His$^{31}$,Gln$^{34}$,Lys$^{37}$]GLP-1(7-37)-peptide (SEQ ID NO: 8)

Chem. 47
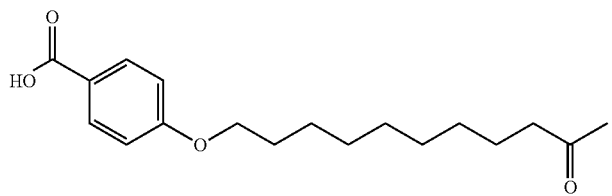
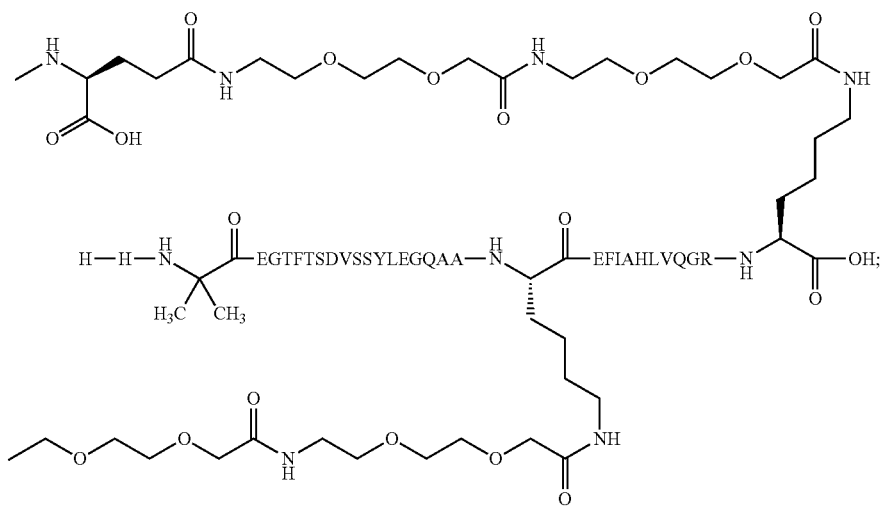
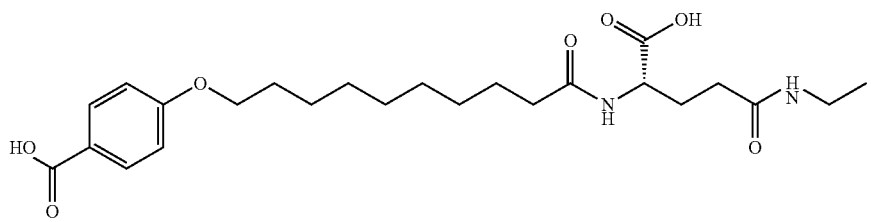
N^{ε26}-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], N^{ε37}-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl] [Aib^8,His^31, Gln^34,Lys^37]GLP-1(7-37)-peptide (SEQ ID NO: 8)
Chem. 48
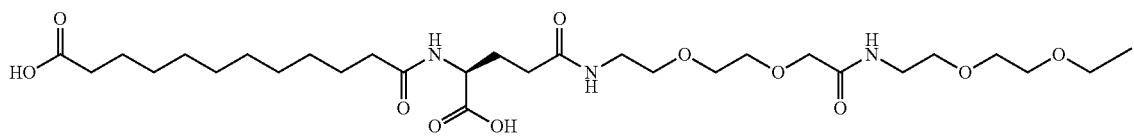

-continued

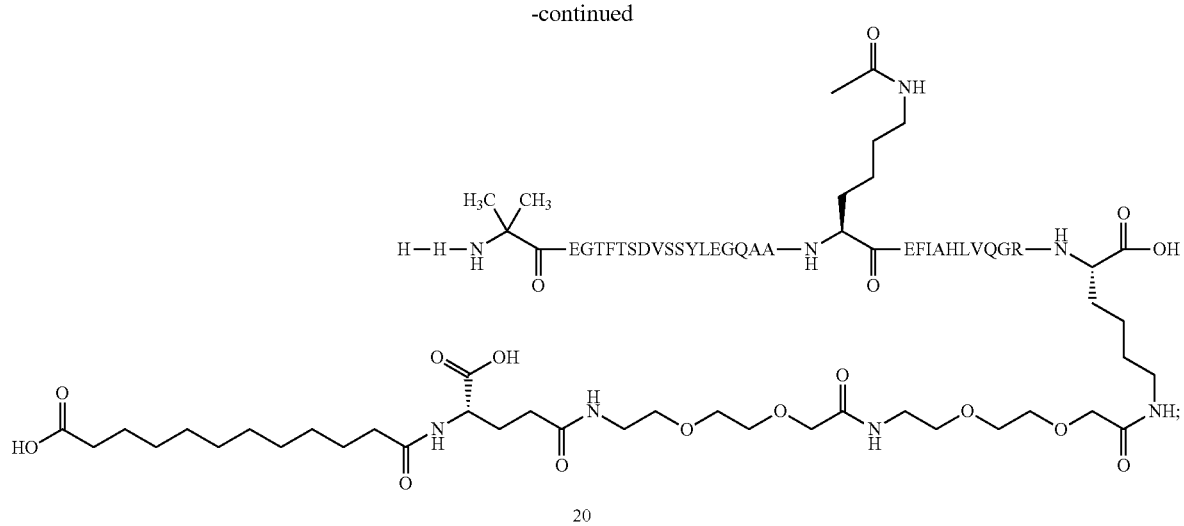

$N^{\epsilon 26}$-2,3-bis[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]propanoyl-[Aib$^8$,His$^{31}$,Gln$^{34}$]-GLP-1-(7-37)-peptide (SEQ ID NO: 4)

Chem. 49

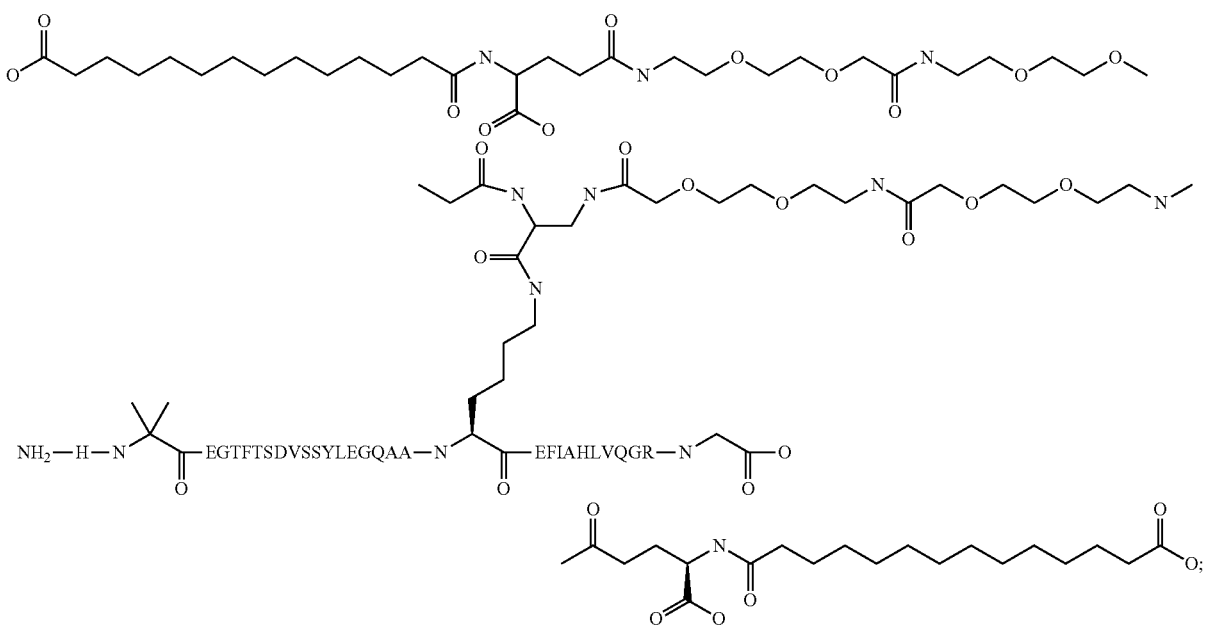

$N^{\epsilon 18}$-18-[2-[2-[2-[[2-[2-[2-[[(4S)-4-carboxy-4-[[1-(19-carboxynonadecanoyl)piperidine-4-carbonyl]amino]butanoyl]amino]ethoxy]ethoxy]acetyl]amino]ethoxy]ethoxy]acetyl]-[Aib$^8$,Lys$^{18}$,Glu$^{22}$,His$^{26}$,His$^{31}$,Gln$^{34}$]-GLP-1-(7-37)-peptide (SEQ ID NO: 13)

Chem. 50

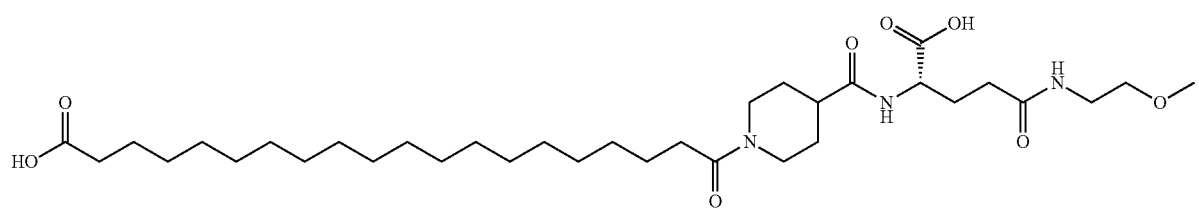

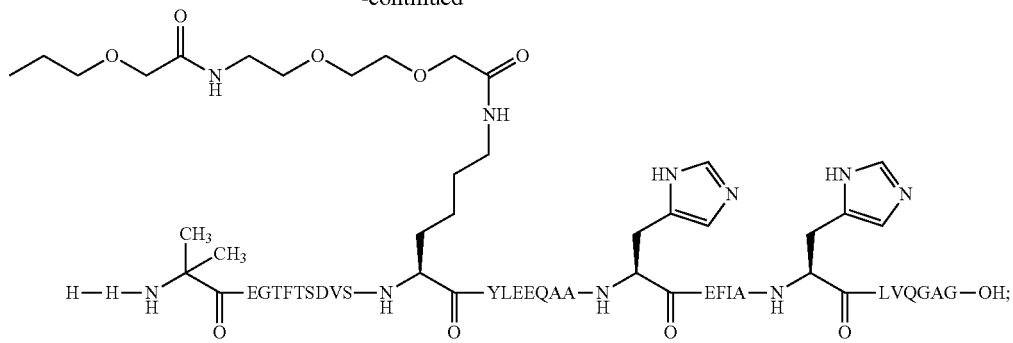
N^{ε27}-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Aib$^8$,Glu$^{22}$,Arg$^{26}$,Lys$^{27}$,Glu$^{30}$,His$^{31}$,Gln$^{34}$,Pro$^{37}$]-GLP-1-(7-37)-peptide (SEQ ID NO: 19)
Chem. 51
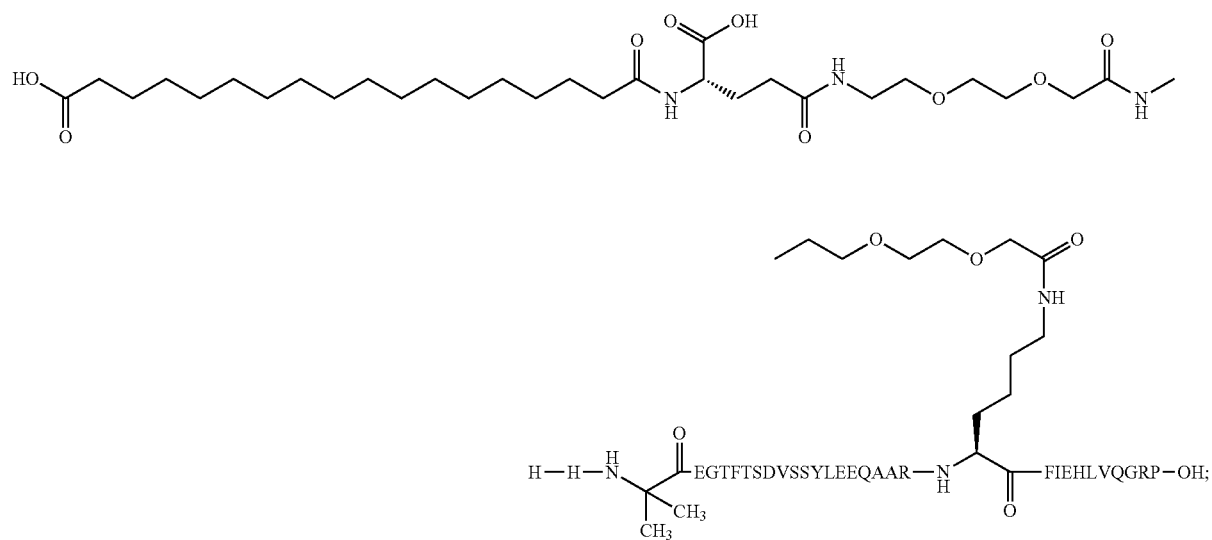
N^{ε26}-[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]acetyl]-[His$^{31}$,Gln$^{34}$]-GLP-1-(7-37)-peptide (SEQ ID NO: 9)
Chem. 52
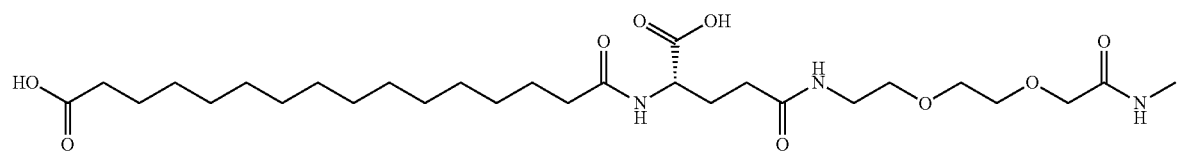

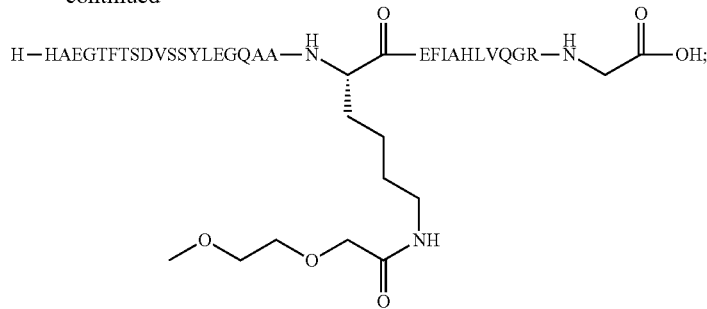

$N^{\epsilon 26}$-4-[16-(1H-tetrazol-5-yl)hexadecanoylsulfamoyl]bu-
tanoyl-[His$^{31}$,Gln$^{34}$]-GLP-1-(7-37)-peptide (SEQ ID
NO: 9)

Chem. 57

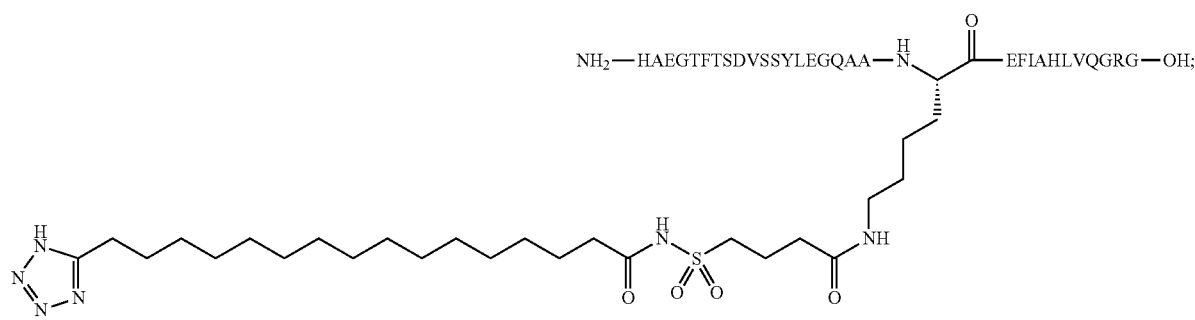

$N^{8}$-methyl, $N^{\epsilon 26}$-[2-[2-[2-[[2-[2-[2-[[(4S)-4-carboxy-4-
(17-carboxyheptadecanoylamino)butanoyl]amino]
ethoxy]ethoxy]acetyl]amino]ethoxy]ethoxy]acetyl]-
[His$^{31}$,Gln$^{34}$]-GLP-1-(7-37)-peptide (SEQ ID NO: 9)

Chem. 58

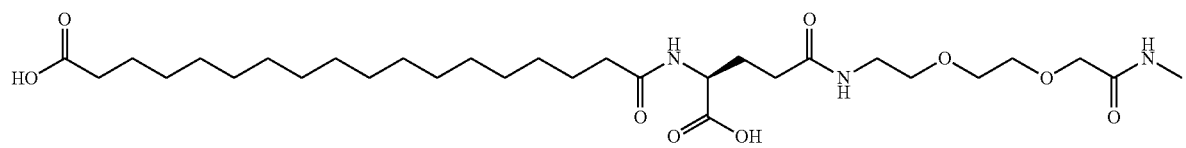

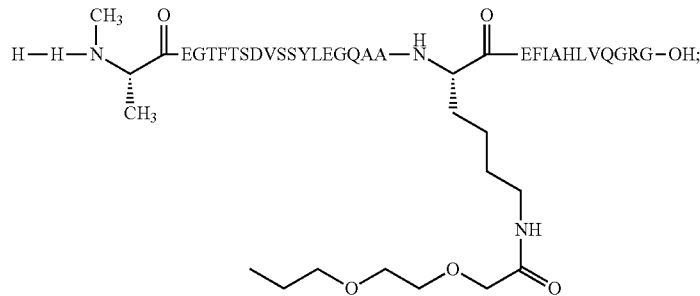

$N^{\epsilon 22}$-[2-[2-[2-[[2-[2-[2-[[(4S)-4-carboxy-4-(17-carboxy-
heptadecanoylamino)butanoyl]amino]ethoxy]ethoxy]
acetyl]amino]ethoxy]ethoxy]acetyl]-[Lys$^{22}$,Arg$^{26}$,
His$^{31}$,Gln$^{34}$]-GLP-1-(7-37)-peptide (SEQ ID NO: 21)

Chem. 59

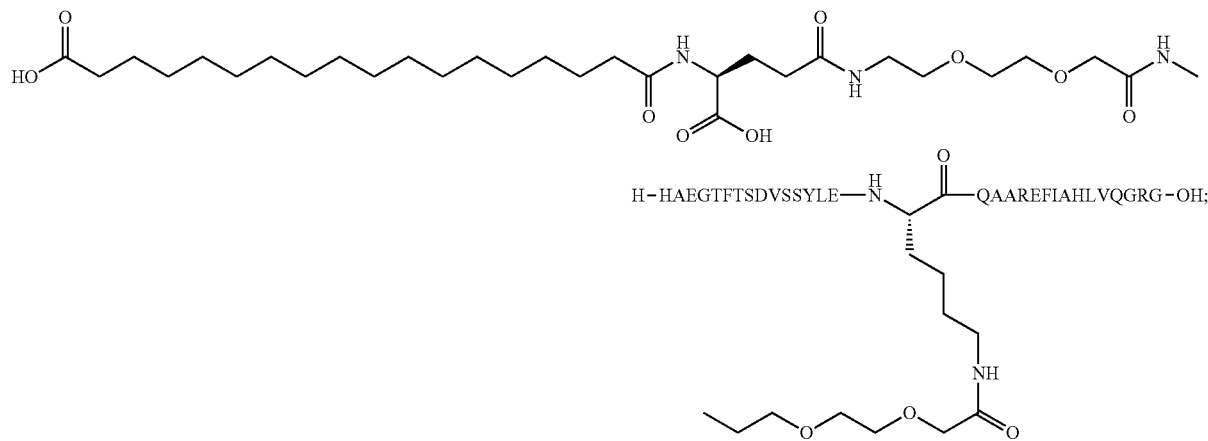

$N^{\epsilon 24}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Aib$^8$,Glu$^{22}$, Lys$^{24}$,Arg$^{26}$,His$^{31}$,Gln$^{34}$]-GLP-1-(7-37)-peptide (SEQ ID NO: 22)

Chem. 60

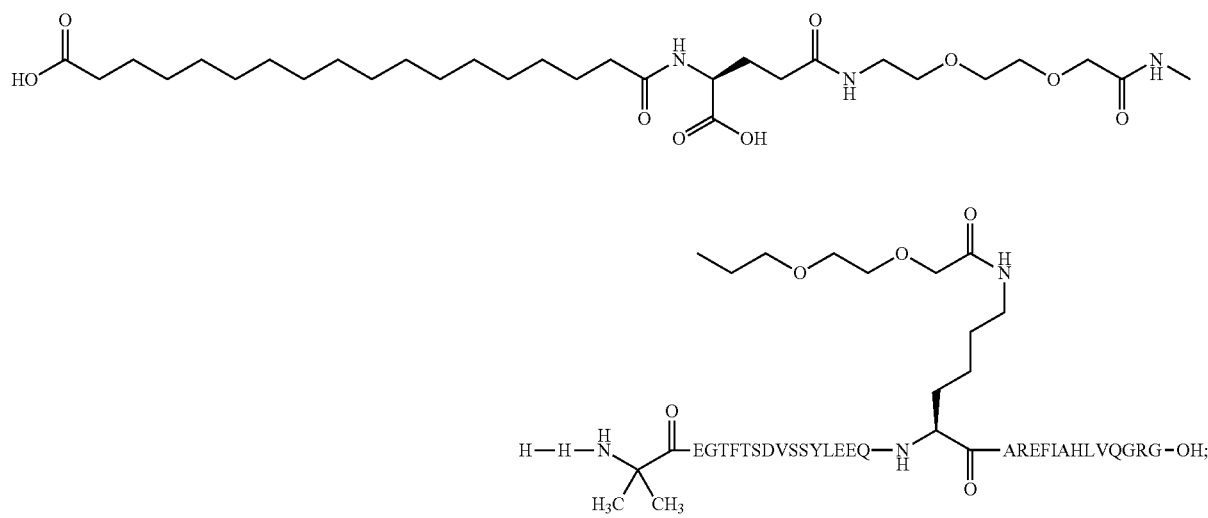

$N^{\epsilon 27}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Aib$^8$,Ile$^{25}$,Arg$^{26}$, Lys$^{27}$,His$^{31}$,Gln$^{34}$]-GLP-1-(7-37)-peptide (SEQ ID NO: 23)

Chem. 61

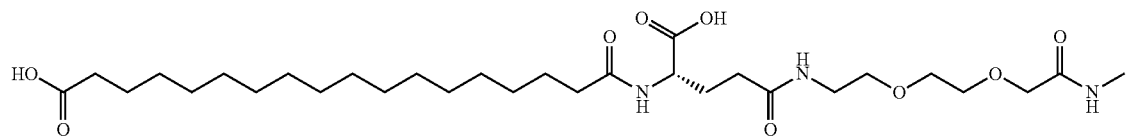

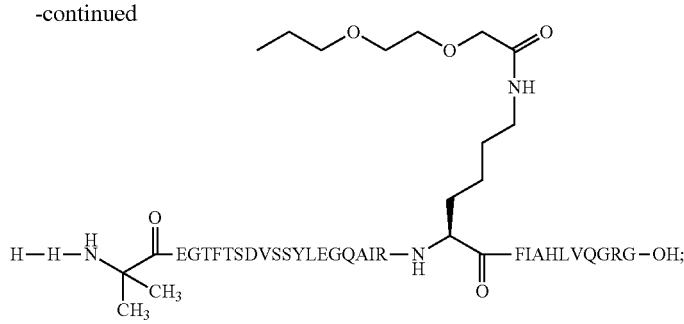

N$^{\epsilon 16}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Aib$^8$,Lys$^{16}$,Glu$^{22}$,Arg$^{26}$,His$^{31}$,Gln$^{34}$]-GLP-1-(7-37)-peptide (SEQ ID NO: 24)

Chem. 62

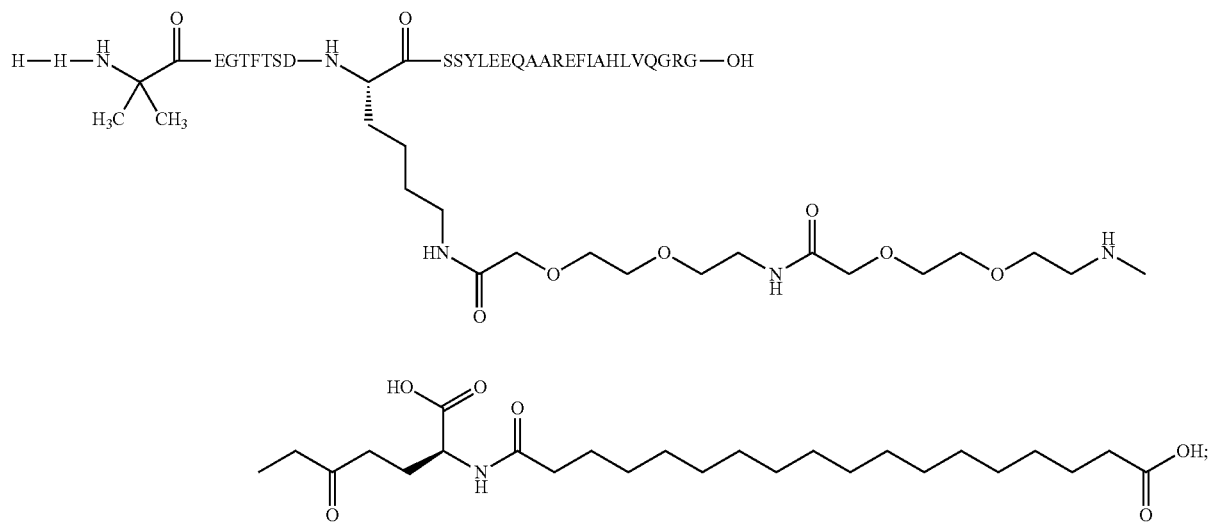

N$^{\epsilon 26}$-[(4S)-4-carboxy-4-(15-carboxypentadecanoylamino)butanoyl]-[His$^{31}$,Gln$^{34}$]-GLP-1-(7-37)-peptide (SEQ ID NO: 9)

Chem. 63

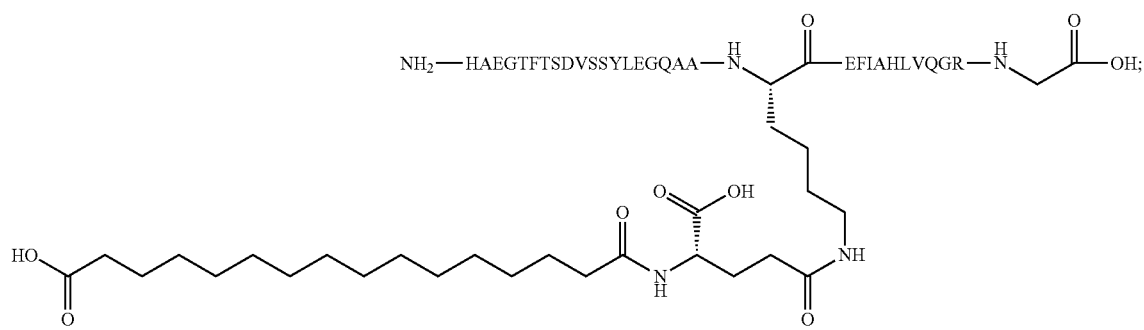

N$^{\epsilon 26}$-[(4S)-4-carboxy-4-(hexadecanoylamino)butanoylH-His$^{31}$,Gln$^{34}$]-GLP-1-(7-37)-peptide (SEQ ID NO: 9)

Chem. 64

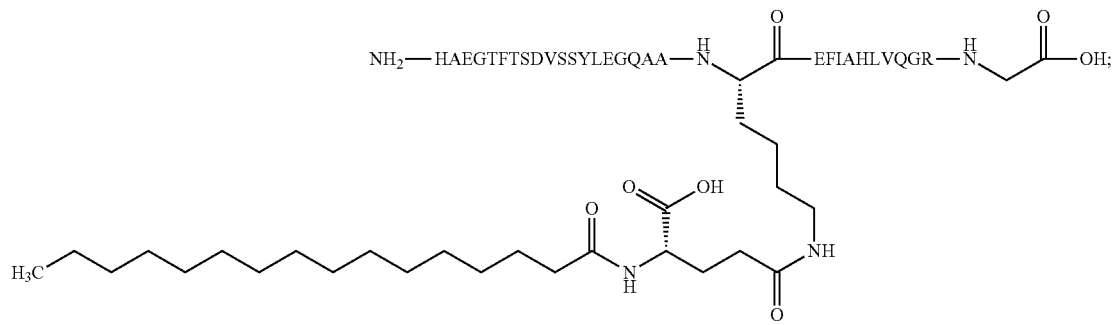

$N^{\epsilon2}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Lys$^{12}$,Glu$^{22}$, Arg$^{26}$,His$^{31}$,Gln$^{34}$]-GLP-1-(7-37)-peptide (SEQ ID NO: 11)

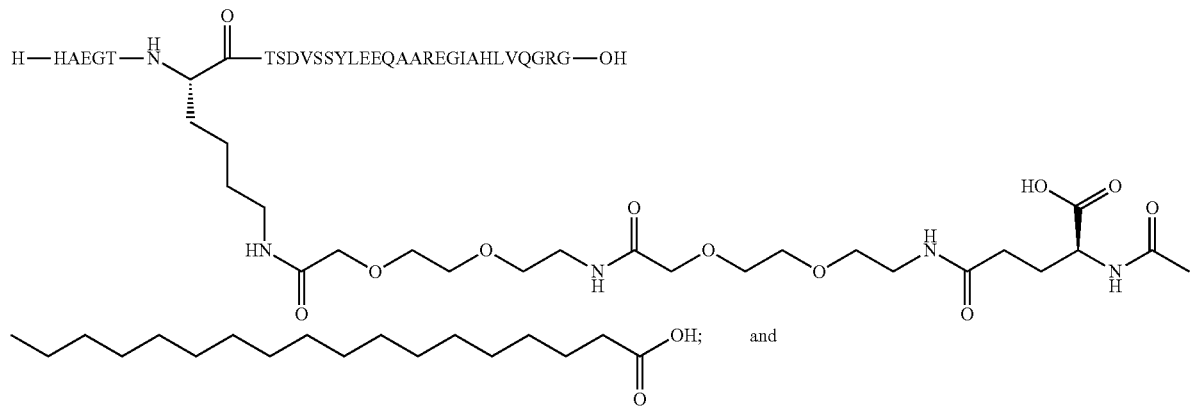

$N^{\epsilon24}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Glu$^{22}$,Lys$^{24}$, Arg$^{26}$,His$^{31}$,Gln$^{34}$]-GLP-1-(7-37)-peptide (SEQ ID NO: 25)

Chem. 66

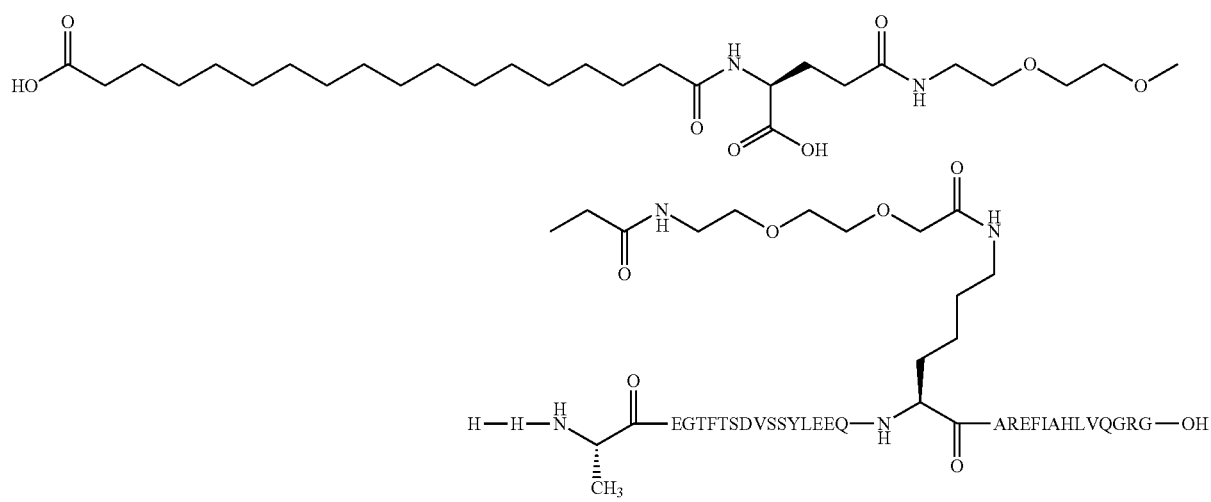

or a pharmaceutically acceptable salt, amide, or ester thereof.

7. A pharmaceutical composition comprising a GLP-1 analogue according to claim 1 in a pharmaceutically acceptable carrier or diluent.

8. A method for treating diabetes in a subject in need of such treatment, said method comprising administering to said subject a therapeutically effective amount of the pharmaceutical composition of claim 7.

9. A pharmaceutical composition comprising a GLP-1 compound according to claim 6 in a pharmaceutically acceptable carrier or diluent.

10. A method for treating diabetes in a subject in need of such treatment, said method comprising administering to said subject a therapeutically effective amount of the pharmaceutical composition of claim 9.

11. A pharmaceutical composition comprising a GLP-1 derivative according to claim 2 in a pharmaceutically acceptable carrier or diluent.

12. A method for treating diabetes in a subject in need of such treatment, said method comprising administering to said subject a therapeutically effective amount of the pharmaceutical composition of claim 11.

* * * * *

UNITED STATES PATENT AND TRADEMARK OFFICE
CERTIFICATE OF CORRECTION

PATENT NO. : 8,815,802 B2
APPLICATION NO. : 13/516312
DATED : August 26, 2014
INVENTOR(S) : Christoph Kalthoff et al.

It is certified that error appears in the above-identified patent and that said Letters Patent is hereby corrected as shown below:

In the Claims

Please replace claim 6, column 167, line 42 with the following:

$N^{\varepsilon 12}$(2-{2-[2-(2-{2-[2-(17-Carboxy-heptadecanoylamino)ethoxy]ethoxy}acetylamino)ethoxy]ethoxy}acetyl) [Aib$^8$,Lys$^{12}$, Glu$^{22}$,Arg$^{26}$,His$^{31}$,Gln$^{34}$]GLP-1(7-37)-peptide(SEQ ID NO: 5)

Please replace claim 6, column 169, line 35 with the following:

$N^{\varepsilon 12}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib$^8$,Lys$^{12}$, Glu$^{22}$,Arg$^{26}$,His$^{31}$,Gln$^{34}$]GLP-1(7-37)-peptide(SEQ ID NO: 5)

Please replace claim 6, column 192, line 50 with the following:

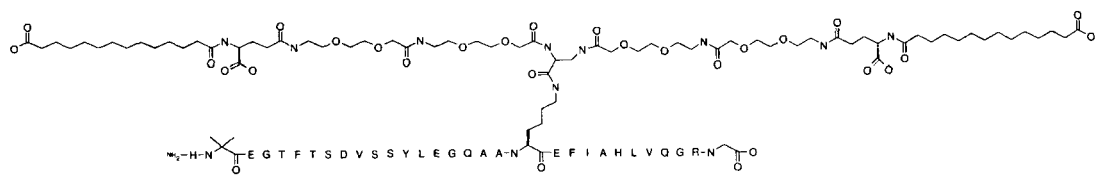

Please replace claim 6, column 199, line 66 with the following:

$N^{\varepsilon 26}$-[(4S)-4-carboxy-4-(hexadecanoylamino)butanoyl]-[His$^{31}$,Gln$^{34}$]-GLP-1-(7-37)-peptide(SEQ ID NO: 9)

Signed and Sealed this
Nineteenth Day of May, 2015

Michelle K. Lee
*Director of the United States Patent and Trademark Office*

CERTIFICATE OF CORRECTION (continued)
U.S. Pat. No. 8,815,802 B2

Please replace claim 6, column 201, line 25 with the following: